United States Patent
Schwartz et al.

(10) Patent No.: US 6,607,888 B2
(45) Date of Patent: Aug. 19, 2003

(54) METHOD FOR ANALYZING NUCLEIC ACID REACTIONS

(75) Inventors: David C. Schwartz, Madison, WI (US); Tian Wu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/838,497

(22) Filed: Apr. 19, 2001

(65) Prior Publication Data

US 2002/0061523 A1 May 23, 2002

Related U.S. Application Data

(63) Continuation-in-part of application No. 09/175,824, filed on Oct. 20, 1998, now Pat. No. 6,221,592.

(51) Int. Cl.[7] .......................... C12Q 1/68; C12P 19/34; C07H 21/02; C07H 21/04; C07H 21/00

(52) U.S. Cl. .................... 435/6; 435/91.1; 435/91.2; 536/23.1; 536/24.3; 536/24.33; 536/25.3

(58) Field of Search .................. 435/6, 91.1, 91.2; 536/23.1, 24.3, 24.33, 25.3

(56) References Cited

U.S. PATENT DOCUMENTS

| | | |
|---|---|---|
| 4,473,452 A | 9/1984 | Cantor et al. |
| 4,695,548 A | 9/1987 | Cantor et al. |
| 4,767,700 A | 8/1988 | Wallace |
| 4,863,849 A | 9/1989 | Melamede |
| 4,870,004 A | 9/1989 | Conroy et al. |
| 4,962,037 A | 10/1990 | Jett et al. |
| 5,059,294 A | 10/1991 | Lizardi |
| 5,079,169 A | 1/1992 | Chu et al. |
| 5,202,231 A | 4/1993 | Drmanac et al. |
| 5,314,829 A | 5/1994 | Coles |
| 5,380,833 A | 1/1995 | Urdea |
| 5,405,747 A | 4/1995 | Jett et al. |
| 5,418,975 A | 5/1995 | Babaian et al. |
| 5,492,806 A | 2/1996 | Drmanac et al. |
| 5,525,464 A | 6/1996 | Drmanac et al. |
| 5,667,972 A | 9/1997 | Drmanac et al. |
| 5,674,743 A | 10/1997 | Ulmer |
| 5,695,940 A | 12/1997 | Drmanac et al. |
| 5,720,928 A | 2/1998 | Schwartz |

FOREIGN PATENT DOCUMENTS

| | | |
|---|---|---|
| WO | WO 84/02001 | 5/1984 |
| WO | WO 93/21340 | 4/1992 |
| WO | WO 94/18218 | 2/1993 |
| WO | WO 96/39417 | 6/1995 |
| WO | WO 96/12039 | 10/1995 |
| WO | WO 96/41011 | 6/1996 |
| WO | WO 99/01744 | 1/1999 |

OTHER PUBLICATIONS

Jing et al., "Automated high resolution optical mapping using arrayed, fluid–fixed DNA molecules," Proc. Natl. Acad. Sci., USA, 1998, vol. 95, pp. 8046–8051.*

Jing et al., "Sequencing double–stranded DNA by strand displacement," Nucleic Acids Research, 1997, vol. 25, No. 3, pp. 677–679.

Jing et al., "Automated high resolution optical mapping using arrayed, fluid–fixed DNA molecules," Proc. Natl. Acad. Sci. USA, 1998, col. 95, pp. 8046–8050.

Meng et al., "Optical mapping of lambda bacteriophage clones using restriction endonucleases." Nature Genetics, 1995, vol. 9, pp. 432–438.

Eldarov et al., "Isolation and characterization of restriction endonuclease BcuAI Bacillus cereus A; restriction endonuclease BcuAi purification; AvaII isoschizomer," Nucleic Acids Research, 1992, vol. 20, No. 11, pp. 2989.

Quake, Stephen, FY 1997, "Fluorescent Photobleaching Method for Sequencing DNA," Abstract, NIH Grant No. 1R29HG01642–01.

Allison et al., 1992, "Immobilization of DNA for Scanning Probe Microscopy," Proc. Natl. Acad. Sci. USA, 89: 10129–10133.

Anantharaman et al., 1997, "Genomics via Optical Mapping II: Ordered Restrictioni Maps," J. Computational Biol., 4:91–118.

Beer and Moudrianakis, 1962, "Determinationi of base Sequence in Nucleic Acids with the Electron Microscope: Visibility of a Marker," Proc. Natl. Acad. Sci. USA 48: 409–416.

Bensimon et al., 1994, "alignment and Sensitive Detection of DNA by a Moving Interface," Science, 265:2096–2098.

Cai et al., 1995, "Ordered Restriction Endonuclease Maps of Yeast Artificial Chromosomes Created by Optical Mapping on Surfaces," Proc. Natl. Acad. Sci. USA, 92:5164–5168.

Chee et al., 1996, "Accessing Genetic Information with High–Density DNA Arrays," Science 274:610–614.

Church and Gilbert, 1984, "Genomic Sequencing," Proc. Natl. Acad. Sci. USA 81:1991–1995.

(List continued on next page.)

Primary Examiner—Kenneth R. Horlick
Assistant Examiner—Young Kim
(74) Attorney, Agent, or Firm—Joseph T. Leone, Esq.; DeWitt Ross & Stevens S.C.

(57) ABSTRACT

Disclosed are methods for analyzing reactions involving nucleic acids. The invention utilizes nucleic acids immobilized on a defined substrate in such a manner that the nucleic acid can participate in enzymatic and chemical reactions. These reactions are carried out in the presence of labeled reagents, thereby enabling the progress of the reactions to be analyzed using various techniques, such a fluorescent microscopy. The invention is particularly well suited for investigating transcription phenomena and generating genome-wide maps based upon reactions of individual nucleic acid molecules.

42 Claims, 24 Drawing Sheets

OTHER PUBLICATIONS

Dempster et al., 1977, "Maximum Likelihood from Incomplete Data via the EM Algorithm," *J. Roy Statis. Soc.*, 38:1–38.

Drmanac et al., 1993, "DNA Sequence Determination by Hybridization: A Strategy for Efficient Large–Scale Sequencing," *Science*, 260:1649–1652.

Florijn et al., 1995, "High–Resolution DNA Fiber–FISH for Genomic DNA Mapping and Colour Bar–Coding of Large Genes," *Hum. Mol. Genet.*, 4:831–836.

Funatsu et al., 1995, "Imaging of single Fluorescent Molecules and Individual ATP Turnovers by Single Myosin Molecules in Aqueous Solution," *Nature*, 374:555–559.

Gelles et al., 1988, "Tracking Kinesin–Driven Movements with Nanometre–Scale Precision," *Nature*, 331:450–453.

Grenander and Miller, 1994, "Representations of Knowledge in Complex Systems," *J. Roy. Statis. Soc.*, 56:549–603.

Gurrieri et al., 1990, "Imaging of Kinked configurations of DNA Molecules Undergoing Orthogonal Field Alternating Gel Electrophoresis by Fluorescence Microscopy," *Biochemistry*, 29:3396–3401.

Haaf et al., 1996, "Chromosomal Localization of Long Trinucleotide Repeats in the Human Genome by Fluorescence in situ Hybridization," *Nature Genet.* 12:183–185.

Harding and Keller, 1992, "Single–Molecule Detection as an Approach to Rapid DNA Sequencing," *TIBTECH*, 10:55–57.

Heller et al., 1997, "Discovery and Analysis of Inflammatory Disease–Related Genes Using cDNA Microarrays," *Proc. Natl. Acad. Sci. USA*, 94:2150–2155.

Heng et al., 1992, "High–Resolution Mapping of Mammalian Genes by in situ Hybridization to Free Chromatin," *Proc. Natl. Acad. Sci. USA*, 89:9509–9513.

Houseal et al., 1989, "Real–Time Imaging of Single DNA Molecules with Fluorescence Microscopy," *Biophys. J.*, 56:507–516.

Jett et al., 1990, "High–Speed DNA Sequencing: An Approach Based Upon Fluorescence Detection of Single Molecules," *Structures & Methods*, vol. I: Human Genome Initiative & DNA Recombination, Sarma & Sarma, eds., Adenine Press, pp. 79–87 [reprinted from *J. Biomol. Struct. Dyn.* 7:301–309 (1989)].

Jing et al., 1998, "Automated High Resolution Optical Mapping Using Arrayed, Fluid–Fixed DNA Molecules," *Proc. Natl. Acad. Sci. USA*, 95:8046–8051.

Kieleczawa et al., 1992, "DNA Sequencing by Primer Walking with Strings of Contiguous Hexamers," *Science*, 258:1789–1791.

Koch et al., 1989, "Oligonucleotide–Priming Methods for the Chromosome–Specific Labelling of Alpha Satellite DNA in situ," *Chromosoma* 98:259–265.

Kotler et al., 1993, "DNA Sequencing: Modular Primers Assembled from a Library of Hexamers or Pentamers," *Proc. Natl. Acad. Sci. USA*, 90:4241–4245.

Lawrence et al., 1988, Sensitive, High–Resolution Chromatin and Chromosome Mapping In Situ: Presence and Orientation of Two Closely Integrated Copies of EBV in a Lymphoma Line, *Cell*, 52:51–61.

Livak et al., 1995, "Towards Fully Automated Genome–Wide Polymorphism Screening," *Nature Genet.*, 9:341–342.

Livak et al., 1995, "Oligonucleotides with Fluorescent Dyes at Opposite Ends Provide a Quenched Probe System Useful for Detecting PCR Product and Nucleic Acid Hybridization," *PCR Meth. & Applic.*, 4:357–362.

Manuelidis et al., 1982, "High–Resolution Mapping of Satellite DNA Using Biotin–Labeled DNA Probes," *J. Cell. Biol.*, 95:619–625.

Matsumoto et al., 1981, "Light Microscopic Structure of DNA in Solution Studied by the 4'6–Diamidino–2–Phenylindole Staining Method," *J. Mol. Biol.*, 152:501–516.

Meng et al., 1995, "Optical mapping of Lambda Bacteriophage Clones Using Restriction Endonucleases," *Nature Genetics*, 9:432–438.

Michalet et al., 1997, "Dynamic Molecular Combing: Stretching the Whole Human Genome for High–Resolution Studies," *Science*, 277:1518–1523.

Muthukrishnan and Parida, 1997, "Towards Constructing Physical Maps by Optical Mapping: An Effective, Simple Combinatorial Approach," in: Proceedings of the First Annual Conference on Computational Molecular Biology, ACM Press, pp. 209–215.

Nickerson et al., 1990, "Automated DNA Diagnostics Using an ELISA–Based Oligonucleotide Ligation Assay," *Proc. Natl. Acad. Sci. USA*, 87:8923–8927.

Nikiforov et al., 1994, "Genetic Bit Analysis: A solid Phase Method for Typing Single Nucleotide Polymorphisms," *Nucl. Acids Res.*, 22:4167–4175.

Nižetiĉ et al., 1991, "Construction, Arraying, and High–Density Screening of Large Insert Libraries of Human Chromosomes X and 21: Their Potential use as Reference Libraries," *Proc. Natl. Acad. Sci. USA*, 88:3233–3237.

Ohi e al., 1978, "Mapping of Mitochondrial 4S RNA Genes in *Xenopus laevis* by Electron Microscopy," *J. Mol. Biol.*, 121:299–310.

Porath and Axen, 1976, "Immobilization of Enzymes to Agar, Agarose, and Sephadex Supports," *Meth. Enzymol.*, 44: 19–45.

Prober et al., 1987, "A System for Rapid DNA sequencing with Fluorescent Chain–Terminating Dideoxynucleotides," *Science*, 238:336–341.

Quake, 1997, "Fluorescent Photobleaching Method for Sequencing DNA," NIH Grant Proposal No. R29HG01642–01 Summary Only.

Samiotaki et al., 1994, "Dual–Color Detection of DNA Sequence Variants by Ligase–Mediated Analysis," *Genomics*, 20:238–242.

Schena et al., 1995, "Quantitative Monitoring of Gene Expression Patterns with a Complementary DNA Microarray," *Science*, 270:467–470.

Schmidt et al., 1996, "Imaging of Single Molecule Diffusion," *Proc. Natl. Acad. Sci. USA*, 93:2926–2929.

Schröock et al., 1996, "Multicolor Spectral Karyotyping of Human Chromosomes," *Science*, 273:494–497.

Scwartz et al., 1993, "Ordered Restriction Maps of *Saccharomyces cereevisiae* Chromosomes Constructed by Optical Mapping," *Science*, 262:110–114.

Schwartz and Koval, 1989, "Conformational Dynamics of Individual DNA Molecules During Gel Electrophoresis," *Nature*, 338–520–522.

Smith et al., 1992, "Direct Mechanical Measurements of the Elasticity of Single DNA Molecules by Using Magnetic Beads," *Science*, 258:1122–1126.

Smith et al., 1989, "Observation of Individual DNA Molecules Undergoing Gel Electrophoresis," *Science*, 243:203–206.

Speicher et al., 1996, "Karyotyping Human Chromosomes by Combinatorial Multi–Fluor FISH," *Nature Genet.*, 12:368–375.

Strathmann et al., 1991, "Transposon–Facilitated DNA Sequencing." *Proc. Natl. Acad. Sci.* USA, 88:1247–1250.

Syvänen, 1994, "Detection of Point Mutations in Human Genes by the Solid–Phase Minisequencing Method," *Clinica Chimica Acta.*, 226:225–236.

Szybalski, 1990, "Proposal for Sequencing DNA Using Ligation of Hexamers to Genrate Sequential Elongation Primers," *Gene*, 90:177–178.

Tabor and Richardson, 1990, "DNA Sequence Analysis with a Modified Bacetriophage T7 DNA Polymerase: Effect of Pyrophsphorolysis and Metal Ions," *J. Biol. Chem.*, 2665:8322–8328.

Trask, 1991, "DNA Sequence Localization in Metaphase and Interphase Cells by Fluorescence in situ Hybridization," *Meth. Cell Biol.*, 35:4–35.

Voss et al., 1993, "Automated Low–Redundancy Large–Scale DNA Sequencing in Promer Walking," *BioTechniques*, 15:714–721.

Walker et al., 1992, "Strand Displacement Amplification—as Isothermal, in vitro DNA Amplification Technique," *Nucl. Acids Res.*, 20:1691–1696.

Wang et al., 1995, "Optical Mapping of Site–Directed Cleavage on Single DNA Molecules by the RecA–Assisted Restriction Endonuclease Technique," *Proc. Natl. Acad. Sci.* USA, 92:165–169.

Weier et al., 1995, "Quantitative DNA Fiber Mapping," *Hum. Mol. Genet.*, 4:1903–1910.

Yanagida et al., 1986, "Video–Connected Fluorescence Microscopy of Large DNA Molecules, Chromatin and Chromosomes," in: *Applications of fluorescence in the Biomedical Sciences*, Taylor et al., eds., Alan R. Liss, NY, pp. 321–345.

Yanagida et al., 1983, "Dynamic Behaviors of DNA Molecules in Solution Studied by Fluorescence Microscopy," Cold Spring Harbor Symp. Quant. Biol., 47:177–187.

* cited by examiner

MELTED STRANDS,
PRIMER ANNEALED

_____

_____

_____

| ADD DIDEOXY NTP ($a^d$)
| AND POLYMERASE.
↓

$a^d$ _____

..atggctat

| WASH. ADD NTPs,
| FLUOROCHROME LABELED
| dUTP.
↓

$a^d$ _____

..atggctat
NO LABEL ADDED.

-OR-

| ADD DIDEOXY NTP ($t^d$) AND
| POLYMERASE. WASH.
| FOLLOW WITH NTPs,
| FLUOROCHROME LABELED
| dUTP.

$u^f$ accgau$^f$ a _____
..a tggcta t

PRIMER EXTENSION OCCURS,
LABEL ADDS.

FIG.3

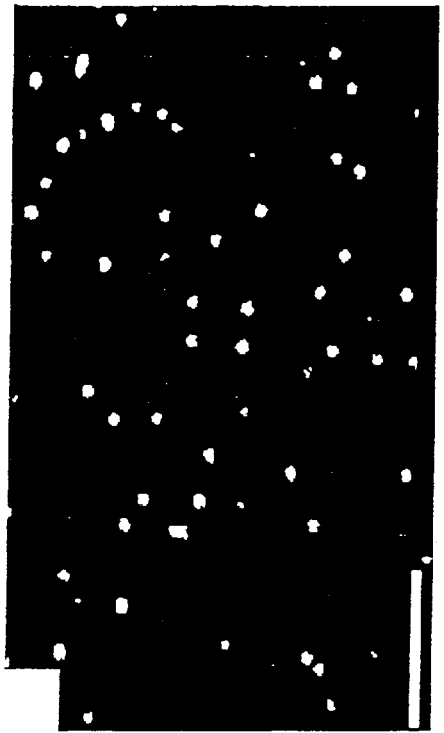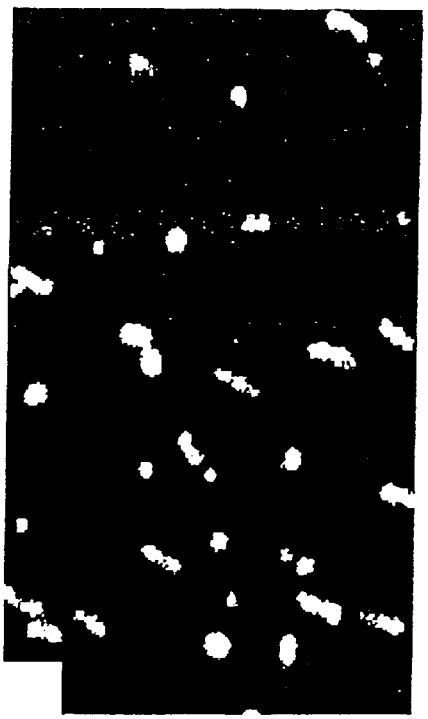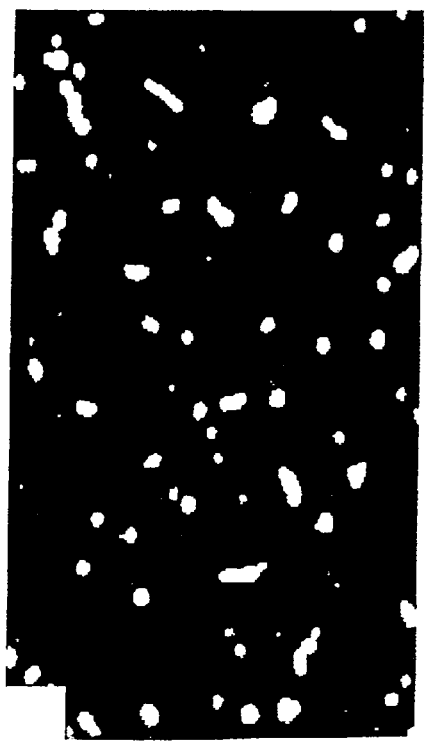
FIG. 17A
FIG. 17B
FIG. 17C

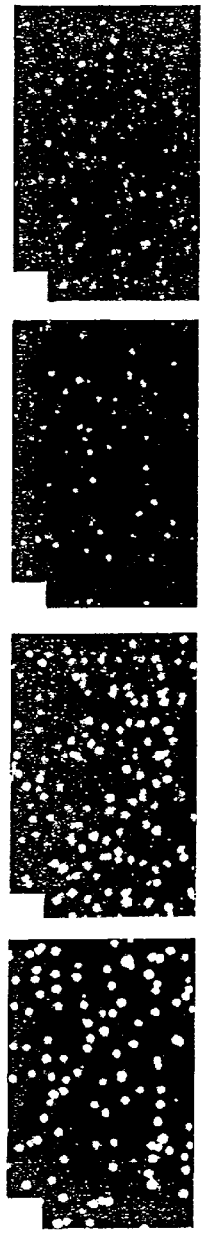
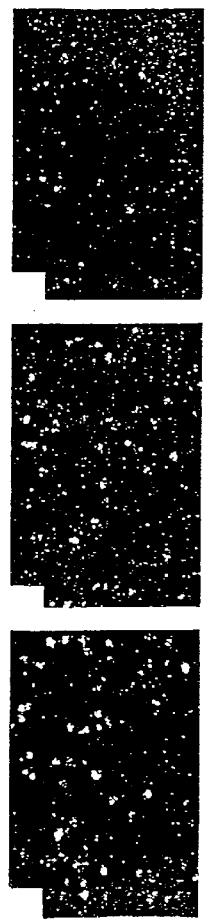
FIG.18A FIG.18B FIG.18C FIG.18D FIG.18E FIG.18F FIG.18G FIG.18H FIG.18I FIG.18J FIG.21A
FIG.21B
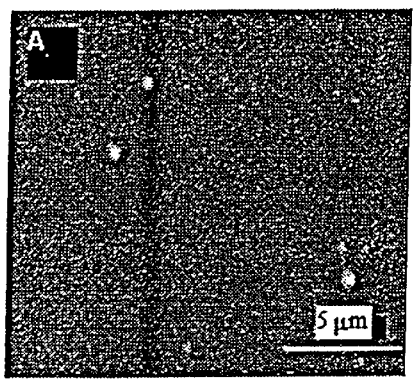
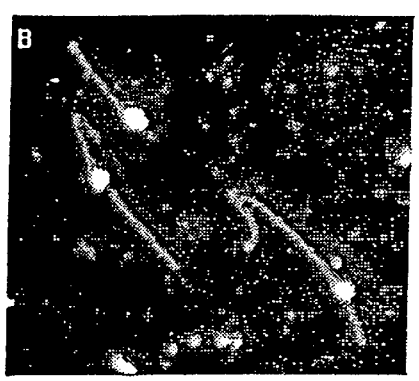
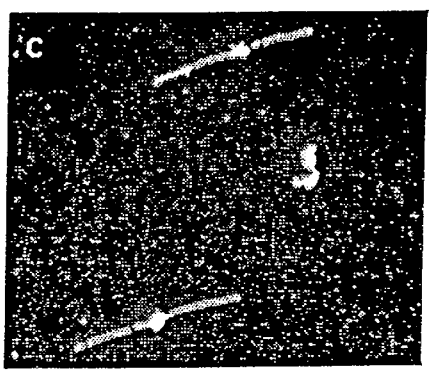
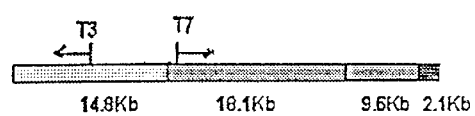
FIG.21D
FIG.21C FIG.22A
FIG.22B
FIG.22C
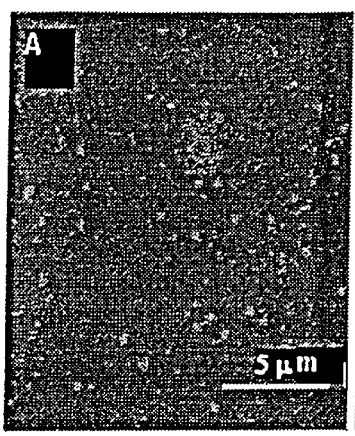
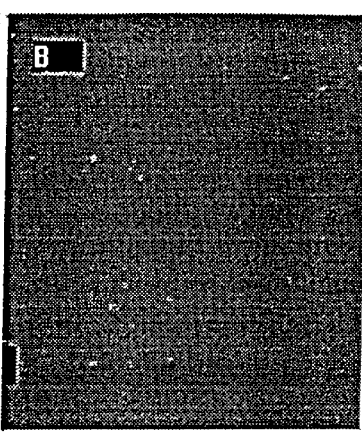
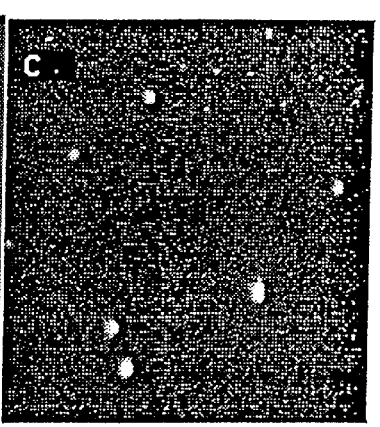
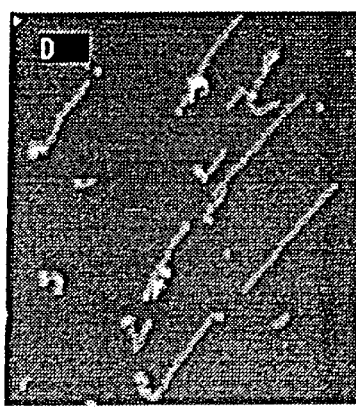
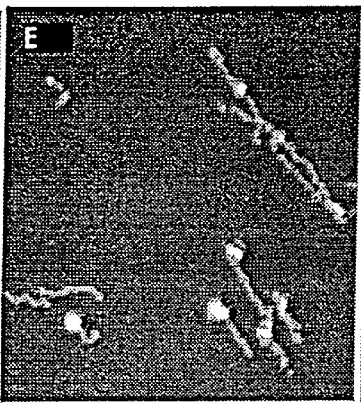
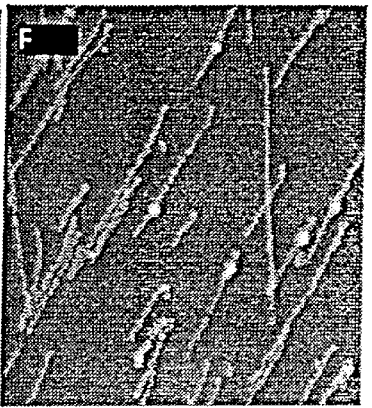
FIG.22D
FIG.22E
FIG.22F FIG23A  FIG.23B
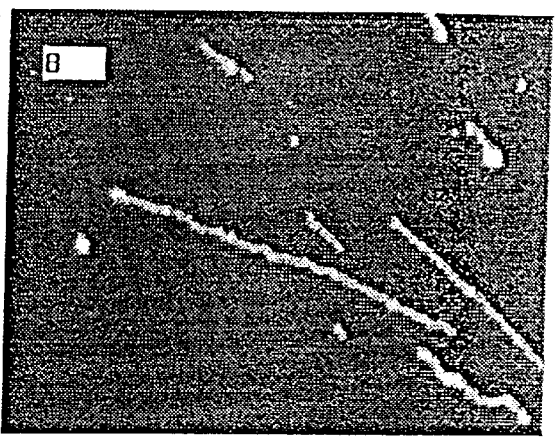
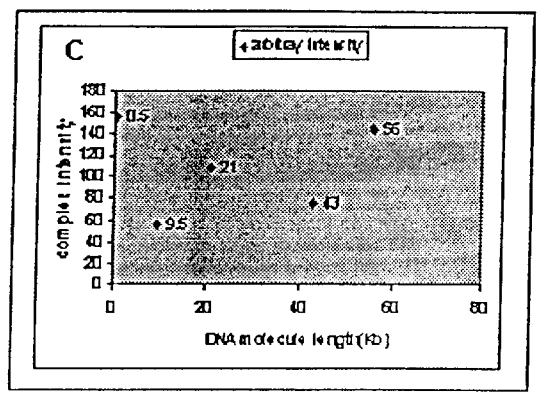
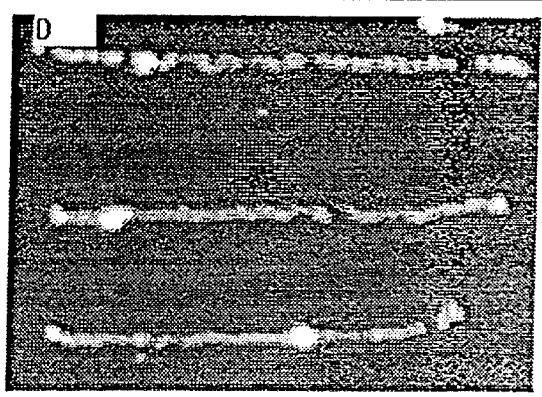
FIG.23C  FIG24D

METHOD FOR ANALYZING NUCLEIC ACID REACTIONS

CROSS-REFERENCE TO RELATED APPLICATIONS

This is a continuation-in-part of application Ser. No. 09/175,824, filed Oct. 20, 1998, now U.S. Pat. No. 6,221,592 B1, issued Apr. 24, 2001, the entire contents of which is incorporated herein.

1. INTRODUCTION

The present invention relates to methods for analyzing nucleic acid reactions in general and transcription reactions in particular. The method utilizes individual nucleic acid molecules immobilized along their length on a planar substrate. Using optical techniques, such as epifluorescent microscopy, the reactions of individual nucleic acid molecules can be studied using the method described herein.

The present invention also relates to scalable and massively automatable methods for imaging nucleic acid reactions, either in stop-action fashion or in real time. Bayesian inference estimation methods are utilized to analyze a population of images and to produce data sets of genome-sized scale to be used in the identification of genes, promoter regions, termination regions, or virtually any other phenomena associated with transcription or reverse-transcription of nucleic acid molecules. The method can be used to fabricate maps of transcription events, to correlate these maps to restriction site maps, and to use these data to identify from where in a sequenced genome a single nucleic acid molecule originated.

2. BACKGROUND

The analysis of nucleic acid molecules at the genome level is an extremely complex endeavor which requires accurate, rapid characterization of large numbers of often very large nucleic acid molecules via high throughput DNA mapping and sequencing. The construction of physical maps, and ultimately of nucleotide sequences, for eukaryotic chromosomes currently remains laborious and difficult. This is due, in part, to the fact that current procedures for mapping and sequencing DNA were originally designed to analyze nucleic acids at the gene, rather than at the genome, level (Chumakov, et al., 1992, Nature 359:380; Maier, et al., 1992, Nat. Genet. 1:273).

2.1. DNA Sequencing

Approaches to DNA sequencing have varied widely, and have made it possible to sequence entire genomes, including portions of the human genome. The most commonly used method has been the dideoxy chain termination method of Sanger (1977, Proc. Natl. Acad. Sci. USA 74:5463). However, this method is time-consuming, labor-intensive and expensive, requiring the analysis of four sets of radioactively labeled DNA fragments resolved by gel electrophoresis to determine the DNA sequence.

To overcome some of these deficiencies, automated DNA sequencing systems were developed which used four fluorescently labeled dideoxy nucleotides to label DNA (Smith et al., 1985, Nucleic Acids Res. 13:2399–2412; Smith et al., 1986, Nature 321:674; Prober et al., 1987, Science 238:336–341, which are incorporated herein by reference). Automated slab gel electrophoresis systems enable large-scale sequence acquisition (Roach et al., 1995, Genomics 26:345–353; Venter et al., 1996, Nature 381:364–366; Prober et al., 1987, Science 238:336–341; Lake et al., 1996, Science 273:1058; Strathmann et al., 1991, Proc. Natl. Acad. Sci. USA 88:1247–1250; and the complete genomic sequence of *Saccharomyces cerevisiae* in the Stanford database). Current large-scale sequencing is largely the domain of centers where costly and complex support systems are essential for the production efforts. Efforts to deal with sequence acquisition from a large population (usually less than 1,000) is limited to relatively small numbers of loci (Davies et al., 1995, Nature 371:130–136). However, these methods are still dependent on Sanger sequencing reactions and gel electrophoresis to generate ladders and robotic sample handling procedures to deal with the attending numbers of clones and polymerase chain reacting products.

Some recently developed methods and devices for automated sequencing of bulk DNA samples that utilize fluorescently labeled nucleotides are described in U.S. Pat. No. 5,674,743; International Application Nos. PCT/GB93/00848 published Apr. 22, 1993 as WO 93/21340; PCT/US96/08633 published Jun. 4, 1996 as WO 96/39417; and PCT/US94/01156 published Jan. 31, 1994 as WO 94/18218. None of the recently developed methods is capable of sequencing individual nucleic acid molecules.

Techniques for sequencing large genomes of DNA have relied upon the construction of Yeast Artificial Chromosomes ("YAC") contiguous sequences. Preliminary physical maps of a large fraction of the human genome have been generated via YACs (Cohen et al., 1993, Nature 366:698–701). However, extensive high resolution maps of YACs have not been widely generated, due to the high frequency of rearrangement/chimerism among YACs, the low complexity of fingerprints generated by hybridization approaches, and the extensive labor required to overcome these problems. Ordered maps of YACs have been optically made by using a spermine condensation method (to avoid shearing the DNA) and fixing the clones in molten agarose onto derivatized glass surfaces (Cai et al., 1995, Natl. Acad. Sci. USA 92:5164–5168). There have been several proposals for the rapid attainment of sequence data from clones that minimize or obviate the need for shotgun sequencing approaches or subcloning of large insert clones (Smith et al., 1994, Nature Genet. 7:40–47; Kupfer et al., 1995, Genomics 27:90–100; Chen et al., 1993, Genomics 17:651–656 and Roach et al., 1995, Genomics 26:345–353). Several of these approaches advocate the generation of "sequence sampled maps" (Smith et al., 1994, Nature Genet. 7:40–47 and Venter et al., 1996, Nature 381:364–366) which require fingerprinting of clones, or large numbers of subclones, to achieve good target coverage while simultaneously generating a fine-scale map.

A recent development has been the proposal of DNA sequencing of aligned and oriented Bacterial Artificial Chromosomes ("BAC") contiguous sequences (Venter et al., 1996, Nature 381:364–366); (see also Smith et al., 1994, Nature Genetics 7:40–47; Kupfer et al., 1995, Genomics 27:90–100; and Chen et al., 1993, Genomics 17:651–656). BACs offer the advantage of considerably greater stability than YACs, are more easily physically managed due to their smaller size (~500 kb to 2 Mb versus ~100 to 200 kb, respectively), and are more compatible with automated DNA purification procedures (Kim et al., 1996, Proc. Natl. Acad. Sci. USA 93:6297–6301; Kim et al., 1994, Genomics 24:527–534; and Schmitt et al., 1996, Genomics 33:9–20). Further approaches for the optical analysis of BAC clones were also developed (Cai et al., 1998, Proc. Natl. Acad. Sci. USA 95:3390–3395).

Limitations of these approaches described above include low throughput, DNA fragmentation (preventing subsequent or simultaneous multimethod analyses), and difficulties in automation. Despite the potential utilities of these and other approaches, it is increasingly clear that current molecular approaches were developed primarily for characterization of single genes, not entire genomes, and are, therefore, not optimally suited to the analysis of polygenic diseases and complex traits, especially on a population-wide basis (Risch et al., 1996, Science 273:1516–1517).

2.2. Visualization and Surface Mounting of Single DNA Molecules

Single molecule approaches represent a subset of current physical and genetic mapping approaches constitute the two major approaches to genomic analysis, and are critical to mapping and cloning of disease genes and to direct sequencing efforts. Such methods of visualization of single DNA molecules include fluorescence microscopy in solution (Yanagida et al., 1986, in *Applications of fluorescence in the biomedical sciences* Taylor et al. (eds), Alan Liss, New York, pp 321–345; Yanagida et al., 1983, Cold Spring Harbor Symp. Quantit. Biol. 47:177; Matsumoto et al., 1981, J. Mol. Biol. 132:501–516; Schwartz et al., 1989, Nature 338:520–522; and Houseal et al., 1989, Biophys. J. 56:507–516); FISH (Manuelidis et al., 1982, J. Cell. Biol. 95:619; Lawrence et al., 1988, Cell 52:51; Lichter et al., 1990, Science 247:64; Heng et al., 1992, Proc. Natl. Acad. Sci. USA 89:9509; van den Engh et al., 1992, Science 257:1410); visualization by scanning tunneling microscopy or atomic force microscopy techniques (Keller et al., 1989, Proc. Natl. Acad. Sci. USA 86:5356–5360; see, e.g., Karrasch et al., 1993, Biophysical J. 65:2437–2446; Hansma et al., 1993, Nucleic Acids Research 21:505–512; Bustamante et al., 1992, Biochemistry 31:22–26; Lyubchenko et al., 1992, J. Biomol. Struct. and Dyn. 10:589–606; Allison et al., 1992, Proc. Natl. Acad. Sci. USA 89:10129–10133; Zenhausern et al., 1992, J. Struct. Biol. 108:69–73); visualization of circular DNA molecules (Bustamante et al., 1992, Biochemistry 31:22–26); DNA bending in transcription complexes by scanning force microscopy (Rees et al., 1993, Science 260:1646–1649); direct mechanical measurement of the elasticity of single DNA molecules using magnetic beads (Smith et al., 1992, Science 258:1122–1126); alignment and detection of DNA molecules involving either elongation of end-tethered surface bound molecules by a receding air-water interface (U.S. Pat. No. 5,079,169; U.S. Pat. No. 5,380,833; Perkins et al., 1994, Science 264:819; and Bensimon et al., 1994, Science 265:2096–2098), and elongation of non-tethered molecules by 'fluid fixation' (Samad et al., 1995, Nature 378:516–517; Cai et al., 1995, Proc. Natl. Acad. Sci. USA 92:5164–5168; Meng et al., 1995, Nature Genet. 9:432–438; Wang et al., 1995, Proc. Natl. Acad. Sci. USA 92:165–169; and Schwartz et al., 1993, and Science 262:110–114); (See also Reed et al., "A Quantitative Study Of Optical Mapping Surfaces By Atomic Force Microscopy And Restriction Endonuclease Digestion" in press, Analytical Biochemistry; Cai et al., "High Resolution Restriction Maps Of Bacterial Artificial Chromosomes Constructed By Optical Mapping", 1998, Proc. Natl. Acad. Sci. USA 95:3390–3395; Samad and Schwartz, "Genomic Analysis by Optioal Mapping" in *Analytical Biotechnology-Genomic Analysis* in press, (see also, U.S. Pat. No. 6,147,198, issued Nov. 4, 2000 to David C. Schwartz and incorporated herein); Schwartz et al., 1997, Current Opinion in Biotechnology, 8:70–74; Samad, 1995, Genomics Research 59:1–4; and Primrose, 1995, *Principles of Genome Analysis: A guide to mapping and sequencing DNA from different organisms*, Blackwell Science Ltd., Oxford England, pp. 76–77; and Bautsch et al., 1997 "Long-Range Restriction Mapping of Genomic DNA" in *Genomic Mapping: A Practical Approach*, Chapter 12, Paul H. Dear ed., Oxford University Press, New York, pp. 281–313).

New modes of molecular investigation have emerged from advances in molecular fixation techniques, labeling, and the development of scanning probe microscopies (Keller et al., 1989, Proc. Natl. Acad. Sci. USA 86:5356–5360; Bensimon et al., 1994, Science 265:2096–2098; Guthold et al., 1994, Proc. Natl. Acad. Sci. USA, 91:12927–12931; Hansma et al., 1996, Nucleic Acids Res. 24:713–720; Cai et al., 1995, Proc. Natl. Acad. Sci. USA 92:5164–5168; Meng et al., 1995, Nature Genet. 9:432–438; Weier et al., 1995, Hum. Mol. Genet. 4:1903–1910; Wang et al., 1995, Proc. Natl. Acad. Sci. USA 92:165–169; Schwartz et al., 1993, Science 262:110–114; Schena et al., 1995, Science 270:467–470; Heller et al., 1997, Proc. Natl. Acad. Sci. USA 94:2150–2155; Erie et al., 1994, Science 266:1562–1566; and Leuba et al., 1994, Proc. Natl. Acad. Sci. USA 91:11621–11625). In particular, molecular fixation techniques have relied on the application of outside forces such as electrical fields, a travelling meniscus (Michalet et al., 1997, Science 277:1518) or end-tethering of molecules with beads (Strick et al., 1996, Science 271:1835–1837) to fix DNA to solid surfaces. Biochemistries have been performed on surface-mounted DNA molecules, but the procedures used bulk deposition and analysis (Schena et al., 1995, Science 270:467–470; Heller et al., 1997, Proc. Natl. Acad. Sci. USA 94:2150–2155; Craig et al., 1990, Nucleic Acids Res. 18:2653–2660; and Nizetic et al., 1991, Proc. Natl. Acad. Sci. USA 88:3233–3237).

Once the nucleic acid molecules are fixed, they must be imaged and analyzed. Although the spatial resolution of conventional light microscopy is limited, cooled, charged-coupled (CCD) imaging devices have stimulated the development of new optical approaches to the quantitation of nucleic acids, that may supplant electrophoresis-based techniques in many applications (Schena et al., 1995, Science 270:467–470; Lipshutz et al., 1995, Biotechniques 19:442–447; and Chee et al., 1996, Science 274:610–614). Yanagida and coworkers (Yanagida et al., 1996, in *Applications of fluorescence in the biomedical sciences*, Taylor et al. (eds), Alan Liss, New York, pp. 321–345) first investigated the molecular motions of fluorescently stained individual DNA molecules in solution by image-enhanced fluorescence microscopy. Optical mapping was subsequently developed for the rapid production of ordered restriction maps from individual, fluorescently stained DNA molecules (Cai et al., 1995, Proc. Natl. Acad. Sci. USA 92:5164–5168; Meng et al., 1995, Nature Genet. 9:432–438; Wang et al., 1995, Proc. Natl. Acad. Sci. USA 92:165–169; Schwartz et al., 1993, Science 262:110–114; Schwartz et al., 1997, Curr. Opinions in Biotechnology 8:70–74; Samad et al., Nature 378:516–517; and Samad et al., 1995, Genomic Research 59:1–4).

In the original method, individual fluorescently labeled yeast chromosomes were elongated and fixed in a flow of molten agarose generated between a coverslip and a glass slide (Schwartz et al., 1993, Science 262:110–114). Restriction endonuclease cleavage events were recorded as time-lapse images, following addition of magnesium ions to activate the added endonuclease. Cleavage sites appeared as growing gaps due to relaxation of DNA coils at nascent ends, and maps were constructed by measuring fragment sizes using relative fluorescent intensity or apparent length measurements.

In another closed system, the DNA molecules (2–1,500 kb) were elongated and fixed using the flow and adhesion forces generated when a fluid sample is compressed between two glass surfaces, one derivatized with polylysine or APTES (Meng et al., 1995, Nature Genet. 9:432–438 and Cai et al., 1995, Proc. Natl. Acad. Sci. USA 92:5164–5168). Fixed molecules were digested with restriction endonucleases, fluorescently stained (Rye et al., 1992, Nucleic Acids Res. 20:2803–2812) and optically mapped (Meng et al., 1995, Nature Genet. 9:432–438 and Cai et al., 1995, Proc. Natl. Acad. Sci. USA 92:5164–5168). However, closed systems have limited access to the samples and cannot readily accommodate arrayed samples (Bensimon et al., 1994, Science 265:2096–2098 and Meng et al., 1995, Nature Genet. 9:432–438).

To increase the throughput and versatility of optical mapping and sequencing, multiple samples need to be arrayed on a single mapping surface. Although robotic gridding techniques for DNA samples exist (Heller et al., 1997, Proc. Natl. Acad. Sci. USA 94:2150–2155; Craig et al., 1990, Nucl. Acids Res. 18:2653–2660; and Nizetic et al., 1991, Proc. Natl. Acad. Sci. USA 88:3233–3237), such approaches were not designed to work with single molecule substrates and could not be relied upon to deposit molecules retaining significant accessibility to enzymatic action.

While single molecule techniques offer the potential advantage of an ordering capability which gel electrophoresis lacks, none of the current single molecule techniques can be used, on a practical level, as high resolution genomic sequencing tools. The molecules described by Yanagida (Yanagida, M. et al., 1983, Cold Spring Harbor Symp. Quantit. Biol. 47:177; Matsumoto, S. et al., 1981, J. Mol. Biol. 132:501–516) were visualized, primarily free in solution making any practical sequencing impossible. Further, while the FISH technique offers the advantage of using only a limited number of immobilized fragments, usually chromosomes, it is not possible to achieve the sizing resolution available with gel electrophoresis.

Single molecule tethering techniques, as listed above, generally involve individual nucleic acid molecules which have, first, been immobilized onto a surface via one or both of their ends, and, second, have been manipulated such that the molecules are stretched out. These techniques, however, are not suited to genome analysis. First, the steps involved are time consuming and can only be accomplished with a small number of molecules per procedure. Further, in general, the tethered molecules cannot be stored and used again.

Recently, special effort has centered on development of improved surface-based approaches for DNA fixation, compatible with a variety of molecular imaging techniques. Desirable DNA fixation attributes include: a usable population of elongated molecules, preservation of biochemical activity, parallel sample processing capabilities, high sample deposition rates, densely gridded samples and easy access to arrayed samples.

Present-day array hybridization technology already involves gridding DNA samples densely on open-faced, charged-membrane surfaces (Craig et al., 1990, Nucl. Acids Res. 18:2653–2660; and Nizetic et al., 1991, Proc. Natl. Acad. Sci. USA 88:3233–3237). Gridded sample arrays facilitate biochemical manipulations and analyses and are limited only by sample density and available biochemistries.

New approaches to molecular deposition, called "fluid fixation," involve placing small droplets of DNA solution onto critically derivatized glass surfaces which readily elongates and fixes DNA molecules. Conveniently, application of outside forces are completely obviated in the fluid fixation technique, thereby making use of electrical fields, a travelling meniscus or end-tethering of molecules unnecessary. The passive nature of fluid fixation provides the platform needed for efforts to automate optical mapping and sequencing.

The observation of single fluorochromes using video rate imaging techniques has been described by Schmidt et al. (Schmidt et al., 1996, Proc. Natl. Acad. Sci. USA 93:2926–2929) using a standard fluorescence microscope, laser illumination, and a cooled CCD camera with frame shifting capability. A significant advance in signal/noise optimization was made by Funatsu et al. (Funatsu et al., 1995, Nature 374:555–559) by systematically minimizing noise in virtually every possible experimental and instrumentational variable.

In conclusion, a rapid, accurate method of optically sequencing individual nucleic acid molecules was needed in the art. Such nucleotide sequencing of single molecules would be useful for aligning/overlapping contiguous sequences for genomic mapping and genomic analysis, and in rapidly analyzing single nucleotide polymorphisms in a population of individual nucleic acid molecules.

Citation of documents herein is not intended as an admission that any of the documents cited herein is pertinent prior art, or an admission that the cited documents are considered material to the patentability of the claims of the present application. All statements as to the date or representations as to the contents of these documents are based on the information available to the applicants and does not constitute any admission as to the correctness of the dates or contents of these documents.

2.3. Transcription Analysis

The recently published human genome maps have given us the first rough draft of our own human DNA genome. Venter et al., 2001, *Science* 291:1304–1350; International Human Genome Sequencing Consortium, 2001, *Nature* 409:860–921. A human transcriptome map was also constructed by using SAGE (serial analysis of gene expression) and provided a high-resolution view of gene distribution in chromosomal domains. Caron et al., 2001, *Science* 291:1289–1292. The achievement of this important milestone in genomic science was made possible through a combination of technological and organizational breakthroughs, and is now poised to serve as the touchstone for major discoveries in the biological sciences. Obviously, however, deciphering the nucleotide sequence of the human genome is only the first and perhaps smallest step in the process. The challenge now at hand is to discern the biological and biochemical significance embedded within the roughly 3,000,000,000 bases within the human genome. The same problem exists in the study of other, less massive genomes, such as those of bacteria and virus. Careful and comprehensive study of transcriptional patterns within different organisms, cell-types, and environments is a critical consideration in this effort. Underlying these studies are the basic biochemical mechanisms that define transcriptional activities at the molecular level.

While the approaches and systems developed for large-scale sequencing have laid the foundation for a broad range of high-throughput systems for molecular analysis, these approaches are not well-suited for studying biochemical mechanisms associated with transcription. The present invention, however is an in vitro method and device, a "system," that looks to the single molecule level for tracking numerous steps involved in gene expression and its modulation. While looking at individual molecules to study nucleic acid reactions and interactions, the method of the present invention can use an entire genome as a template, thereby elucidating transcription phenomena at an unprecedented scale and with unprecedented speed. The system utilizes biochemical and detection systems that readily enable statistical and computational analysis of the large data sets generated by the method. The method utilizes this optical mapping system to construct physical (an correlatable) maps of transcription events and restriction sites from ensembles of single DNA molecules.

Modern approaches to expression profiling based on microarrays and Affymetrix-brand chips (Affymetrix, Inc., Santa Clara, Calif.) are already proving their value in identifying genes associated with cellular function and development. Such studies are also providing the early clues to how networks of genes and their products work together to produce observable phenotypes. In addition, the identification of disease-related genes opens new routes for rational pharmaceutical intervention. The technologies that enabled these new studies include hybridization-based techniques (DNA microarrays), PCR-based techniques (differential display); sequence based techniques (SAGE; serial analysis of gene expression), and MPSS (massively parallel signature sequencing). Kozian & Kirschbaum, 1999, *TIBTECH*, 17:73–78.

DNA microarrays are now widely used for expression profiling, because they are intrinsically massively parallel and experimentally accessible. Brown & Botstein, 1999, *Nature Genetics* 21:33–37. Two main technologies are commonly used to produce DNA chips: photolithography as developed by Affymetrix and mechanical grid systems, which deposit PCR products or clones into two-dimensional arrays. Celis et al., 2000, FEBS Letters 480:2–16. While these approaches analyze the expression levels of thousands of genes simultaneously, they each suffer from insurmountable limitations, such as scalability, speed, and ease of automation. See, for example, Celis et al., supra.

3. SUMMARY OF THE INVENTION

The present invention is based on the development of techniques to grid multiple individual nucleic acid molecule samples, to image individual substrate molecules and single labeled nucleotides using automated fluorescence microscopy; and to integrate with a scheme for automatic construction of restriction fragment and DNA sequence maps to create a methods and systems which eliminate operator interaction. The present invention also correlates these data with transcription events, such as initiation, pause, termination, etc. The invention thus includes a method for mapping transcription events, using an entire genome as a template, as well as a method to correlate those transcription events with restriction sites within the same genome.

Specifically, a first embodiment of the invention is directed to a method of analyzing enzymatic and chemical reactions of nucleic acids. The method comprises elongating and fixing onto a surface of a substrate a plurality of nucleic acid molecules in such a fashion that each individual nucleic acid molecule is fixed along its length onto the surface of the substrate with a small degree of relaxation so that the nucleic acid molecules are individually analyzable and accessible for enzymatic and chemical reactions. Then the elongated and fixed nucleic acid of step (a) are subjected to an enzymatic or chemical reaction in the presence of a labeled reagent that generates signals correlating to the enzymatic or chemical reaction. The, the signals generated by the labeled reagent are acquired and compiled, whereby the enzymatic or chemical reaction of step is analyzed.

Another embodiment of the invention is directed to a method of analyzing enzymatic and chemical reactions of nucleic acids, the method comprising first elongating and fixing onto a surface of a substrate a plurality of nucleic acid molecules in such a fashion that each individual nucleic acid molecule is fixed along its length onto the surface of the substrate with a small degree of relaxation so that the nucleic acid molecules are individually analyzable and accessible for enzymatic and chemical reactions. The elongated and fixed nucleic acid is then subjected to a transcription reaction followed by a restriction reaction in the presence of a labeled reagent that generates signals correlating to the transcription reaction and the restriction reaction, respectively. Then acquiring and compiling the signals generated by the labeled reagent. The acquired and compiled signals generated by the labeled reagent are then compiled into an image. Individual elongated nucleic acid molecules are observed for the appearance of complexes corresponding to transcription events in the individual nucleic acid molecule; the same individual molecules are also observed for the appearance of gaps corresponding to cleavage sites between restriction fragments. These steps are reiterated on additional individual elongated nucleic acid molecules, to thereby generate additional images. The images are then compiled into an ordered map correlating transcription event sites and restriction enzyme cleavage sites based upon the images.

Moreover, the map so generated can then be compared to known genomic sequences, whereby it can be determined from where within a genome a single nucleic acid molecule originated.

A still further embodiment of the invention is directed to a method of analyzing enzymatic and chemical reactions of nucleic acids wherein the nucleic acid is subjected to a reaction in a vessel, followed by transfer of the resction products to an optical mapping surface. Here, the method comprises subjecting nucleic acid molecules to an enzymatic or chemical reaction in the presence of a labeled reagent that generates signals correlating to the enzymatic or chemical reaction, thereby generating nucleic acid reaction products. Then elongating and fixing onto a surface of a substrate a plurality of the nucleic acid reaction products in such a fashion that each individual nucleic acid molecule is fixed along its length onto the surface of the substrate with a small degree of relaxation so that the nucleic acid molecules are individually analyzable and accessible for further enzymatic and chemical reactions. The signals generated by the labeled reagent, are then acquired and compiled whereby the enzymatic or chemical reaction is analyzed. Maps can be generated from these reactions in the same fashion as noted in the preceding paragraphs.

4. BRIEF DESCRIPTION OF THE FIGURES

FIG. 3 is a diagram of the scheme for the optical SNP detection process.

Figure 1:
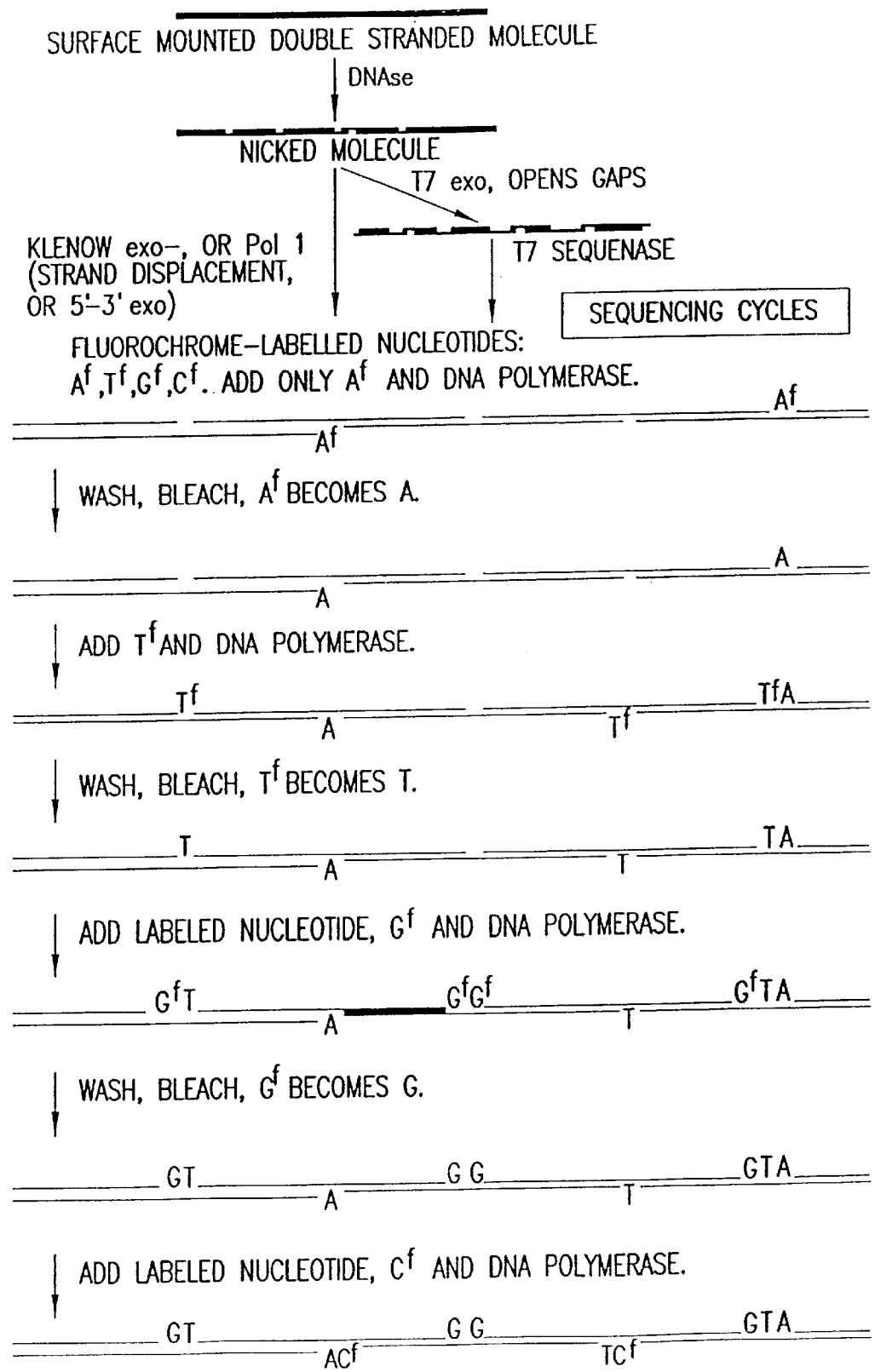
FIG. 1 is an illustration of the biochemical scheme for Optical Sequencing showing the series of biochemical cycles and intermittent washes.

FIG. 12 shows digital fluorescence micrographs of gridded spots containing fluid fixed molecules. Droplets of lambda bacteriophage DNA dissolved in TE buffer containing 0.5% glycerol deposited onto APTES treated glass surfaces, dried and stained. Bars: 20 $\mu$m (A, B, C); 5 $\mu$m (D, E, F). (A) Section of a 10×10 spot grid on a derivatized surface. Image composed by tiling a series of 16× (objective power) images. (B) Close-up of a DNA spot within the grid. Image composed by tiling a series of 16× images. (C) Elongated DNA molecules on surface before restriction digestion (16×). (D) Magnified image of elongated DNA molecules contained within the spot shown in (B) before restriction digestion, 100×. (E) DNA molecules in (B), different field, after digestion with BamH I (100×). Note appearance of gaps signalling enzyme cleavage sites. (F) DNA molecules after digestion with Ava I, from another grid spot, using same surface and spotting conditions (100×).

FIG. 13 shows images of fluid fixation molecular events imaged by video microscopy during droplet drying. Fluorochrome labeled lambda bacteriophage DNA solution was droplet pipetted (1 $\mu$l) onto a derivatized surface and imaged during drying. (A) schematic detailing experimental setup: (1) droplet; (2) surface; (3) support; (4) objective. Phase one: the droplet flattens (B–E). (B) Several molecules are absorbed to the surface. A new molecule (vertical arrow) enters the field of view from the left (time=0 s); (C) the molecule moves above the surface towards the edge of the droplet (0.10 s); (D–E) one end is adsorbed onto the surface and the molecule stretches out in the liquid flow (0.23–0.27 s); (F) the molecule elongate's in the flow, sequentially attaching to the surface at several points along the backbone (0.30 s). Phase two: the contact-line recedes (G–J, 2.53–3.20 s). DNA molecules are elongated and fixed before the receding liquid/air interface (horizontal arrows) sweeps by.

Figure 14A:
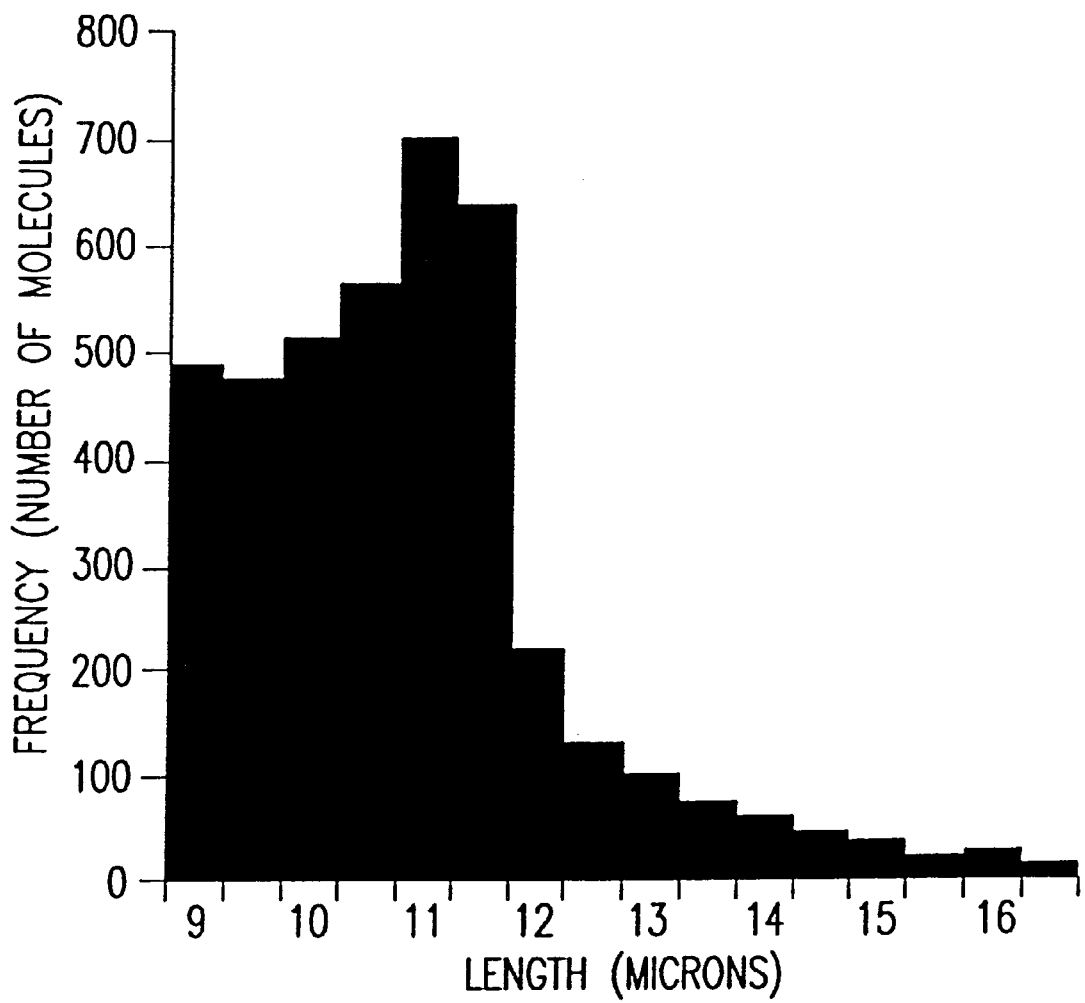
Figure 14B:
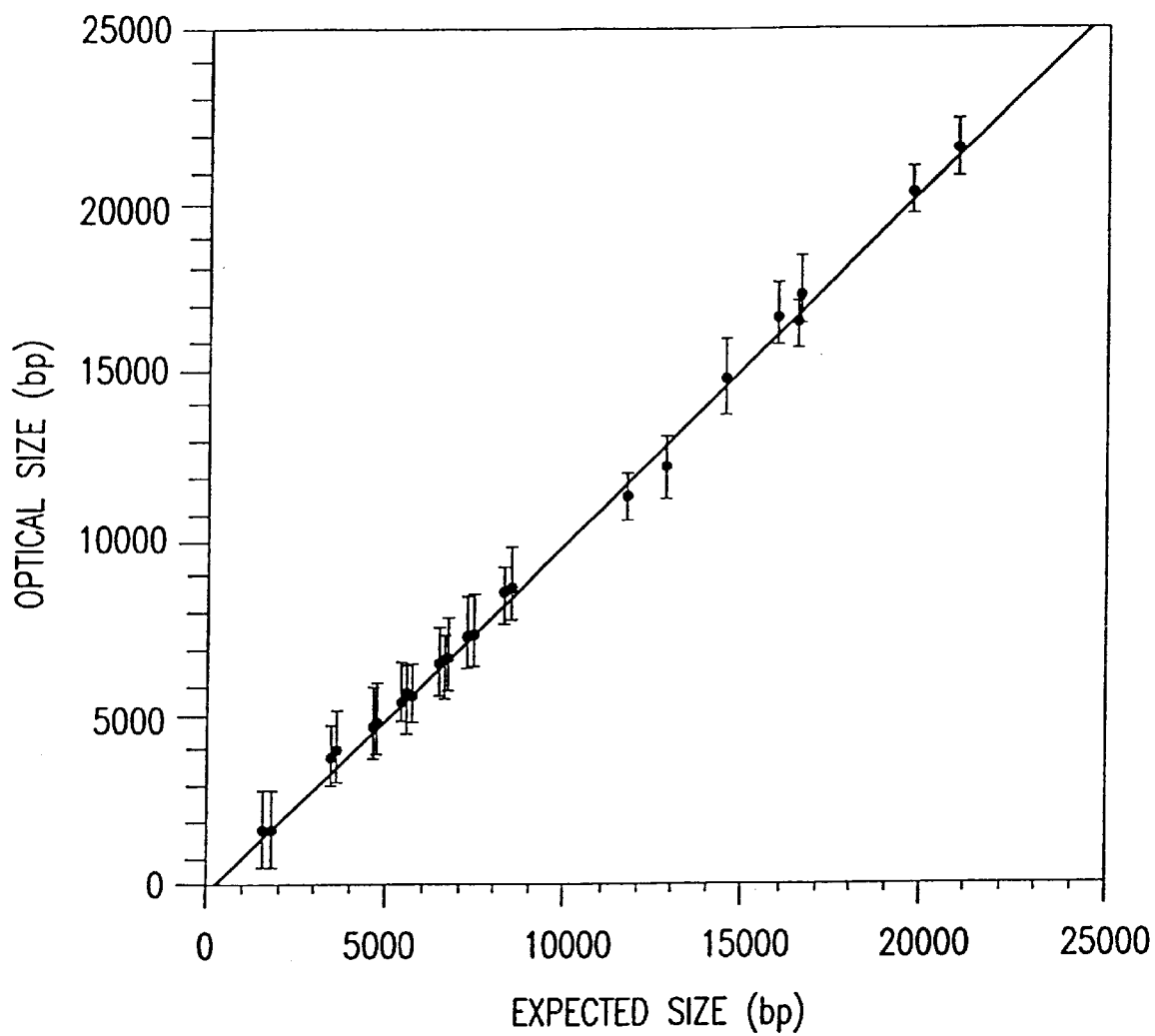

FIGS. 14A and 14B are histograms showing the evaluations of optical mapping molecular parameters and sizing error. (A) Histogram of lengths of spotted adenovirus type 2 DNA molecules. Lengths of 4,242 molecules from 11 spots (49 images per spot) measured by OMM were pooled and analyzed. Histogram shows the fraction (33.4%) of molecules which are sufficiently elongated for mapping ($\leq 65\%$ of the full contour length). The remaining fraction is primarily completely relaxed molecules or "balls", that randomly populate the spotted areas. The average molecular length is 10 $\mu$m. (B) Sizing precision and accuracy. Restriction fragment sizing results for lambda bacteriophage DNA obtained by optical mapping plotted against sequence data. Fragment sizes range from 1,602 bp to 21,226 bp. Error bars represent SD of the means. Lambda DNA spotted on an APTES surface was digested with ApaL I, Ava I, BamH I, Eag I, or EcoR I. 10–30 images were collected from one spot and analyzed by OMM.

FIG. 15 is photographs showing nick translation labeling of fluid fixed lambda bacteriophage DNA molecules using a fluorochrome-bearing nucleotide (R110-dUTP). DNA molecules fixed onto derivatized glass surfaces prior to labeling by nick translation. Bars: 4 $\mu$m. (A) Overview of a spot (edge) using a 16× objective. (B) The same spot portion imaged with a 100× objective. (C) Counter staining with YOYO3 (separate experiment). The absence of heavily punctated staining patterns along molecule backbones indicates the general absence of gaps, or double strand breaks. Staining is not robust due to fluorochrome-fluorochrome interaction.

Figure 16:
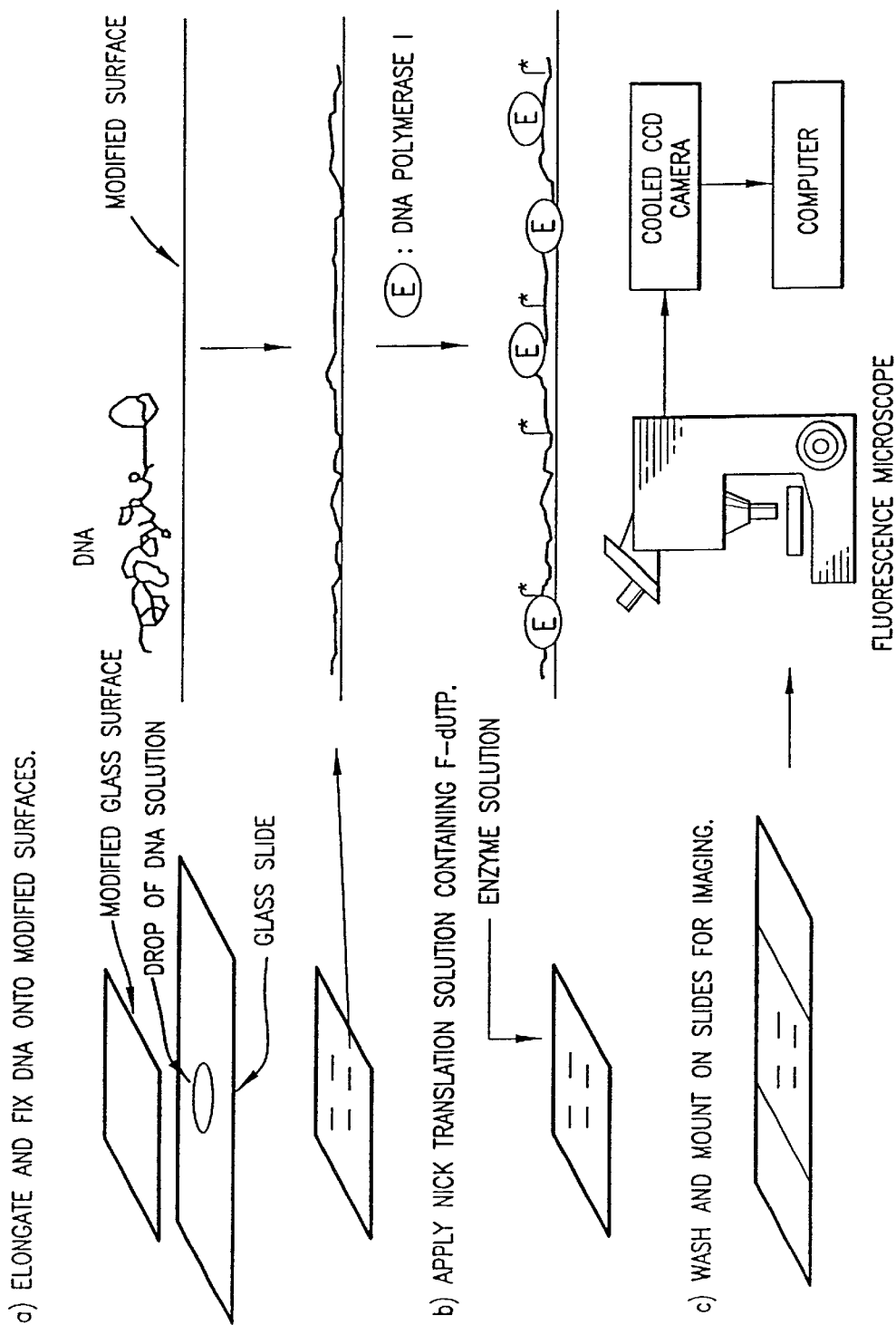
Figure 19D:
Figure 19C:
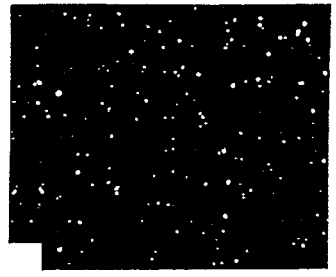
Figure 19B:
Figure 19A:
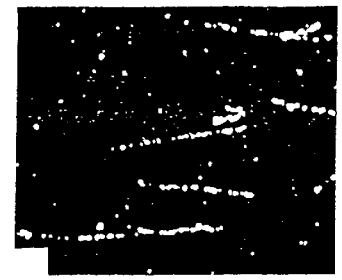
Figure 19H:
Figure 19I:
Figure 19G:
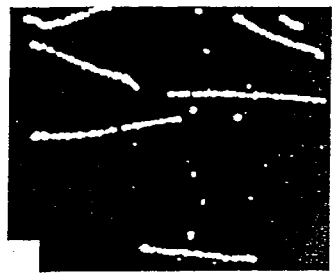
Figure 19F:
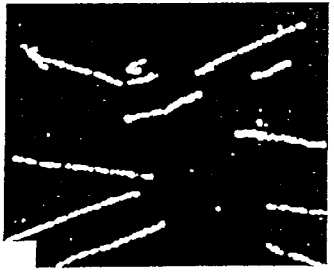
Figure 19E:

FIG. 16 is a schematic of nick translation and detection of surface mounted molecules. (a) Elongation and fixation of DNA molecules solution. A small droplet of DNA solution is deposited onto a clean glass slide. A modified glass surface is placed gently on top of the droplet and the DNA molecules elongate by the flow generated and adhere to the modified positively charged surface upon contact. This is then peeled off and air dried. (b) Addition of nick translation buffer: incorporation of labelled nucleotides commences. (c) After reaction, the surface is washed with TE and mounted onto a new microscope slide and imaged by fluorescence microscopy using a cooled digital CCD camera linked to a computer.

FIG. 17 is direct images of variously sized F-dUTP labelled PCR products. (A) 500 bp products with (dTTP)/(F-dUTP)=10/1. The average total number of fluorescent F-DUTP bases in each molecules was 20. DNA appears as "spots" since the contour length of 500 bp DNA is near the resolution of the optical microscope. (B) 2.8 kb product with (dTTP)/(F-dUTP)=10/1. (C) 5.3 kb product with (dTTP)/(F-dUTP)=5011. Assuming even incorporation of F-DUTP in most of the PCR products as reflected by (dTTP)/(F-dUTP) ratio as in the free solution, a single 500 bp DNA molecule with as few as 4 to 5 F-dUTPs is visible in our fluorescence detection system. Bar: 4 $\mu$m.

FIG. 18 is images of a series of 500 bp PCR products were made using different dTTP/F-dUTP ratios products: (A) 20, (B) 8.6, (C) 4.3, (D) 3, (E) 2, (F). 1, (G) 0.5 and (H) 0. Fluorescent beads (approximately three per imaging field) were used in the mounting solution to locate the plane of focus in dim images and were detected using a special filter set. Usually an image was taken using the bead filter set and then a new filter set was used to image the R110 labeled PCR products. The color of the beads was selected to prevent bleed-through, with the filter set designed for imaging PCR products (see section 10.1). (I) shows a typical area in an image containing beads. To confirm the existence of 500 bp DNA molecules in the sample used in (H), the same cover slip was then stained with YOYO-1 DNA staining dye and imaged again as shown in (J). DNA molecules were all detectable from (A)-(G) with decreasing fluorescence intensity (all images for R110-dUTP products were taken with 30 s image collection time on the cooled CCD camera.) In (G), an estimated half of the DNA products were not labelled with any detectable F-dUTP, which was consistent with the fact that the detectable signals were close to half that shown in (F).

FIG. 19 is the images of a surface nick translation time course. For FIGS. 19(A), (B), (C), (D), (E), (F), and (G), the surfaces were imaged after 0.5, 1, 2, 4, 8, 20.5 and 24 hours, respectively. (H) is the control surface incubated with the nick translation reaction solution without DNA polymerase I or DNAse I, but with the same concentration of fluorescence-dUTP. No signal was detected after overnight incubation. (J) is the control surface, which was the same surface shown in (A) but was removed from the slide and stained by YOYO-1 to confirm the presence of elongated and fixed DNA molecules. Bar: 4 μm.

Figure 20:
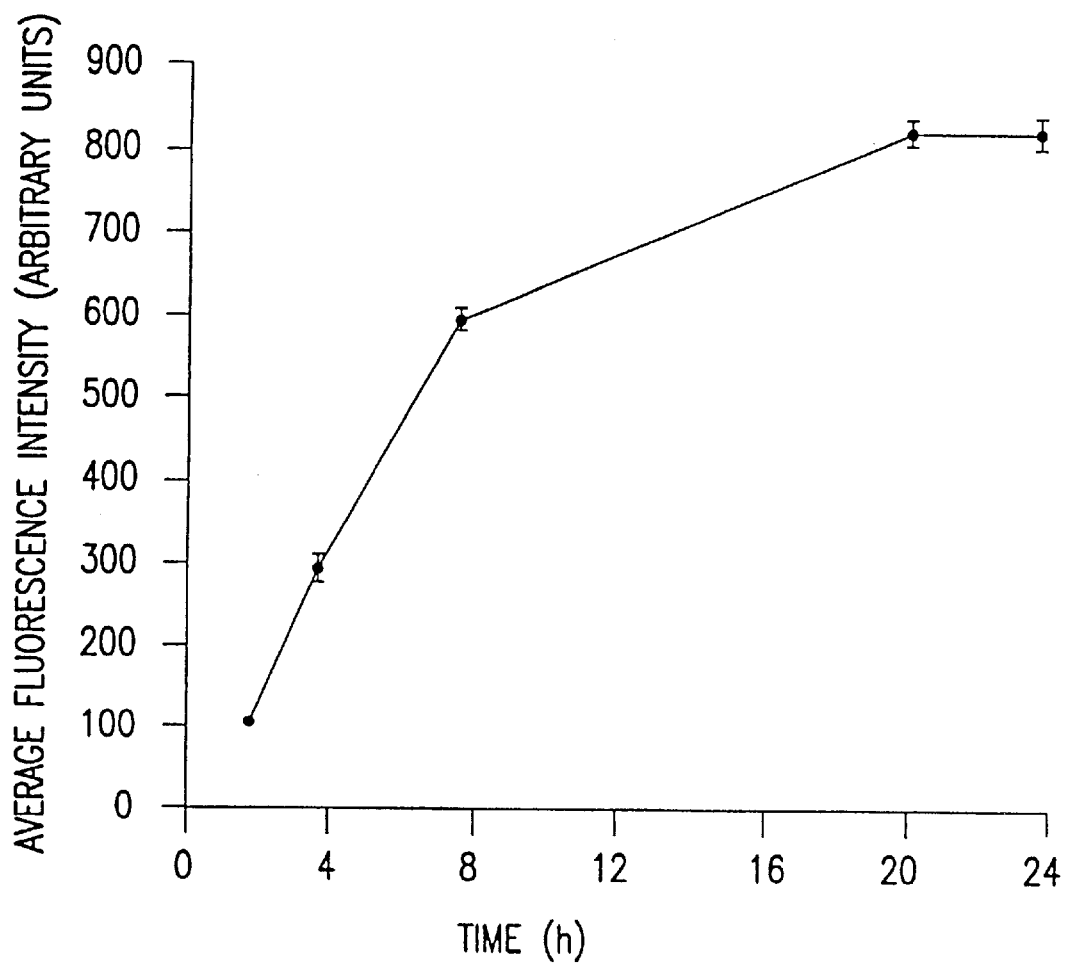

FIG. 20 is a plot showing how measured fluorescence intensity increases on labeled DNA molecules with time. Surface nick translation samples were imaged at different time points as shown in FIG. 19. The fluorescence intensity of the F-dUTP labeled DNA molecules were then measured using, on the average, 75 DNA molecules, from several separate images, to generate a single point on this plot. Error bars on the plot represent the 90% confidence on the calculated means. The net labeling of surface-fixed DNA with F-dUTP was rapid in the first 10 hours. After about 6 to 7 hours, DNA backbones were probably somewhat saturated by the F-dUTP incorporation, representing the equilibrium point at which DNA polymerase I incorporation of label reflected solution concentration levels, resulting in no net change in the total DNA fluorescence intensity.

FIGS. 21A, 21B, and 21C are photographs of an experiment demonstrating the localization of labeled RNA transcripts on DNA templates immobilized on an optical mapping surface FIG. 21D is a diagram of the 44 kb cosmid 380H5 that was used as the DNA template for the experiment illustrated in FIGS. 21A–21C.

FIGS. 22A, 22B, 22C, 22D, 22E, and 22F are photographs of an experiment illustrating that the RNA transcripts photographed in FIGS. 21A, 21B, and 21C are disrupted by digestion with Rnase.

FIGS. 23A, 23B, and 23D are photographs showing the in vitro transcription of whole E. coli genomic DNA using the method and device of the present invention.

FIG. 23C is a histogram depicting DNA molecule length (X-axis) versus arbitrary luminous intensity (Y-axis) for the photograph shown in FIG. 23A.

5. DETAILED DESCRIPTION OF THE INVENTION

The invention described in the subsections below encompasses methods and systems for optical sequencing of individual nucleic acid molecules performed by optically imaging a single labeled nucleotide or multiple labeled nucleotides on individual double stranded nucleic acid molecules. The methods and systems described herein can be utilized for optical sequencing purposes to generate accurate, rapid, high throughput analyses of nucleic acid molecules at the genome level. The invention also encompasses methods and systems for determining single nucleotide polymorphisms in a population of individual double stranded nucleic acid molecules. The invention further encompasses a method for imaging single or multiple labeled nucleotides on individual nucleic acid molecules. The invention also encompasses a novel method of analysis of a population of images using Bayesian estimation to determine the nucleotide sequence of the nucleic acid molecule in a statistically accurate manner.

The invention is also drawn to a method for analyzing nucleic acid reactions. Reactions that can be studied using the method include degradation reactions, such as enzymatic and chemical digestion; modification reactions, such as phosphorylation, glycosylation, and the like; transcription and reverse-transcription reactions, and translation reactions.

Section 5.1 sets forth the methods and systems of optical sequencing. In particular, Section 5.1.1 describes methods and systems for determining the nucleotide sequence of an individual double stranded nucleic acid molecule by nick translation and optical imaging of a single labeled nucleotide or multiple labeled nucleotides added to an individual double stranded nucleic acid molecule. The section includes a description of the biochemical scheme for optical sequencing and a description of the optical sequencing system. Section 5.1.1 also describes a simple instrument for optical sequencing.

Section 5.1.2 describes methods and systems for sequencing of individual nucleic acid molecules by primer extension. This section also describes templates and primers and assays for primer extension.

Section 5.2 describes methods for detecting and analyzing single nucleotide polymorphisms ("SNPs") of a population of individual double stranded nucleic acid molecules using the methods and system for determining the nucleotide sequence of individual double stranded nucleic acid molecules via primer extension.

The remaining sections set forth specific techniques such as techniques for elongating and fixing nucleic acid molecules on solid surfaces described in Section 5.3 and techniques for enzymatic nicking and addition of nucleotides described in Section 5.4. Section 5.5 describes labeled nucleotides that can be used in the present invention. Section 5.6 describes the imaging of single fluorescently labeled nucleotides. This section also includes, for example, descriptions of nucleic acid staining, microscopy and photography techniques useful for imaging single nucleic acid molecules. Section 5.7 describes modification of fluorescent labels by photobleaching and photolysis of the fluorescently labeled nucleotides.

Section 5.8 describes methods of analyzing images of labeled nucleotides on individual double stranded nucleic acid molecules by using Bayesian estimation for determining the location of the nucleotide sequence within the double stranded nucleic acid molecules.

Section 6 describes an efficient probablistic algorithm for making ordered restriction maps in which to align the nucleotide sequence.

Section 15 specifically describes a method for mapping transcription events. This section also includes Examples of the method being used to analyze transcription phenomena and correlate them to restriction sites, using whole genomic DNA as a template.

5.1. Single Molecule Optical Sequencing

The methods and systems of the present invention can be utilized to determine specific known and/or unknown nucleotide sequences present on surface-fixed individual nucleic acid molecules. These methods are referred to as "single molecule optical sequencing" methods and systems. Single molecule optical sequencing methods, in general, comprise the addition of labeled nucleotides to an elongated and surface-fixed individual double stranded nucleic acid molecule, which is then imaged and analyzed. The single or multiple labeled nucleotides are added, for example, by nick translation or primer extension methods as described in Sections 5.1.2. and 5.1.3, respectively.

Imaging of the labeled nucleotides is performed by a number of methods, for example, such as those described below in Section 5.6. The accuracy and position of the added labeled nucleotides can be identified, for example, using Bayesian estimation methods described in Sections 5.8 and 6.

The single molecule optical sequencing methods and systems of the present invention are unique in that they obtain sequence at the individual nucleic acid molecule level rather than from bulk analysis of a population of molecules. Therefore, the present methods and systems utilize much smaller amounts of samples of nucleic acid molecules than conventional methods.

The single molecule optical sequencing method and systems described herein have a variety of important applications. First, such methods can be used to generate complex physical maps of contiguous sequences by, for example, facilitating the alignment of nucleic acid molecules with overlapping nucleotides sequences such as Yeast Artificial Chromosomes (YACs) or Bacterial Artificial Chromosomes (BACs).

Second, such methods and systems make it possible to rapidly identify and locate specific genes of interest on individual nucleic acid molecules. For example, in instances where at least a portion of the nucleotide sequence of a gene is known, optical sequencing techniques can rapidly locate the specific genomic position of the gene using a primer and obtain the remaining sequence of the gene of interest.

Single molecule optical sequencing methods also make it possible to detect single nucleotide polymorphisms in a population of individual nucleic acid molecules, for example, by using the primer extension methods described below in Section 5.1.2.

Further, single molecule optical sequencing methods have numerous diagnostic applications, such as, for example, the rapid identification of nucleic acid molecules containing specific alleles, such as genetic disease-causing alleles. For example, individual elongated, fixed nucleic acid molecules from one or more individuals can be sequenced by primer extension using a primer which is specific for (i.e., will specifically hybridize to) an allele of interest. Such an allele may, for example, be a disease-causing allele. The presence of a particular sequence, as evidenced by the addition of one or more particular labeled nucleotides, would indicate that the individual from whom the nucleic acid sample was taken contains the allele of interest. Alternatively, the presence of a particular allele is detected by the presence or absence of a primer extension product produced, for example, by a polymerase in the presence of at least one labeled nucleotide.

5.1.1. Methods and Systems for Sequencing Individual Nucleic Acid Molecules via Nick Translation Methods and systems for optically determining the nucleotide sequence of an individual double stranded nucleic acid molecule of the present invention use nick translation, optical imaging, and analysis of the images to obtain the nucleotide sequence.

Briefly, the optical sequencing methods and systems are based on imaging a single labeled nucleotide on an individual double stranded nucleic acid molecule, comprising the steps of nicking a double stranded nucleic acid molecule elongated and fixed onto a surface so that the double stranded nucleic acid molecule remains accessible for enzymatic reactions with enzymes for the addition of a single labeled nucleotide; enzymatically adding a single nucleotide comprising a label; and imaging the added label, as described in greater detail below.

Elongating and fixing the individual double stranded nucleic acid molecules to a solid surface can be accomplished by a number of methods as described below in Section 5.3. In a preferred embodiment, the solid surface is a planar surface. In another embodiment, the solid surface is derivatized according to methods known in the art to assist in the fixation of the nucleic acid molecules as described below in Sections 5.3.2.1.–5.3.2.3. In a specific embodiment, the solid surface is glass, which is derivatized with silane compounds, such as, but not limited to, 3-aminopropyltriethoxysilane (APTES); 3-methylaminosilane; [3-triethoxysilyl-propyl] trimethylammonium chloride (TESP); or N,N,N-trimethyltrimethoxylsilypropylamino chloride (TSPAC).

A preferred method of elongation and fixation of the nucleic acid molecules is the "fluid-fixation" technique, in which the droplets of liquid containing the individual nucleic acid molecules are spotted onto derivatized surfaces and allowed to air dry (see Sections 5.3.3. and 8.1.2 for detailed descriptions). For example, DNA molecules can be elongated and fixed in square arrays by spotting droplets of DNA solution onto derivatized glass surfaces through a glass capillary tube or stainless steel capillary pipetting tool using a micro-manipulator in combination with an x-y table controlled by microstepper motors.

In one embodiment, the surface-fixed individual double stranded nucleic acid molecule is nicked by any methods known to one of skill in the art, such as chemically nicking but preferably by using an enzyme. In a more preferred embodiment of the present invention, the nicking is performed using the enzyme DNase I. The number of nicks can be varied by methods known to those skilled in the art, for example, but not intended as a limitation, the enzyme concentration can be varied or by varying the amount of incubation (see Section 5.4 for a discussion of enzymes and optimization of reaction conditions).

By way of example and not limitation, the distribution of nick sites will be adjusted to space them approximately 5 times the resolution of light microscopy, or approximately 1 to 2 microns (3–6 kb of B-DNA, assuming nearly complete elongation: 70–90% of the calculated polymer contour length).

In a preferred embodiment, the DNase treatment is followed by a wash to terminate activity. In a more specific embodiment, the wash comprises a proteinase K/detergent treatment or heat, followed by additional washes.

Next, a single labeled nucleotide is added to the nicked site. In a preferred embodiment, the nucleotides comprising a label, are fluorescently labeled. For example, fluorescent labels that can be used are fluorescein, or other fluorescent dyes known in the art or developed in the future, and most preferably, rhodamine, cyanine, and pyrene. (See Section 5.5 for a detailed description of the labeled nucleotides). In a preferred embodiment, a polymerase and fluorescently labeled nucleotides of one type of base (e.g., $A^f$) are added onto the solid phase support with the fixed nucleic acid molecules in standard buffers known to those skilled in the art.

Several different polymerases are suitable for use in the optical sequencing methods. The criteria for selection includes: ability to efficiently incorporate fluorochrome labeled nucleotides, lack of 3'-5' exonuclease activity (or its suppression) fidelity of template-directed addition, and good activity with surface-mounted molecules. Illustrative examples of polymerases that may be used, are, without limitation, T7 Sequenase v. 2.0, *E. coli* DNA Polymerase I, the Klenow Fragment of DNA polymerase I lacking the 3'-5' exonuclease activity, T7 Sequenase v. 2.0 and Taq Polymerase (see Section 5.4, for a description of the enzymatic activities and assays of polymerases for use in the present invention). In another embodiment, the 5'-3' exonuclease activity is suppressed by addition of nucleotide monophosphates to the reaction. The polymerases in this proposed set contain different strengths and weaknesses in terms of fidelity, tolerance to labeled nucleotides, capacity for strand displacement, and 5'-3' exonuclease activity (See Section 5.4 for a detailed description of the enzymes for use in optical sequencing).

The single labeled nucleotide is then imaged using techniques known to those of skill in the art. In one embodiment of the present invention, the labeled nucleotide is imaged using a fluorescent microscope, a camera and a source of illumination. In other preferred embodiments, the step of imaging the label is performed using a camera and a microscope. In a further embodiment, the step of imaging the label further comprises using laser illumination. In yet another preferred embodiment, the step of imaging further comprises using a computer. See Section 5.6 for a detailed discussion of imaging techniques.

By way of example, and not limitation, the elongated and fixed double stranded nucleic acid molecule is illuminated, preferably with a laser. The molecule can be imaged through a fluorescent microscope (such as a Zeiss Axiovert 135-TV) which is manually or automatically focused. The laser beam is focused through a ground glass rotating wheel, and the scattered light is delivered to the microscope to reduce interference effects. The image from the microscope is put through a series of filters and collected using a camera such as a cooled CCD camera.

Additionally, the nucleic acid molecules can be imaged using an integrated microscope control, and examined using machine vision, and statistical analysis system or Optical Mapping Method (OMM) as described in Section 6 and 7.1. for constructing a map of the nucleic acid molecules after optical sequencing and/or digestion with restriction endonucleases.

The optical images of the added labeled nucleotide can be examined using a variety of computer based techniques written by any one skilled in the art. By way of example, and not limitation, the images are examined using software such as, NIH Image or IPLab (Signal Analytics). A nonlinear least squares analysis can be performed, for example, using MATHEMATICA™ (Wolfram Research). Images can also be analyzed by cross correlation analysis to the expected Gaussian profile and Gaussian smoothing followed by peak finding. Background noise levels can be reduced if desired by adjusting the settings of the camera or modifying and/or averaging image processing.

In a preferred embodiment, the images of the labeled nucleotides are analyzed using Bayesian estimation to determine the reliability of the label additions and to determine the position of the nucleotide sequence in relation to the double stranded nucleic acid molecule backbone. Descriptions of the Bayesian estimation and analysis of the nucleotide sequence are in Sections 5.8 and 6.

A method for imaging single labeled nucleotides can be applied to imaging multiple labeled nucleotides and for determining the nucleotide sequence of an individual double stranded nucleic acid molecule, which method comprises the steps of: nicking a double stranded nucleic acid molecule elongated and fixed onto a surface so that the nucleic acid molecule remains accessible for enzymatic reactions with enzymes for the addition of labeled nucleotides creating a nicked strand; displacing the nicked strand or opening the nicked sites on the nucleic acid molecule; adding a nucleotide comprising a label to the nicked site; imaging the added label; modifying the label in order to visualize subsequently added labels; and repeating the above steps a desired number of times to determine the nucleotide sequence of the nucleic acid molecule. The method can further comprise analyzing the images using Bayesian estimation.

More particularly, a biochemical scheme for optical sequencing by nick translation is set forth in FIG. 1 and is as follows: first, an individual double stranded nucleic acid molecule is elongated and fixed to a solid surface, most preferably using fluid fixation techniques described in Section 5.3.3. The elongated and surface-fixed double stranded nucleic acid molecules are nicked, preferably using an enzyme, for example, a DNase (as described above).

In one embodiment, the nicked sites are opened to produce gaps for the addition of more than one labeled nucleotide. In a preferred embodiment, the step of opening the nicked site on the nucleic acid molecule is performed by an enzyme having 5'-3' exonuclease activity. In a specific embodiment, the enzyme having 5'-3' exonuclease activity is DNA Polymerase I, the Klenow fragment of DNA Polymerase I, or T7 exonuclease gene 6. The amount of gap producing activity can be optimized and controlled according to methods known to those skilled in the art, such as those discussed in Section 5.4.

In another embodiment, the method for determining the sequence of a nucleic acid molecule adds additional labeled nucleotides by displacing the nicked strand. In a preferred embodiment, the nicked strand is displaced enzymatically by the Klenow fragment of DNA Polymerase.

The addition of labeled nucleotides is preferably performed using fluorescently labeled nucleotides, for example, with fluorochromes known to those skilled in the art as described above. Most preferably, the fluorescent label is rhodamine. The labeled nucleotides can be added using methods known to those skilled in the art, preferably using a polymerase, as described above.

In another preferred embodiment, the steps of opening the nicked sites on the double stranded nucleic acid molecule and adding a nucleotide comprising a label is performed by T7 exonuclease gene 6 and T7 Sequenase v. 2.0, respectively.

After the addition of one or more fluorescently labeled nucleotides, the label or labels are imaged using techniques known in the art, preferably using fluorescence microscopy as described above and in Section 5.6.

Once a label is imaged, the label can be modified to allow imaging of subsequently added labeled nucleotides. In a preferred embodiment, the label is a fluorescent label, which is photolabile, and the fluorochrome is modified by photobleaching or photolysis (see Section 5.7 for a detailed discussion).

In a preferred embodiment, the elongated and fixed nucleic acid molecules are overlayed with a solution of 20–30% β-mercaptoethanol before imaging to attenuate photobleaching.

In another embodiment, the method for imaging a single labeled nucleotide can also be used to simultaneously image multiple labeled nucleotides by utilizing nucleotides comprising differently labeled bases so that the different bases are distinguishable when imaged. For example, the nucleotides comprise at least four bases (i.e., A, C, G, and T) and at least four fluorochromes that are imaged at different wavelengths (see Section 5.5 for description of labeled nucleotides useful in the present invention). For example, the different fluorescent labels are differentiated according to the wavelengths of light which causes the fluorochromes to fluoresce. The added labeled nucleotides are imaged at their respective required wavelengths of light, analyzed, and the types of nucleotide bases are identified according to the different fluorescence image. In this embodiment, the labels are modified by illuminating the fluorochromes at different wavelengths of light. Different fluorochromes will have different spectral characteristics that are readily measured.

Illustrative examples of imaging labeled nucleotides added to individual double stranded nucleic acid molecules and determining the sequence of the nucleic acid molecules via nick translation are described in Sections 7 and 8.

System for Optical Sequencing by Nick Translation

A system for determining the nucleotide sequence of an individual double stranded nucleic acid molecule, comprises the elements, as described above and in the referenced sections, of: a double stranded nucleic acid molecule elongated and fixed onto a surface so that the nucleic acid molecule remains accessible for enzymatic reactions and/or hybridization reactions; a polymerase included on the surface; nucleotides comprising a label included on the surface; and a device for imaging the label to produce an image.

In one embodiment of the invention, the system further comprises a nucleic acid nicking enzyme, preferably, the nucleic acid nicking enzyme is a DNase, more preferably DNase I.

In another preferred embodiment, the system further comprises a nick opening enzyme, preferably the nick opening enzyme is T7 exonuclease gene 6, DNA Polymerase I, the Klenow fragment of DNA Polymerase I or a 5'-3' exonuclease.

In yet another preferred embodiment, the polymerase is DNA Polymerase I, the Klenow fragment of DNA Polymerase I without the 5'-3' exonuclease activity T7 Sequenase v. 2.0, or Taq polymerase.

In another embodiment, the label on the nucleotide is a fluorescent label.

In another embodiment, the device for imaging comprises a fluorescence microscope, a camera and a source of illumination. In a more preferred embodiment, the source of illumination is a laser. In yet another preferred embodiment, the device for imaging comprises a computer.

In a further embodiment, the device for imaging the label processes the image using Bayesian estimation as described in detail in Sections 5.8 and 6.

Figure 2:
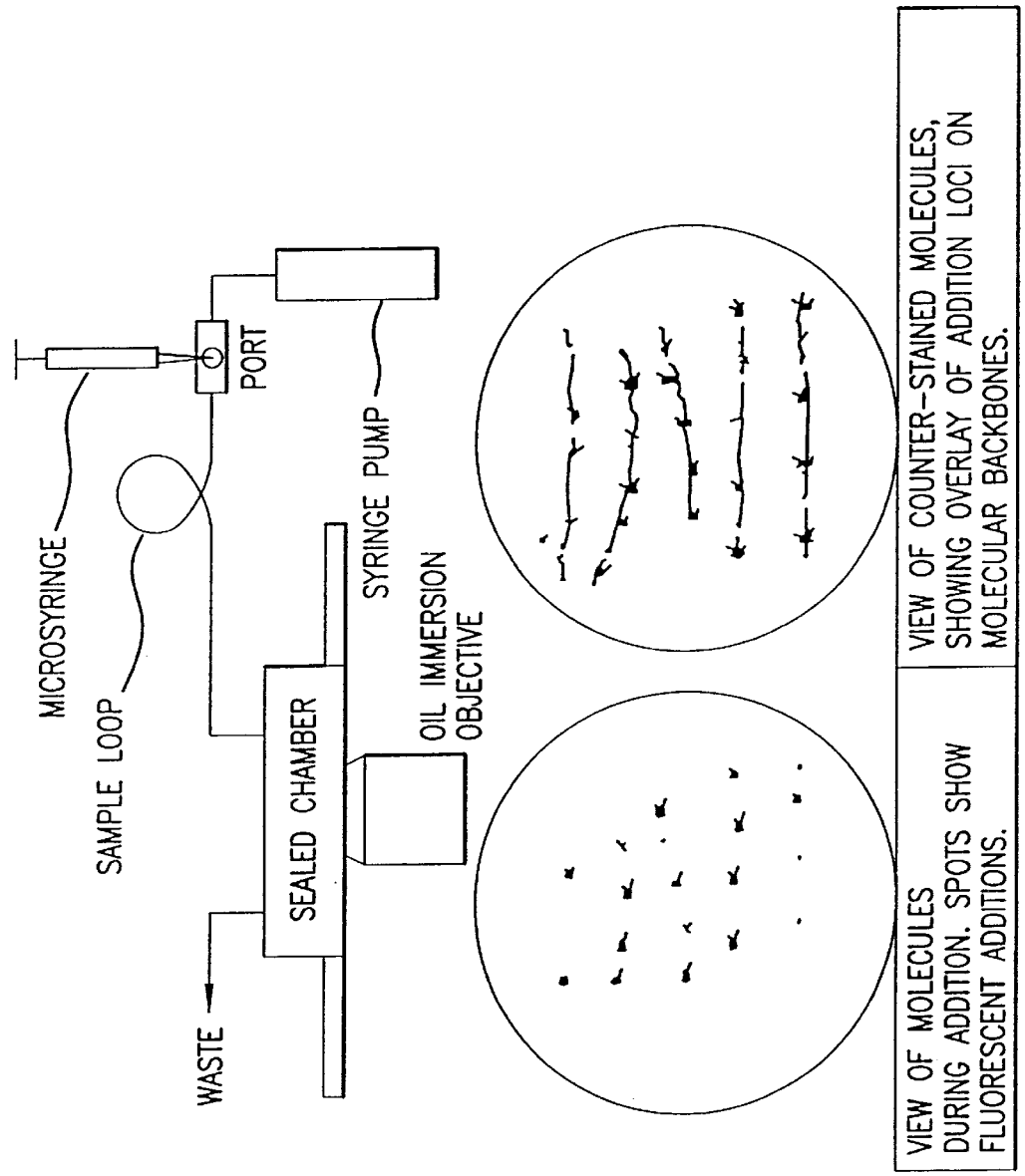
FIG. 2 is a diagram of the components for a simple, unautomated Optical Sequencing System.

By way of illustration, FIG. 2 sets forth a diagram of a simple unautomated instrument for optical sequencing. By way of example, and not limitation, an optical sequencing system comprises a microscope mounted, sealed chamber connected to a syringe pump with an in-line reagent injection port. The nucleotides, polymerase and other reagents are loaded into the sample loop through the injection port. Reagents are stored and injected from separate syringes. The syringe pump can deliver reagents injected into the loop, to the chamber, or deliver buffers for washing between reaction steps.

The sample to be sequenced is first mounted onto a solid surface by the methods described in Section 5.3. Next, the surface is placed in the "sealed chamber", which is constructed of TEFLON™ and having a gasketed metal flanges to firmly secure the surface during fluid injection. The temperature control can be accomplished by methods known in the art, for example, by jacketing the apparatus with feeds from an external waterbath. To prevent motion of the surface during reagent loadings, which may destroy image registration, minimal pressures will be employed during deliveries and washes.

In another embodiment of the invention, the system is automated by methods known to one skilled in the art, for example, by incorporating solenoid driven valving devices and the like.

An illustrative example of an optical sequencing system is described in Section 12.

5.1.2. Methods and Systems for Sequencing of Individual Nucleic Acid Molecules via Primer Extension Sequencing of individual nucleic acid molecules can also be accomplished using methods and systems using primer extension techniques.

The primer extension methods utilize elongated and fixed individual nucleic acid template molecules annealed with at least one primer onto a surface, such as a solid surface, so that the nucleic acid molecule remains accessible for enzymatic reactions with enzymes for the addition of labeled nucleotides, according to the procedures described in Section 5.3. Alternatively, the individual nucleic acid template molecules can first be elongated and fixed to a surface and then annealed to one or more primers.

The template nucleic acid molecules can be isolated from any source by methods known to those skilled in the art. The nucleic acid molecules can be single or double stranded nucleic acid molecules. The primers are obtained or made by methods known in the art. For example, the primers are 18 to 20 nucleotides complementary to sequences known on the template nucleic acid molecule, or random sequences.

The elongated and fixed nucleic acid molecule and at least one annealed primer are exposed to a polymerase and to nucleotides including a nucleotide comprising a label to produce a labeled primer extension nucleic acid molecule. In particular, the polymerase enzymes useful in the present invention are, for example, DNA Polymerase I, the Klenow fragment of DNA Polymerase I lacking the 5'-3' exonuclease activity, Taq polymerase, or T7 Sequenase v. 2.0 as described in Section 5.4.

The labeled primer extension nucleic acid molecule is imaged according to techniques known in the art and as described in Section 5.6. In a preferred embodiment, the labeled primer extension nucleic acid molecules are imaged using fluorescent microscopy and a camera. Additionally, the primer extension nucleic acid molecule is illuminated with a laser.

In another embodiment of the present invention, the method of determining the nucleotide sequence of an individual nucleic acid molecule comprises (a) exposing a nucleic acid molecule annealed with at least one primer elongated and fixed onto a surface so that the nucleic acid molecule remains accessible for enzymatic reactions with enzymes for the addition of a labeled nucleotide to a polymerase and nucleotides comprising a base and a label; and (b) imaging the labeled nucleotide added onto the primers.

The nucleotide sequence is determined by the detection of the addition of the labeled nucleotide. The nucleic acid molecule and primer are exposed sequentially to different labeled nucleotide bases (e.g., A,T,G,C) until an addition is observed. Alternatively, the nucleic acid molecules annealed with at least one primer are elongated and fixed to at least four solid surfaces and a different nucleotide base (e.g. A,T,G,C) is added to each solid surface with a polymerase.

The solid surface exposed to a known labeled nucleotide base, which results in an imaged labeled addition corresponds to the nucleotide sequence at the 3' end of the primer.

In another embodiment of the present invention, a method of determining the nucleotide sequence of an individual nucleic acid molecule comprises exposing a nucleic acid molecule annealed with at least one primer elongated and fixed onto a surface so that the nucleic acid molecule remains accessible for the addition of labeled nucleotides to a polymerase and dideoxy nucleotides comprising a base and a label. In preferred embodiments, the elongation and fixation techniques, polymerases and labeled nucleotides described above are used.

Next, the labeled dideoxy nucleotide added onto the primer is imaged using techniques known in the art and described in Section 5.6; and the image is analyzed using Bayesian estimation to determine the nucleotide sequence of the nucleic acid molecule by the addition of the labeled dideoxy nucleotide.

In another embodiment, a method of determining the nucleotide sequence of an individual nucleic acid molecule comprises: exposing a nucleic acid molecule annealed with at least one primer elongated and fixed onto a surface so that the nucleic acid molecule remains accessible for enzymatic reactions with enzymes for the addition of labeled nucleotides to a polymerase and dideoxy nucleotides; exposing the nucleic acid molecule annealed with at least one primer to a polymerase and nucleotides including nucleotides comprising a label to produce a labeled primer extension nucleic acid molecule; and imaging the labeled primer extension nucleic acid molecule to produce an image to determine the nucleotide sequence of the nucleic acid molecule by the absence of a primer extension product and corresponding to the dideoxy nucleotides used. In another embodiment of this method, the nucleic acid molecule is first elongated and fixed onto a planar surface and is then annealed to at least one primer.

The techniques and methods known in the art and described above and in Sections 5.3–6 are used for the above methods.

An illustrative example of optical sequencing via primer extension is described in Section 13.

System of Optical Sequencing by Primer Extension

A system for determining the nucleotide sequence of an individual nucleic acid molecule, comprises the elements of: an elongated and fixed nucleic acid molecule on a surface so that the nucleic acid molecules remain accessible for enzymatic reactions with enzymes for the addition of labeled nucleotides; at least one primer annealed to the nucleic acid molecule; a polymerase enzyme included on the surface to produce a primer extension product; dideoxy nucleotides included on the surface; nucleotides comprising a label included on the surface; a device for imaging the elongated and fixed nucleic acid molecule to detect the presence of labeled nucleotides in the primer extension product to produce an image whereby the absence of the image of the primer extension product for a particular dideoxy nucleotide corresponds to the nucleotide sequence at one position of the nucleic acid molecule.

By way of example, and not limited to, a simple system for determining the nucleotide sequence of individual nucleic acid molecules comprises nucleic acid molecules spotted onto four optical mapping surfaces, in register; labeled dideoxy nucleotide (e.g., A,T,G,C) and a polymerase. Optical detection of the added labeled dideoxy nucleotide on one of the four corresponding surfaces indicates the nucleotide sequence at that position on the nucleic acid molecule.

5.2. Optical Detection of Single Nucleotide Polymorphisms (SNP)

Single nucleotide polymorphisms ("SNPs") are nucleotide sequence variants, which are of predictive value in identifying many genetic diseases that are often caused by a limited number of different mutations in a population. In spite of the paucity of scorable phenotypes, SNPs are found in large numbers throughout the human genome (Cooper et al., 1985, Hum. Genet. 69:201–205), and a large portion of which form disease causing mutations, for example, heritable breast cancer (Cannon-Albright et al., 1996, Sem. Oncol. 23:1–5).

Many of the techniques available for the detection of SNPs involve complex chemical/biochemical procedures, such as template-directed primer extension (Syvanen, 1994, Clinica Chimica Acta 226:225–236; Nikiforov et al., 1994, Nucleic Acids Res. 22:4167–4176) or ligation-based analysis (Nickerson et al., 1990, Proc. Natl. Acad. Sci. USA 87:8923–8927; and Samiotaki et al., 1994, Genomics 20:238–242). The latest Affymetrix-brand "chip" (Chee et al., 1996, Science 274:610–614) is dramatically effective, but is still a very specialized approach. The "TaqMan" scheme which utilizes the 5'-3' exonuclease activity of Taq polymerase to cleave a double fluorescently labeled primer (Livak et al., 1995, Nature Genet. 9:341–342; and Livak et al., 1995, PCR Methods and Applications 4:357–362) offers a potentially very high throughput but is limited in terms of potential multiplexing by the variety of "color" scenarios that can be developed and rapidly detected.

Standard approaches of bulk-sample measurements must generally rely on simple measurements of populations (i.e., of tagged molecules) that are, by definition, averaged together. The bulk-sample measurements must use discrimination or filtering techniques that approximate the labeled loci. Multiplexing techniques, utilizing fluorochrome reporters with differing spectral characteristics, may enhance discrimination and throughput.

A distinct advantage of single molecule over bulk-sample techniques is that averages of measurements can be readily formed after a series of sophisticated filtering techniques. For example, individual molecules can be automatically selected by machine-vision techniques on the basis of length, location of annealed probes, or overall fluorescence intensity. Large numbers of measurements, suitably filtered and binned, yield accurate, reliable determinations. Given the advancements in computer hardware and imaging techniques, the time overhead required to essentially analyze samples "one molecule at a time" is not significantly more time consuming than conventional approaches. Multiplexing techniques combined with single molecule approaches increase throughput. An advantage of imaging single molecules is that one can simultaneously investigate numerous loci on the same molecule.

5.2.1. Methods of Optical SNP Detection

The present invention describes methods to detect a single nucleotide difference or polymorphism in a population of individual double stranded nucleic acid molecules such as a nucleotide change that is often the cause of an inheritable genetic disease. To discern the identity of the immediate nucleotide incorporated on the 3' end of at least one annealed probe, a dideoxyribonucleotide is tested for incorporation by subsequent template-directed extension with dNTPs that include some fluorescently labeled nucleotides (i.e., fluorochrome labeled dUTP). If a particular dideoxy nucleotide is incorporated, subsequent extension is excluded and no signal is detected from the failure for primer extension to occur. If the dideoxy nucleotide does not add, then subsequent labeled nucleotide addition in the primer extension product is detected, and evidences the lack of dideoxy nucleotide incorporation. By running four parallel addition tests, the identity of all four bases is determined and cross-checked. An intriguing feature of Optical SNP Detection is its capability for simple multiplexed measurements. Multiple loci on long-range PCR products can be simultaneously assayed by their location relative to a marked molecular end.

In an embodiment of the present invention, the method for determining single nucleotide polymorphisms comprises the following steps as set forth in FIG. 3. First, an individual or a population of individual nucleic acid molecules are elongated and fixed to a solid surface. The nucleic acid molecules themselves and/or long-range PCR products are conventionally used. At least one probe or primer is annealed to the surface-fixed nucleic acid molecules using standard annealing conditions known to those skilled in the art. For example, the probes are annealed to the nucleic acid molecules using high temperature PCR-like conditions (see Section 8).

The probe hybridization conditions are never ideal. Probes can hybridize to multiple sites unless conditions are carefully controlled to take into account probe composition and overall stringency. High stringency conditions known to those skilled in the art can be used to control the specificity of hybridization of the probes (Sanbrook et al, 1989, *Molecular Cloning: A Laboratory Manual*, Cold Spring Harbor Laboratory Press, Plainview, N.Y. for teachings on hybridization conditions for high, medium and low stringency). A chosen base of dideoxy nucleotides (e.g., ddATP) is added to the solid surface with a polymerase, preferably Taq polymerase. SNP detection can take several forms depending upon prior knowledge of the mutation, and the desire for a positive or confirmatory negative results. For example, if the mutation involves an A-to-G transition (on the template strand), then a dideoxy nucleotide could be selected for non-addition to a mutant template but addition to the wild type template or exclusion of the three other bases. Heterozygosity in the population of individual nucleic acid molecules is determined by the proportion of subsequently labeled loci in the primer extension step.

Primer extension with fluorescently labeled nucleotides is performed by adding fluorochrome labeled nucleotides (commercially available) with a polymerase to the solid surface-fixed nucleic acid molecules. Primer extension only occurs if the dideoxy nucleotides did not add in the previous step. Primer extension occurs when the selected dideoxy nucleotide base and template are mismatched.

The amount of primer extension desired is determined by the amount of labeled nucleotides required for reliable detection and the use of multiple primers must be spaced far enough to allow for dependable resolution. In a preferred embodiment of the invention, under light microscopy, the practical resolution is approximately 1–2 microns, or about 3 to 6 kb. In another preferred embodiment, using CCD imaging system, 15 to 30 pixels are resolved, depending upon the magnification.

The individual or population of individual nucleic acid molecules are imaged as described below in Section 5.6. The images are analyzed according to the Bayesian estimation described below in Section 6. In a particular embodiment, the error analysis for the Bayesian estimation method can be based on the assumptions of missed hybridization sites, hybridization to incorrect sites, failure of dideoxy nucleotides to incorporate correctly, and faulty primer extension reactions—both positive and negative.

5.2.2. A System for Optical SNP Detection

The present invention also describes a system for determining the nucleotide sequence of an individual nucleic acid molecule, comprising an elongated and fixed nucleic acid molecule on a surface so that the nucleic acid molecules remain accessible for enzymatic reactions with enzymes for the addition of labeled nucleotides; at least one primer is annealed to the nucleic acid molecule; a polymerase enzyme included on the surface to produce a primer extension product; dideoxy nucleotides included on the surface; nucleotides comprising a label included on the surface; a device for imaging the elongated and fixed nucleic acid molecule to detect the presence of labeled nucleotides in the primer extension product to produce an image; and a method of processing the image using Bayesian estimation to detect the presence of a primer extension product; whereby the absence of the image of the primer extension product for a particular dideoxy nucleotide corresponds to the nucleotide sequence at one position of the nucleic acid molecule.

A system for determining a single nucleotide polymorphism in a population of nucleic acid molecules, comprises nucleic acid molecules which are elongated and fixed onto four surfaces and the surfaces are individually exposed to a different dideoxynucleotide bases.

Figure 4:
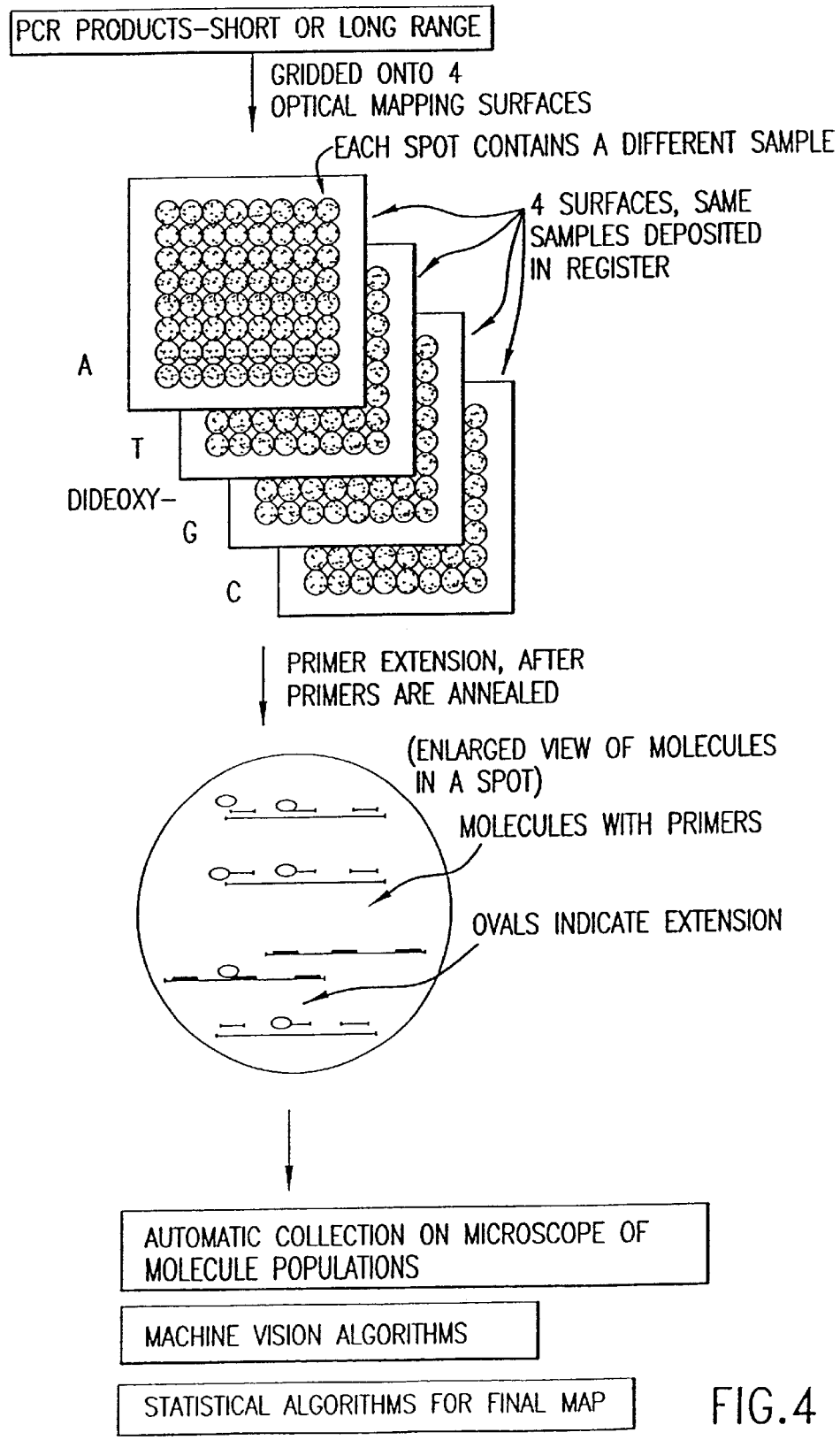
FIG. 4 is an illustration of the scheme of the Optical SNP Detection system.

In a particular embodiment, the system for Optical SNP detection is set forth in FIG. 4. Samples to be analyzed can consist of short or long-range PCR products. The samples are placed in microtiter plates, 81–100 in number, are gridded by a laboratory spotting engine onto four solid-surfaces in register. Such spotting engines are known in the art and commercially available (for example the Beckman Biomek 2000). Fiduciary marks are applied to maintain orientation. The spotted surfaces are overlayed with acrylamide; each is treated with a different base of dideoxy nucleotides and Taq polymerase. After reaction, the surfaces are washed to remove excess unincorporated material. A mixture of dNTPs, including a fluorochrome labeled nucleotides, and Taq polymerase is added, and primer extension occurs at sites lacking added dideoxy nucleotides. The surfaces are then mounted on an automatic imaging microscope coupled to a computer assisted optical imaging system. The images are analyzed using Bayesian estimation methods to select molecules and notes sites of primer extension. A map of primer extension sites consistent with the data set, is produced to determine the type and extent of the single nucleotide polymorphisms in the population of individual nucleic acid molecules.

By means of example, and not limitation, an example of optical SNP detection is described in Section 14.

5.3. Single Nucleic Acid Molecule Elongation Techniques

A variety of solid surface-based techniques can be utilized for the rapid, controllable and reproducible elongation and fixation of single nucleic acid molecules in such a manner that allows rapid, efficient analysis and/or manipulation of the molecules. As described in this section, the preferable technique is fluid-fixation described below in Section 5.3.3.

Solid surface-based elongation/fixation techniques yield a number of advantages for single nucleic acid analysis/ manipulation applications. For example, the nucleic acid molecule images are very sharp and bright. Additionally, fixation techniques can be more precisely controlled and may, for example, be made somewhat tighter than gel-based techniques. Thus, the solid surface-based techniques described herein make possible the rapid generation of high resolution nucleic acid analysis information from single nucleic acid molecules, including single nucleic acid molecules of much shorter lengths than currently available using gel-based techniques. The techniques of the present invention also utilize smaller amounts of reagents and enzymes than standard methods.

For the present invention, elongation and fixation of double stranded nucleic acid molecules can be accomplished using any solid surface-based methods known to those of skill in the art so that the double stranded nucleic acid molecule remains accessible for enzymatic reactions with enzymes for the addition of labeled nucleotides. In a preferred embodiment, the nucleic acid molecules are fluid-fixed to a solid surface as described below.

A wide size range of nucleic acid molecules, i.e., from about 300 bp to mammalian chromosome-size (that is greater than 1000 kb) can efficiently be elongated and stably fixed onto the solid surfaces described herein. These techniques feature gentle fixation approaches, which maintain the biological function of the nucleic acid molecules being elongated and, further, allow for the manipulation and/or accurate analysis of the elongated single nucleic acid molecules. Additionally, the solid surface-based techniques described herein make possible the storage and reuse of the elongated nucleic acid molecules. Further, such solid surface-based techniques described herein can easily be adapted for high throughput methods, as described in Section 5.6, below.

The elongation procedures described in this Section utilize solid surfaces that exhibit a positive charge density, as described, below, in Section 5.3.2. As discussed below, in Section 5.3.2., however, the density of the solid surface positive charge must be optimized to achieve a balance between elongation, relaxation, stability and biological activity parameters.

5.3.1. Solid Surface Optimization

Unlike instances in the past in which nucleic acid molecules were attached to solid surfaces, the controlled, reproducible solid surface elongation/fixation techniques described herein utilize surfaces, especially glass surfaces, which reproducibly elongate and fix single nucleic acid molecules. As discussed in greater detail below, in Section 5.3.2., the surfaces described herein exhibit a positive charge density. Several parameters must be taken into account, however, in order to optimize the solid surface charge density such that, for example, the genome analysis techniques described, below, in Sections 5.8 and 6, can be performed.

The solid surfaces of the invention should exhibit a positive charge density which achieves an optimal balance between several parameters, including elongation, relaxation, stability and biological activity. Assays are described in this Section which make surface optimization possible.

First, the solid surface must allow the molecule to be as completely elongated as possible, while allowing for a small degree of relaxation. As used herein, "small degree of relaxation" refers to a level of relaxation which yields a gap of between about 0.5 microns and about 5.0 microns when the elongated nucleic acid molecule is cut. An optimal balance between these two parameters yields improved imaging capability. For example, an efficient balance between elongation and relaxation capability facilitates the imaging of newly formed, growing gaps as develop at restriction enzyme cleavage sites.

In addition to elongation and relaxation, the biological activity retained by the elongated nucleic acid molecule must be taken into account when optimizing the positive charge density of the elongation/fixation solid surface. Further, the stability of the elongated nucleic acid molecules on the surface must be considered. In the case of a restriction digest (i.e., as part of an optical mapping procedure), "stability" refers to how well the restriction fragments formed are retained on the solid surface.

As a first step toward determining the positive charge density which represents an optimal balance between each of these parameters, the positive charge density (e.g., the level of surface derivatization; see Section 5.1.2, above) may be titrated against the measured average molecular length of the nucleic acid molecules which are deposited on the surface. Molecule counts (i.e., the number of countable molecules which have been deposited) on the surface can also be measured.

At low levels of positive charge density (e.g., derivatization), the average molecular extension on the surface is low. This may be due to the fact that, at this charge concentration, not enough nucleic acid binding sites exist to hold an extended molecule with stability. As the positive charge density (e.g., the level of derivatization) increases, the average nucleic acid molecular extension also increases, eventually peaking. As the positive charge density (e.g., the amount of derivatization) continues to further increase, the average amount of molecular extension then begins to decrease. This may be due to the presence of such an abundance of nucleic acid binding sites that any flow forces which are present and would drive elongation are overwhelmed and, therefore, molecular extension is, to some extent, quenched.

Once a positive charge density (e.g., a derivatization level) is achieved which affords maximum nucleic acid molecule extension, the elongation parameters must be tested within the context of the specific imaging or analysis procedure for which the single molecules are to be used. Such testing involves an evaluation of the biological activity of the nucleic acid molecule as well as a determination of the relaxation level of the elongation nucleic acid. For example, in instances whereby the elongated nucleic acid molecules are to be used for optical restriction mapping, the level of elongation/fixation must allow for cutting by the restriction enzyme as well as providing a level of relaxation which makes possible the ready imaging of nascent restriction enzyme cleavage sites.

In the case of optical mapping, one such test would include the digestion of the elongated nucleic acid molecule and a determination of first, the enzyme's cutting efficiency, and, second, a measurement of the size of the nascent gap formed at the new cleavage sites (thus measuring relaxation). A cutting efficiency of at least about 50% is an acceptable level of biological activity retention. Acceptable relaxation levels are as described above.

Further, the stability of the elongated nucleic acid molecule must be ascertained. As discussed above, in the case of optical mapping, stability refers to the retention level of newly formed restriction fragments on the surface. For optical mapping, an acceptable stability level is one in which at least about 80% of the newly formed restriction fragments is retained.

5.3.2. Solid Surface Positive Charge Density

Solid surfaces may be prepared for optimal elongation and fixation of single nucleic acid molecules via a variety of simple manipulations. First, for example, the surfaces may be derivatized to yield a positive charge density, which can be optimized by utilizing the assays described in Section 5.3.1., above. Preferably, the charge density should be proportional to the amount of derivatization. Additionally, simple manipulations may be performed to reversibly modulate the surface positive charge density to more precisely optimize surface charge density at each step of the nucleic acid elongation, fixation analysis and/or manipulation steps. Such reversible charge density modulation is referred to herein as "facultative fixation", as discussed below. Third, additional methods for further affecting the elongation/fixation of the single nucleic acid molecules are discussed. These include, for example, methods for controlled drying, for the generation of gradients of positive charge density and for crosslinking of the elongated nucleic acid molecules.

5.3.2.1. Surface Derivatization

Surfaces may be derivatized using any procedure which creates a positive charge density which, presumably, favors an interaction with a nucleic acid molecule. Any compound which absorbs to or covalently binds the surface of interest and, further, introduces a positive charge density onto the surface can be utilized as a derivatizing agent. Such compounds should not, preferably fluoresce.

For example, surfaces may be derivatized with amino moiety-containing compounds that absorb to or covalently bind the surface of interest. Such amino-containing compounds can, for example, include amino-containing silane compounds, which are capable of covalently binding to surfaces such as glass. Among these amino-containing silane compounds are 3-aminopropyltriethoxysilane (APTES) 3-methylaminosilane. APTES can be useful in that it may be crosslinked (see below, e.g.), while the use of 3-methylaminosilane may, in certain instance, be advantageous in that the compound resists oxidation.

Among those derivatizing agents which non-covalently absorb to surfaces, such as glass surfaces may, for example, be derivatized with poly-D-lysine (polylysine). Polylysine binds glass via electrostatic interactions. When utilizing polylysine as a derivatizing agent, the size of the polymeric polylysine is to be taken into account. For example, low molecular weight polylysine (e.g., mw less than 200,000; with about 90,000 being preferred) appears to fix elongated nucleic acids more tightly than high molecular weight polylysine (e.g., mw greater than 200,000, with 500,000 being preferred). Thus, when elongating and fixating on a solid surface which having polylysine, a low molecular weight polylysine would be preferred for tighter fixation, e.g., for the fixation of smaller nucleic acid fragments.

Surface derivatization may be achieved by utilizing simple, reproducible techniques. When derivatizing a surface with APTES, for example, a clean surface, such as a glass surface, may be incubated in an acidic APTES solution for a given period of time. Increasing the incubation time will increase the resulting charge density of the surface. It is preferred that conditions should be chosen such that the single nucleic acid molecules are elongated to approximately 50–100% of their polymer contour length.

In one embodiment of such an APTES derivatization procedure, a clean glass surface can be incubated for an appropriate period of time in an APTES concentration of about 0.10 M, pH 3.5 at a temperature of about 65° C. Incubation times for such an embodiment can range from about 3 to about 18 hours. In order to stop the derivatization process, the surfaces need only be removed from the APTES solution and repeatedly rinsed in highly pure water. Clean, derivatized coverslips are then air dried.

With respect to derivatizing a surface with polylysine, a clean surface, such as a glass surface, can be derivatized in a polylysine solution. The concentration and molecular weight of the polylysine used for derivatization affect the level of derivatization achieved per incubation time. Increasing the polylysine concentration increases the resulting surface charge density which forms. For optical mapping purposes, conditions should be chosen such that single nucleic acid molecules are extended up to about 100% of their polymer contour length.

In one embodiment of such a polylysine derivatization method, a clean glass surface can be incubated overnight, at room temperature, in a solution of polylysine having a molecular weight of about 350,000, at a concentration of about $10^{-6}$ to $10^{-7}$ grams per milliliter. After incubation, the derivatized glass surface is rinsed in highly pure water and either air dried or wiped dry with lens tissue paper. Such conditions are expected to achieve nucleic acid elongation levels which are suitable for, say, optical restriction mapping.

In addition to methods which involve the use of a derivatizing agent such as described above, a positive charge density may be introduced onto a surface by a number of alternate means. Such a positive charge density may, for example successfully be applied to a surface via plasma derivatization, an electrostatic generator (to create electrical charge) or corona discharge, just to name a few.

5.3.2.2. Facultative Fixation

Described herein are methods for the reversible modulation of solid surface positive charge density. Such methods are designed to optimize solid surface charge density at each step of the elongation, fixation and analysis/manipulation steps described herein. Among the ways by which such a reversible charge density can be effected include changes in the salt concentration, divalent cation concentration, effective water concentration, and/or pH.

Using facultative fixation, the surface positive charge density can be tailored to suit each step of the single nucleic acid techniques described herein. For example, it may be desirable to fix the nucleic acid molecule under reversible conditions which favor a loose charge density, leading to a higher degree of nucleic acid molecule spreading. The charge density may then, for example, be increased for a restriction digest step. Additionally, it may be desirable to digest a molecule so tightly fixed that no relaxation gaps form upon cleavage and then to subsequently lower the charge density such that the gaps are allowed to form. Finally, a very high charge density may then be chosen if the sample is to be stored (i.e., such that the newly formed restriction fragments do not detach from the surface during storage).

With respect to salt concentration, as the salt concentration the surface finds itself in increases (e.g., from 0 to 5M NaCl), the surface positive charge density decreases. With respect to divalent cation (e.g., $Mg^{2+}$, $Ca^{2+}$) concentration, as the divalent cation concentration in the buffer surrounding the surface increases (e.g., 1 mM to 1M), the surface positive charge density decreases. As the effective water concentration is decreased, due to the addition of an increasing concentration of non-aqueous material, the surface positive charge density increases.

Changing the pH represents a gentle and fast method to reversibly modulate the charge density of a surface. A low pH promotes positively charged environment, while a high pH promotes a less positively charged, more neutral environment.

Taking, as an example, a surface which has been derivatized using an amino-containing group, an aminosilane compound, for example, a pH of approximately 6 yields a positive charge density. Raising the pH lowers the charge density until the charge is essentially neutral at a pH of 9–10. A variety of simple methods may be utilized to produce pH-based facultative fixation. For example, the surface can be exposed to buffers, such as Tris or phosphate buffers, of varying pH. Additionally, gas-induced pH changes can be made. For example, $CO_2$ gas can be introduced over the buffer in which the derivatized surface is submerged such that the buffer is acidified, thereby increasing the overall charge density on the surface. Alternatively ammonia gas, for example, may be introduced over the buffer, raising the buffer pH, thereby lowering the overall surface charge density. These latter gas-based techniques are especially useful in instances whereby it is essential to minimize possible physical disturbances on the solid surface in that the buffer remains undisturbed throughout the facultative fixation process.

5.3.2.3. Other Positive Charge Density Methods

Derivatization Gradients. In addition to a uniform, controllable derivatization of an entire solid surface, it is also possible to reproducibly form a gradient of derivatization. Such a derivatization gradient can be formed by, for example, the use of drops of derivatizing agents deposited on the solid surface. Upon deposition, such a drop would form a meniscus, leading to a greater concentration of derivatizing agent available to the solid surface at the perimeter of the drop than within its interior section. This, in turn, leads to a gradient of derivatization, with the outer portion of the solid surface where the drop had been exhibiting a higher level of derivatization than that within the interior.

Such a gradient of derivatization promotes a higher percentage of fully elongated molecules. Further, due to the tension set up across the nucleic acid molecule, a more efficient level of aligning and packing is observed, thus maximizing the amount of usable molecules per imaging field, one goal of invention.

Crosslinking. The single elongated nucleic acid molecules of the invention may, additionally, be crosslinked to the solid surface. Such crosslinking serves to permanently fix the molecules to the surface, which can be advantageous for a variety of reasons. For example, crosslinking may be useful when working with very large nucleic acid molecules. Further, the surface properties of the solid may be modulated with no possibility of nucleic acid loss. Additionally, the possibility of unacceptable nucleic acid fragment loss or relaxation which could occur over the course of, for example, storage or a long reaction, would not exist with crosslinking.

Crosslinking, as utilized herein, is to be performed in conjunction with the elongation/fixation techniques described in these Sections. First, the desired level of elongation is determined and achieved, and subsequent to this, the elongated nucleic acid is crosslinked for permanent fixation.

A number of crosslinking methods are available, including glutaraldehyde and UV crosslinking. Glutaraldehyde crosslinking may be performed using, for example, via 5 minute incubation in a 10 mM glutaraldehyde solution. UV crosslinking may be accomplished using, for example, a Stratalinker (Stratagene) crosslinker, following standard protocols.

Controlled Drying. Additional compounds may be added to the aqueous solution by which the nucleic acids may be deposited onto the solid surfaces (see below for deposition techniques) which yield drying characteristics that promote the production of a greater percentage of fully elongated nucleic acid molecules and which exhibit a lower level of intermolecular overlap or tangling, both features of which are extremely useful for analysis purposes.

Compounds which may be added for such a controlled drying aspect of the elongation methods include, but are not limited to glycerol, DMSO, alcohols, sucrose, neutral polymers such as Ficoll, and dextran sulfate. While their mechanism is not known, it is possible that these compounds promote a liquid crystalline state which promotes the above-described features.

Hydrophobic Microwells. Hydrophobic regions may be introduced onto portions of the solid surfaces which can serve as, essentially, "microwells". These hydrophobic regions create closed boundaries, which make possible the introduction of different reagents onto different portions of the solid surface, such that a number of different reactions may be performed simultaneously on the same solid surface.

Prefixation Techniques. The solid surfaces of the invention may, be prefixed with agents, proteins for example, of interest, prior to the introduction of the nucleic acid molecules to be elongated. Proteins may be fixed onto the solid surfaces by routine means, such as crosslinking means, which are well known to the skilled artisan. Among the proteins which may be prefixed onto the solid surfaces of the invention are enzymes, such as restriction enzymes, which are used to manipulate nucleic acid molecules or any other nucleic acid-binding proteins. Thus, upon elongation of nucleic acid molecules onto the solid surfaces containing such prefixed enzymes and the addition of whatever additional agents, such as certain divalent ions, which are necessary for the enzymes to act upon nucleic acids, the single nucleic acid molecules can be manipulated, for example, cleaved at appropriate restriction sites. Using such a prefixation technique, a number of different reactions may be performed simultaneously on the same surface.

5.3.3. Single Nucleic Acid Molecule Deposition

As described above, a wide size range of nucleic acid molecules may be deposited onto the derivatized solid surfaces described herein. Specifically, nucleic acid molecules from about 300 base pairs to greater than 1000 kb can be analyzed using such solid surfaces. Smaller nucleic acid molecules, which are relatively shear resistant, can be isolated using standard nucleic acid purification techniques well known to those of skill in the art. These smaller nucleic acid molecules may be less than about 150 kb and, generally, are less than about 20 kb.

Larger nucleic acid molecules, which are subject to breakage by shearing events, can be isolated by utilizing nucleic acid molecule isolation techniques known in the art. Such shear-sensitive nucleic acid molecules are generally greater than 150 kb, but may include molecules greater than about 20 kb.

Such methods for large nucleic acid molecule isolation include, for example, agarose-embedded cell lysate techniques as described in U.S. Pat. No. 4,695,548 (incorporated herein by reference). Briefly, cells are washed, mixed with molten low melt agarose, which is then allowed to set. The resulting block is placed in a lysis solution containing EDTA, protease, and detergent which diffuses into the block, lysing the cells and rendering intact naked DNA molecules stripped of their associated proteins. The absence of physical manipulation keeps the DNA essentially intact. The agarose can then melted and the DNA can be subjected to elongation and fixation techniques. Alternatively, chromosomal DNA can first be resolved into chromosomal populations via standard methods such as, for example, pulse field electrophoresis.

Additionally, a condensation agent is used to collapse gel-bound nucleic acid molecules into small, shear-resistant balls, that can be unfolded with the addition of an ionic compound, such as, for example, sodium chloride or magnesium chloride, where appropriate. Preferably, the condensation agent is spermine as described in U.S. Pat. No. 5,720,928(incorporated herein by reference). While spermine is preferred, other suitable materials for collapsing such nucleic acid molecules include any material or condensation agent which can cause a particular nucleic acid molecule to collapse, e.g., any condensation agent which causes nucleic acid molecules to preferentially solvate themselves. Additional examples of such materials include, but are not limited to, spermidine, alcohol and hexamine cobalt.

Larger nucleic acid molecules (i.e., those greater than about 90 kb) should, generally, be deposited onto the solid surfaces in a manner which minimizes breakage due to shear forces. Preferably, therefore, the nucleic acid molecules deposited in such an aqueous fashion can be elongated by merely allowing the aqueous solution to dry. Thus, in the absence of any manipulations apart from simple deposition onto a derivatized surface of the invention, single nucleic acid molecules can efficiently, successfully and rapidly generate stably elongated and fixed nucleic acid molecules suitable for imaging and/or further manipulation. As described, below, in Section 5.6, such a technique is especially suited to high throughput analysis techniques.

As described previously, elongated and fixed DNA molecules (2–1,500 kb) using the flow and adhesion forces generated when a fluid sample is compressed between two glass surfaces, one derivatized with polylysine or APTES (Meng et al, 1995, Nature Genet. 9:432–438; and Cai et al., 1995, Proc. Natl. Acad. Sci. USA 92:5164–5168) (see also U.S. Pat. No. 5,720,928, incorporated herein by reference). Fixed molecules were digested with restriction endonucleases, fluorescently stained with YOYO-1 (oxazole yellow dimer) (Rye et al., 1992, Nucleic Acids Res. 20:2803–2812) and optically mapped (Meng et al, 1995, Nature Genet. 9:432–438; and Cai et al., 1995, Proc. Natl. Acad. Sci. USA 92:5164–5168). To increase the throughput and versatility of optical mapping, multiple samples need to be arrayed on a single mapping surface. Although robotic gridding techniques for DNA samples exist (Heller et al., 1997, Proc. Natl. Acad. Sci. USA 94:2150–2155; Craig et al., 1990, Nucleic Acids Res. 18:2653–2660; and Nizetic et al., 1991, Proc. Natl. Acad. Sci. USA 88:3233–3237), such approaches were not designed to work with single molecule substrates and could not be relied upon to deposit molecules retaining significant accessibility to enzymatic action.

To examine molecular effects that would ensure a usable population of elongated molecules, we have investigated several new approaches to molecular deposition based on placing small droplets of DNA solution onto critically derivatized glass surfaces. A new macromolecular effect which readily elongates and fixes DNA molecules was discovered and characterized and named "fluid fixation".

Fluid fixation uses the flows developed within a drying droplet through evaporative means to elongate and fix DNA molecules to charged surfaces. Conveniently, application of outside forces are completely obviated, making use of electrical fields, a travelling meniscus (Michalet et al., 1997, Science 277:1518) or end-tethering of molecules with beads (Strick et al., 1996, Science 271:1835–1837) unnecessary. The passive nature of fluid fixation provides the platform needed for our efforts to automate optical mapping. In addition, biochemical versatility of fluid fixed molecules is demonstrated by the imaging of DNA polymerase I action on these substrates.

Given the ability to grid multiple samples, and assay biochemistries on the single molecular level, an integrated system has been developed to robotically deposit samples, and image substrate molecules using automated fluorescence microscopy.

In general, fluid fixation of nucleic acid molecules is performed by spotting droplets of liquid containing the nucleic acid molecules onto derivatized surfaces and allowing the droplets to dry.

In a preferred embodiment, double stranded nucleic acid molecules are elongated, aligned and fixed by spotting droplets of DNA solution onto derivatized glass surfaces using a glass capillary tube (500 $\mu$m, i.d.) or cut-off stainless steel syringe needle to draw DNA samples and then spot them onto the derivatized glass surfaces by simple contact. In one embodiment, the droplets were 10–20 nL and contained 5–50 ng/$\mu$l of DNA in Tris-DETA buffer). The capillary tube or needle is operated using an Eppendorf micromanipulator in combination with an x-y table (interfaced with a computer) controlled by a microstepper motor. Preferably, the spots are 500–1000 $\mu$m in diameter. More preferably, the spots are 500–900 $\mu$m, and most preferably 900 $\mu$m±100 $\mu$m. The samples are allowed to air dry.

In a more preferred embodiment, addition of either glycerol or other polyalcohol "dopants" to the spotting solutions maximizes the elongation and alignment of the nucleic acid molecules and minimizes overlapping (see FIG. 12).

By way of example and not limitation, a method for fluid fixation of DNA is described in Section 7.1.

5.4. Enzymes for use In Nicking and Nucleotide Addition

The methods of imaging a labeled nucleotide may utilize enzymes for the nicking the individual double stranded nucleic acid molecules, opening the nicked sites and for the addition of labeled nucleotides.

In one embodiment of the invention, the nicking step of the method for imaging the addition of a single labeled nucleotide is performed by the enzyme DNase I. *E. coli* DNase I nicks DNA in the presence of $Mg^{+2}$ (Clark et al., 1972, Biochem. 13:5098–5102; and Laskowski, 1971, "Deoxyribonuclease I" in *The Enzymes*, vol. 4, Boyer (ed.), pp. 289–311), an activity easily modulated by DNase concentration or time. The level of DNase I action must be controlled so as to obtain nick sites that are spaced far enough apart on the average to minimize optically coincident addition sites—thereby enabling imaging of discrete, non-coincident sites. One skilled in the art is able to use known experimental methods to maximize the number of addition sites on a molecule for high throughput.

Assays for DNase I activity can be used by one of skill in the art to optimize the amount of nicking of the surface-fixed double stranded nucleic acid molecule. For example, varying the concentration of the enzyme and time of incubation, buffer composition, and surface conditions and analyzing the resulting nicks by the machine vision/analysis system as described in Section 6 to accumulate large numbers (1,000–10,000) of molecule samples and construct histograms from these measurements to show nicking activity. From such analysis, one can determine the optimum conditions. Since nick translation activity is sequence-context dependent, conditions should be selected to minimize such sequence-context dependent activity.

In another preferred embodiment, the nicked site of the double stranded nucleic acid molecule is opened using T7exonuclease gene 6. T7 exonuclease gene 6 acts by a distributive mechanism at nick sites and double-stranded ends (Engler et al., 1983, J. Biol. Chem. 258:11197–11205; and Kerr et al., 1972, J. Biol. Chem. 247:311–318). This enzyme is used to open nicked sites to generate gapped duplexes as substrates for Sequenase and for Klenow polymerases, and is used to create gaps of about 20 to 40 nucleotides. The formation of excessively large gaps could lead to double-strand breaks, especially if nick sites on opposite strands are near each other.

Gapping activity is assayed by treating surface-mounted molecules with DNase I followed by T7 exonuclease and then tabulating the cut sites. One skilled in the art knows to use optimized DNase concentration before treating with T7 exonuclease.

One skilled in the art would be able to optimize conditions for using T7 exonuclease gene 6 to obtain optimal nicking for Optical Sequencing. By way of example, and not limitation parallel experiments are run to estimate gap size and the incidence of double stranded breaks. To estimate the average gap sizes, T7 exonuclease reactions are run using lambda DNA or cosmid DNA in varying conditions, then incorporating radiolabeled nucleotides with Sequenase, and followed by denaturing gel electrophoresis (generating fragment sizes amenable to standard sequence gels). A "spectrum" of additions is observed. Further, a phosphor imager can be used to quantitate yields. In a parallel experiment, agarose gels are run to determine the extent of double stranded breaks.

In another embodiment, addition of a single or multiple labeled nucleotides is performed by a polymerase.

In preferred embodiments of the present invention, the polymerase is DNA Polymerase I, the Klenow fragment of DNA Polymerase I lacking the 5'-3' exonuclease activity, T7 Sequenase v. 2.0 or Taq polymerase. Additionally, 5'-3' exonuclease activity can be suppressed by the addition of nucleotide monophosphates.

DNA Polymerase I has been used in nick translation reactions of DNA molecules deposited onto Optical Mapping surfaces (New England Biolabs, Beverly, Mass.) (see Section 6). Polymerase I vigorously incorporates pure, fluorochrome labeled nucleotides (no unlabeled nucleotides are required for addition). The enzyme's 5'-3' exonuclease activity provides a convenient route for simple incorporation of labeled nucleotides at nick sites and obviates the need for gap formation on native target DNA.

However, the 3'-5' proof reading ability may cause problems. When a single nucleotide is added in the presence of DNA polymerase I, there is the opportunity for exonuclease activity to remove nucleotides or "chew back" beyond the nascent addition site, obviously destroying any chance for sequence determination. This activity is suppressed when a nucleotide matching the template strand is included (Brutlag et al., 1972, J. Biol. Chem. 247:241–248; and Kornberg, 1992, DNA Replication 2nd ed., W.H. Freeman & Co., New York). However, at any given time in the Optical Sequencing cycles, there can be up to three other non-matching, and thus vulnerable bases exposed in template strands (see FIG. 1, describing the chemistry of optical sequencing). Addition of all four nucleotides would confound this method for Optical Sequencing.

There are several strategies for suppressing the 3'-5' exonuclease activity known to those of skill in the art such as: high nucleoside monophosphate concentration to compete against the nascent strand for the 3'-5' exonuclease binding site (Kornberg, 1992, DNA Replication 2nd. ed, W.H. Freeman & Co., New York), maintaining a low temperature to minimize frayed ends (16° C., or perhaps below; balancing enzyme activity), or using an exo-mutant. Another approach is to use primer extension reactions instead of nick translation (see Section 5.2 Optical SNP detection).

In a more preferred embodiment the Klenow fragment, also available with ablated proofreading activity is used in the present invention (Bebenek et al., 1990, J. Biol. Chem. 265:13878–13887). The reason to use primer extension is that all templates are the same; other valid reasons for this approach will be discussed in another section. Nucleoside monophosphate does suppress proofreading, but it is not sufficiently reliable for Optical Sequencing.

Another embodiment of the present invention uses the Klenow fragment of DNA Polymerase I which is commercially available as a 3'-5' exonuclease(–) mutant (Amersham). Compared to polymerase I, the lack of proofreading is a distinct advantage for reasons described above. However, lack of 5'-3' exonuclease activity can cause problems of template switching during strand displacement or diminished activity on adsorbed molecules. Lack of proofreading also affects addition fidelity, although this problem can be minimized by limiting the number of additions to, perhaps, no more than 20 nucleotides.

Klenow activity on solid surface mounted nucleic acid molecules can be assayed using methods commonly known to those skilled in the art. By means of example and not limitation, Klenow nucleotide incorporation activity can be measured by generating nicks in the surface-mounted double stranded nucleic acid molecules using T7 exonuclease gene 6 (as discussed above and in Section 7) and then adding either mixtures of fluorochrome labeled and unlabeled nucleotides or only labeled nucleotides. The rates of fluorochrome incorporation (in terms of sites and amounts) will be determined by constructing histograms of images containing 1,000–10,000 molecule-substrates as functions of time, temperature, surface variables and buffer conditions.

Primer extension assays known to those skilled in the art can also be utilized to determine the ability of Klenow or DNA Polymerase I to enzymatically act on surface-mounted molecules within a sterically confined environment. For example, by changing buffer pH or salt concentration (within a range of enzyme functionality), electrostatic forces responsible for molecular adhesion to the surface can be altered. The protonization of the amine groups on the surface reduces effective charge, and increasing salt concentration reduces effective charge on both surface-bound amines and DNA molecules.

Another preferred embodiment of the present inventions utilizes the polymerase, T7 Sequenase v. 2.0 (Amersham) which lacks a 5'-3' or 3'-5' exonuclease activity, but, unlike Polymerase I, its action is processive. Also, this enzyme does not exhibit strand displacement activity.

In a preferred embodiment, the T7 exonuclease gene product 6 (from Amersham) is used to create small gapped duplexes at nick sites which is followed by use of the T7 Sequenase v. 2.0 for incorporation of labeled nucleotides.

5.5. Labeled Nucleotides

Numerous labeled nucleotide molecules are commercially available for use in the present invention. In a preferred embodiment of the invention fluorescently labeled nucleotides are used. By way of example, and not limitation, the present invention uses nucleotides labeled with fluorescein, rhodamine, cyanine or pyrene. These fluorochromes, as well as a host of others are available commercially from Molecular Probes, Inc., Eugene, Oreg. Particularly suitable and commercially-available fluorochromes from Molecular Probes include 6-(((4-(4,4-difluoro-5-(2-thienyl)-4-bora-3a, 4a-diaza-s-indac ene-3-yl)phenoxy)acetyl) amino)hexanoic acid, succinimidyl ester ("BODIPY TR"), 6-((4,4-difluoro-1,3-dimethyl-5-(4-methoxyphenyl)-4-bora-3a,4a-diaza-s-indacene-2-propionyl ) amino) hexanoic acid, succinimidyl ester (BODIPY TMR), and cyanine-based dyes such as "YOYO"-brand dyes, available commercially from Molecular Probes, Eugene, Oreg.

In a more preferred embodiment, Perkin Elmer ("PE") Applied Biosystems fluorescent dNTPs have been used successfully in nick translation experiments for several years. PE offers two nucleotides, dUTP and dCTP, each conjugated with three different rhodamine fluorochromes, R110, R6G, and TAMRA. These nucleotide derivatives were originally developed for incorporation at high yields in PCR reactions, to be analyzed by automated gel electrophoresis. In many ways, our application is actually less demanding than PCR amplification, since the template strands remain the same throughout the Optical Sequencing reaction cycles.

The chemical and optical features of these nucleotides make them ideal for Optical Sequencing: high incorporation yields by different polymerases (Taq DNA polymerase or other thermostable DNA polymerases, DNA polymerase I (Perkin-Elmer Applied Biosystems, [F] dNTP Reagents, Protocol 402774, 1996), or Sequenase (Amershan)) good fluorescence yields, and the availability of three different fluorochromes for conjugation, providing a route for multiplexing.

The fluorochrome should ideally (1) conjugate to nucleotides but not hinder the action of polymerase enzymatic action and activity, (2) the fluorochrome should also emit sufficient numbers of photons to provide an image, and (3) be capable of photobleaching.

5.6. Imaging

The single or multiple labeled nucleotides added to the individual double stranded nucleic acid molecules of the present invention can be imaged via a number of techniques to generate a digital image of the label which can be processed to obtain quantitative measurements of molecular parameters of interest. For example, single fluorochromes can be observed using video rate imaging techniques known to those skilled in the art (see Schmidt et al. 1996, Proc. Natl. Acad. Sci. USA 93: 2926–2929).

In one embodiment, the individual nucleic acid molecules containing the labeled nucleotides are imaged through a fluorescent microscope with a camera and illuminated with a light source. In a particular embodiment, the standard fluorescent microscope is a Zeiss Axiovert 135, ×100 Plan neofluar objective. In other embodiments, the camera is a cooled CCD camera or an Intensified Silicon Target (ISIT) cooled CCD camera. Additionally, a silicon intensified target (SIT) camera is used for focusing.

Additionally, the nucleic acid molecules mounted on a surface are covered with 45% β-mercaptoethanol with 1 mM YOYO-3 when R110-dUTP is used and 20–30% β-mercaptoethanol with 1 mM YOYO-1 in Tris-EDTA buffer when R6G-dUTP is used as an anti-photobleaching reagent to improve the fluorochrome photobleaching half-lives by as much as 500 fold.

The elongated and fixed nucleic acid molecules with labeled nucleotides can be illuminated with an appropriate light source known in the art. By way of example and not limitation, the light source is a laser. More particularly, the laser is an $Ar^+$ laser.

Further, an additional aspect of the invention entails imaging the individual nucleic acid molecules in order to map the locations of the added labeled nucleotides within the individual nucleic acid molecule.

The elongated, fixed single nucleic acid molecules of the invention are also imaged via a number of techniques to generate a digital image of the molecule which can be processed to obtain quantitative measurements of molecular parameters of interest. To this end, in a preferred embodiment of the present invention, the molecules being imaged are stained with fluorochromes which are absorbed by the molecules generally in proportion to their size. Accordingly, the size of the stained molecules can later be determined from measurements of the fluorescent intensity of the molecule which is illuminated with an appropriate light source, as known in the art. (see U.S. Pat. No. 5,720,928; Cai et al., 1995, Proc. Natl. Acad. Sci. USA 5164–5168; and Meng et al., 1995, Nature Genet. 9:432–438; which are incorporated herein by reference).

A preferred embodiment of the present invention is to first image the incorporated fluorescently labeled nucleotides and then to counterstain the individual double stranded nucleic acid molecules to image the molecule so as to map the sites of additions of labeled nucleotides. Counterstains available are known to those skilled in the art and are, for example but not limited to, YOYO-1, YOYO-3, etc. An illustrative example of correlation of signals with molecular backbones is described in Section 12.1.3.

5.7. Modifying Nucleotide Labels

In the present invention, after the labeled nucleotides have been imaged and quantitated, the label may be modified or removed to facilitate imaging of subsequently added labeled nucleotides. For example, when fluorescently labeled nucleotides are used, the fluorochrome can be modified by photobleaching or removed by photolysis.

Photolysis is the cleavage of one or more covalent bonds in a molecular entity resulting from absorption of energy from light or other electromagnetic radiation. Photolytic destruction of fluorochromes moieties, without significant damage to the nucleotide, is one method to eliminating potential problems with consecutive addition of labeled nucleotides and known in the art (Praseuth et al., 1988, Biochem. 27:3031–3038; Shoikhet et al., 1991, Nucleic Acids Res. 24:248; and Benimetskaya et al., 1989, Biopolymers 28:1129–1147).

Photobleaching is the loss of color or fluorescence through the action of incident visible or near-ultraviolet radiation. Photobleaching after the addition and imaging of the labeled nucleotide is to eliminate any fluorescence signals between cycles. Photobleaching can also used to partially eliminate bulky fluorochrome moieties after they have served their purpose. Such action may further facilitate labeled nucleotide additions. One advantage of using this process is that it is non-enzymatic, works in virtually any buffer and does not require addition or subtraction of reagents. Nascent fluorochrome labeled additions are photobleached by simply timing our imaging to assure complete photobleaching as verified by imaging. Remaining, or unaccounted for, signals eliminate the chance to discriminate new additions. Photobleaching to completion is easily achieved since the time required is also quite short and, therefore, damage to the template strands is minimized.

5.8. Analysis of Digital Images

The present invention also entails methods of analyzing the images of the labeled nucleotides in order to correlate them with the backbone of the double stranded nucleic acid molecule to locate the addition of the single or multiple labeled nucleotides and to obtain the nucleotide sequence of nucleic acid molecule. The method of analysis is also used to obtain the location and identification of a single nucleotide polymorphisms of a population of individual nucleic acid molecules. Methods of analyzing images of signals from labeled molecules and correlating them to a position known in the art can be used in the present invention.

Figure 5:
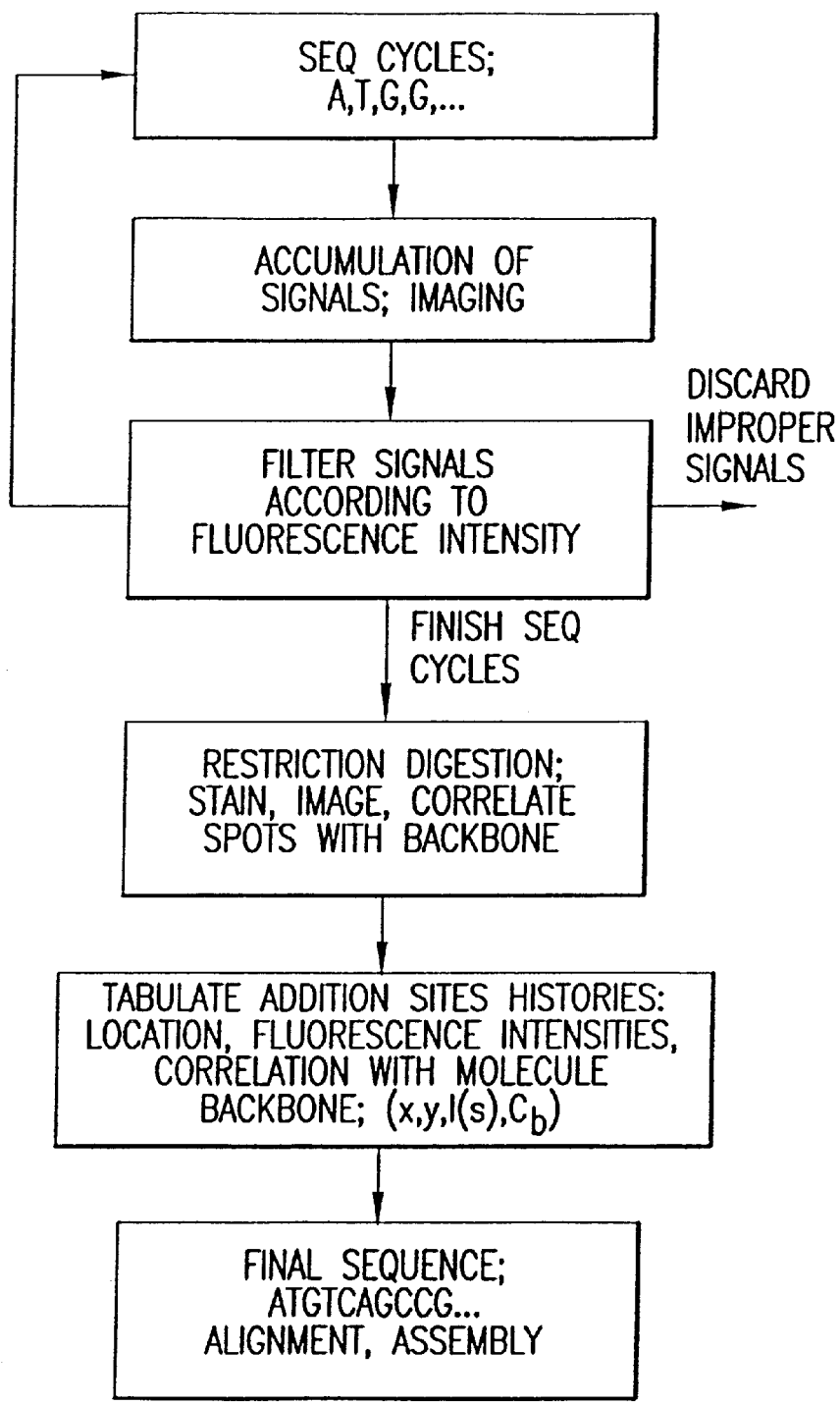
FIG. 5 is a block diagram of the analysis scheme for Optical Sequencing which shows how imaged fluorescent additions will be analyzed by position, fluorescence intensity, and correlation with molecules in the imaged field.

In a preferred embodiment, the present invention analyzes the images from the fluorescently labeled nucleotides to correlate them with the double stranded nucleic acid molecules mounted on the solid surfaces to determine the location of the added labeled nucleotides and, thus, determine the nucleotide sequence of the molecules. The present invention discloses a novel method of analysis utilizing Bayesian estimation to correlate the images of the added labeled nucleotides with the nucleic acid molecular backbone. The analysis scheme for imaging and optical sequence is set forth in FIG. 5.

Specifically, the method of analyzing the images using Bayesian estimation, comprises the steps of:

(a) accumulating signals of an addition site of the image;

(b) filtering the signals according to fluorescence intensity;

(c) correlating the signals with the backbone of the nucleic acid molecule;

(d) tabulating addition sites of the image using Bayesian inference estimation of the signals; and (e) aligning and assembling the addition sites to determine a nucleotide addition.

The analysis first requires the accumulation of fluorescent signals from an addition site of the image, or "spot" histories, as a function of position (x,y) and addition cycle I(s). Positional data of fluorescence intensities are accumulated after each cycle and are used to link labeled nucleotide additions for a given nick or gap site. For example, the microscope field of view has many nucleic acid molecules each containing 10–20 nicked sites, and the molecules vary in the size of the target and the frequency of the nicked sites.

Next, the signals from the fluorescently labeled nucleotides are filtered according to fluorescence intensity. The signals having insufficient or excessive fluorescence intensities are rejected as false signals. The criteria for this selection is based on the accurate quantitation of fluorochrome addition number. Depending on the set criteria, additions are given "scores" to measure how much they deviate, and the additions with low "scores" may be ultimately rejected in a Bayesian inference scheme.

Confidence estimates and error checking can then be applied to the raw sequence data based on the addition history of a given nick site. A number of failure modes can occur that cause a site to be assigned a low "score".

Examples of failure modes include: template damage can cause incomplete or spurious additions; and excessive nucleotide addition caused by opening a cryptic nick site after nuclease treatment.

After completion of the sequencing cycles, the nucleotide addition signals are then correlated with the nucleic acid molecule backbone or restriction fragments if the signals receive a sufficient confidence value, $C_b$. The assignment of confidence values (1) aids in eliminating noise—so that only additions associated with the target molecules will be considered and (2) helps to bin sequence "reads", according to position, for verification and eventual assembly of the finished sequence.

The Bayesian estimation algorithms developed and set forth in Anantharaman et al. (1997, J. Comp. Biol. 4:91–118) are used to create the optical restriction fragment maps of the nucleic acid molecules and to correlate the labeled nucleotides and/or nucleotide sequence to the nucleic acid molecules as described below.

6. Effecient Probilistic Algorithm for Making Ordered Restriction Maps to Align Nucleotide Sequence The focus of this section is on the description of a probabilistic approach to constructing ordered restriction maps based on the data created from the images of population of individual DNA molecules (clones) digested by restriction enzymes in order to align the nucleotide sequence of individual molecules. Specifically, disclosed in detail are map-making methods and algorithms capable of producing high-resolution, high-accuracy maps rapidly and in a scalable manner to align obtained optically nucleotide sequences along the individual nucleic acid molecule. The resulting methodology, embodied in computer program modules is a key component of the optical mapping automation tools in accordance with the present invention.

6.1. Practical Issues in Optical Mapping

As discussed in the preceding sections, optical mapping is a single molecule methodology for the rapid production of ordered restriction maps from individual (DNA) molecules. Recent technological advances have led to accurate size estimates of the restriction fragments and have been used to construct final restriction maps. Nevertheless, the accuracy of restriction maps created from single molecules is fundamentally limited by the resolution of the microscopy, the imaging system (CCD camera, quantization level, etc.), illumination and surface conditions, and other factors. Furthermore, depending on the digestion rate and the noise inherent to the intensity distribution along the molecules being imaged, it is likely that a small fraction of the restriction sites will be missed, or that spurious sites will be introduced. Additionally, sometimes (rather infrequently) the exact orientation information, i.e., whether the left-most restriction site is the first or the last, is lacking.

As a result, it should be expected that two arbitrary single molecule restriction maps for the same DNA clone obtained this way will at most be "roughly" the same, in the sense that most of the restrictions sites will appear roughly at the same place in both maps if they are aligned (i.e., have the same orientation) and if the identified restrictions sites differ by a small amount.

There are two fundamental approaches to further improving the accuracy and resolution of the maps: (1) improve the chemical and optical processes to minimize the effect of each error source; and (2) use statistical approaches where the restriction maps of a large number of identical clones are combined to create a high-accuracy restriction map. Clearly, these two approaches are not mutually exclusive and various trade-offs exist that can be exploited fruitfully. In accordance with the present invention the problem is attacked by improving all aspects of the process, including the chemical, optical, computational and automation aspects.

Improvements that conceptually belong to the first approach are described in other sections of this application and include, for example, the use of fixed elongated DNA molecules onto positively-charged glass surfaces, which improves sizing precision as well as throughput for a wide range of cloning vectors (cosmid, bacteriophage, and yeast or bacterial artificial chromosomes (YAC or BAC)). Further improvements include, without limitation: the development of a simple and reliable procedure to mount large DNA molecules with good molecular extension and minimal breakage; the optimization of the surface derivatization; maximizing the range of usable restriction enzymes and retention of small fragments; and the development of an open surface digestion format, which facilitates access to samples and lays the foundations for automated approaches to mapping large insert clones.

The complementary set of improvements, which is the focus of this section, have come from the use of powerful statistical tools to process a preliminary collection of single-molecule restriction maps, each one created from an image of a DNA molecule belonging to a pool of identical clones. Individual restriction maps in this collection are almost identical with small variations resulting from sizing errors, partially digested restriction sites and "false" restriction sites and can be combined easily in most cases. However, the underlying statistical problem poses many fundamental challenges; for example, as shown in the following subsection, the presence of some uncertainty in the alignment of a molecule (both orientation and/or matching in the sites) in conjunction with either false cuts or sizing error is sufficient to make the problem NP-complete, that is, computationally infeasible (Garey and Johnson, 1979, *Computer and Intractability: A Guide to the Theory of NP-Completeness*, W.H. Freeman and Co., San Francisco, Calif.). (Also, see et Anantharaman al. (1997, J. Comp. Biol. 4(2):91–118) for some related results on the complexity of this problem). It should be noted that these negative results generally correspond to pathological cases that are less likely to occur in real life. Nonetheless, these negative results play an important role in clarifying the care needed in structuring the algorithm properly. The probabilistic algorithms (using a Bayesian scheme) in accordance with the present invention can handle this problem adequately.

The remainder of this section is organized as follows: In subsection 6.2, the restriction map model used in accordance with the present invention is described along with a formulation of the underlying algorithmic problems. Subsection 6.3 describes statistical models for the problem in accordance with a preferred embodiment of the present invention, based on certain assumptions about the distributions of the bases in DNA and the properties of the chemical processes involved in optical mapping. These models are then used to devise probabilistic algorithms with good average time complexity. The algorithms implemented in computer software in accordance with the present invention cause a computer to produce several output maps ranked by a "quality of goodness" measure. Additionally, estimates of several auxiliary parameters are given, governed by the underlying chemical, optical and image analysis processes (e.g., the digestion rate, false-cut rate, sizing error, contamination with other molecules, etc.). Finally, in subsection 6.5, experimental results are presented on a wide array of data sets (lambdaphage, cosmids; BAC data will be presented in a sequel). Relevant background material for the following discussion can be found, for example, in: discussion on restriction maps and their role in human genome project (Karp, 1993, "Mapping the Genome: Some Combinatorial Problems Arising in Molecular Biology", in *Proc. of 25th Ann. ACM Symp. on the Theory of Computing*, 278–285; Kevles and Hood, eds., 1992, *The Code of Codes*, Harvard University Press, MA; Nicholl, 1994, *An Introduction to Genetic Engineering*, Cambridge University Press; Pevzner, 1990, "DNA Physical Mapping", in *Computer Analysis of Genetic Texts*, 154–158; Primrose, 1995, *Principles of Genomic Analysis: A Guide to Mapping and Sequencing DNA from Different Organisms*, Blackwell Science Ltd., Oxford; Waterman, ed. 1989, *Mathematical Methods for DNA Sequences*, CRC Press, Florida; Waterman, 1995, *An Introduction to Computational Biology: Maps, Sequences and Genomes*, Chapman Hall; Watson, 1977, *Molecular Biology of the Gene*, W.A. Benjamin, Inc., MA), statistics of restriction maps (Lander and Waterman, 1988, "Genomic Mapping by Fingerprinting Random Clones: A Mathematical Analysis," in Genomics 2, 231–239; Lander, 1995, "Mapping Heredity: Using Probabilistic Models and Algorithms to Map Genes and Genomes", Notices of the AMS 42(7), 747–753, adapted from "Calculating the Secrets of Life," National Academy of Sciences; Lander, 1995, Mapping Heredity: Using Probalistic Models and Algorithms to Map Genes and Genomes (Part II), Notices of the AMS, 42(8), 854–858, adapted from "Calculating the Secrets of Life," National Academy of Sciences; Waterman, 1995, *An Introduction to Computational Biology: Maps, Sequences and Genomes*, Chapman Hall) and the algorithmic and computational complexity issues (Branscomb et al., 1990, "Optimizing Restriction Fragment Fingerprinting Methods for Ordering Large Genomic Libraries", Genomics 8, 351–366; Goldberg et al., 1995, J. Comp. Bio., 2(1), 139–152; Karp, 1993, "Mapping the Genome: Some Combinatorial Problems Arising in Molecular Biology", in *Proc. of 25th Ann. ACM Symp. on the Theory of Computing*, 278–285; Krawczak, 1988, In Proc. Natl. Acad. Sciences USA, 85, 7298–7301; Lander, 1995, "Mapping Heredity: Using Probabilistic Models and Algorithms to Map Genes and Genomes", Notices of the AMS, 42(7), 747–753, adapted from "Calculating the Secrets of Life," National Academy of Sciences; Lander, 1995, "Mapping Heredity: Using Probabilistic Models and Algorithms to Map Genes and Genomes (Part II)", Notices of the AMS, 42(8), 854–858, adapted from "Calculating the Secrets of Life," National Academy of Sciences; Pevzner and Waterman, 1995, "Open Combinatorial Problems in Computational Molecular Biology", in *Proc. of the 3rd. Israel Symp. on Theory of Computing and Systems*, January; Waterman, 1995, *An Introduction to Computational Biology: Maps, Sequences and Genomes*, Chapman Hall).

6.2. Restriction Map Models

In accordance with the present invention the restriction map problem can be formulated mathematically as follows. Assuming that all individual single-molecule restriction maps correspond to the same clone, and that the imaging algorithm can only provide the fragment size estimates that are scaled by some unknown scale factor, a single molecule restriction map (SMRM) is represented by a vector with ordered set of rational numbers on the open unit interval (0, 1):

$$D_j = (s_{1j}, s_{2j}, \ldots, s_{M_j j})$$

$$0 < s_{1j} < s_{2j} < \ldots < s_{M_j j} < 1,$$

$$s_{ij} \in Q$$

where Q is the set of rational numbers.

Let $D_j + c$ (a rational $c \in [0, 1]$), denote the vector $$D_j + c = (s_{1j} + c, s_{2j} + c, \ldots, s_{M_j j} + c)$$

where $$-s_{1j} < c < 1 - s_{M_j, j}.$$

Given a rational number $s \in (0, 1)$, its reflection is denoted by $$s^R = 1 - s.$$

Similarly, $D^R_j$, denotes the vector $$D_j^R = (s_{M_j j}^R, \ldots, s_{2j}^R, s_{1j}^R).$$

Note that if the entries of $D_j$ are ordered and belong to the open unit interval, so do $D_j + c$ and $D^R_j$, provided that c is appropriately constrained.

Thus, the mapping problem in accordance with the present invention can be described as follows: given a collection of data (SMRM vectors)

$$D_1, D_2, \ldots, D_m,$$

a final vector H $$H = (h_1, h_2, \ldots, h_N)$$

has to be computed, such that H is "consistent" with each $D_j$. Thus, H represents the correct restriction map and $D_j$'s correspond to several "corrupted versions" of H. In accordance with the present invention the notion of "consistency" is defined using a Bayesian formulation, which depends on the conditional probability that a data item $D_j$ can be present given that the correct restriction map for this particular clone is H.

As known in the art, any such consistency requirement must satisfy certain conditions, given certain side information. For instance, if no false-cuts and accurate sizing information is assumed (even if the digestion may be partial), then it must be the case that for each j, either $D_j \subseteq$ H or $D^R_j \subseteq$ H. In particular, if the digestion is complete (ideal case) then all the $D_j$'s are identical up to reflection and H can be simply chosen as $D_1$.

6.3. The Method of the Present Invention

In spite of the complexity of the issues associated with the formulation of the model (as discussed in detail in Anantharaman et al. 1997, J. Comp. Biol. 4:91–118), it is clear that the imaging system of the present invention provides an output having considerable level of structure that can be exploited to obtain statistically accurate ordered restriction maps efficiently. For instance, if the digestion rate in a particular case is relatively high, then by looking at the distribution of the cuts a good guess can be made about the number of cuts and then only the dataset with large numbers of cuts can be used to create the final map (Reed, expected June 1997, *Optical Mapping*, Ph.D. Thesis, New York University). Other approaches to utilizing the structure of the input have used formulations in which one optimizes a cost function and provides heuristics (as the exact optimization problems are often infeasible). In one approach, the optimization problem corresponds to finding weighted cliques; and in another, the formulation corresponds to a 0–1 quadratic programming problem (Muthukrishnan and Parida 1996, Towards Constructing Physical Maps by Optical Mapping: An Effective Simple Combinatorial Approach, in *Proceedings First Annual Conference on Computational Molecular Biology* (RECOMB97), pp. 209–215, ACM Press). However, these heuristic approaches have only worked on limited sets of data and their effectiveness (or approximability) in large scale practical applications remains unproven. The present invention improves over this and other prior art approaches by providing map-making methods and computer systems capable of producing high-resolution, high-accuracy maps rapidly and in a scalable manner.

Specifically, in accordance with the present invention a probabilistic algorithm based on a Bayesian approach is used to obtain the desired high-accuracy restriction maps. The approach is to use a carefully constructed prior model of the cuts to obtain the best hypothetical model by using Bayes' formula. (See Dempster et al., 1977, J. Roy. Stat. Soc. 39:1–38; Grenander et al. 1993, J. Roy. Stat. Soc. 56:549–603). Generally, the approach requires searching over a high-dimensional hypothesis space and is complicated by the fact that the underlying distributions are multimodal. However, as shown next, in accordance with the present invention the search over this space can be accomplished without sacrificing efficiency. Advantageously, the proposed algorithm is flexible in the sense of enabling the operator to trade computational speed for accuracy of the final map by suitably constraining various parameters in the implementation. The method has been implemented and extensively tested over automatically generated data with good results (see section 6.5).

The main ingredients of this Bayesian scheme in accordance with a preferred embodiment of the present invention are the following:

(1) A Model or Hypothesis H, of the map of restriction sites; and (2) A Prior distribution of the data (SMRM vectors)

$$Pr[D_j|H]$$

Assuming pair-wise conditional independence of the data (SMRM) vectors $D_j$, i.e., $$Pr[D_j|D_{j1}, \ldots, D_{jm}, H] = Pr[D_j|H]$$

the conditional probability of the entire data set of SMRM vectors given a hypothesis H becomes $$Pr[D|H] = \prod_j^m Pr[D_j|H],$$

where the index j ranges over the data set.

As known in the art, the posterior distributions via Bayes' rule are then given by the expression $$Pr[H|D] = \frac{Pr[D|H]Pr[H]}{Pr[D]} \quad (1)$$

where Pr[H] is the prior unconditional distribution of hypothesis H, and Pr[D] is the unconditional distribution of the data. In accordance with a preferred embodiment of the present invention, using this formulation, the space of all hypotheses is searched to find the most "plausible" hypothesis H* that maximizes the posterior probability. This hypothesis provides the final output map in a preferred embodiment.

To compute the hypothesis H* in equation (1), one needs to compute or model the quantities on the right. In a preferred embodiment of the present invention, the hypotheses H is modeled by a small number of parameters Φ (H) (comprising, for example, the number of cuts, distributions of the cuts, distributions of the false cuts, etc.). In a specific embodiment of the present invention only a few of these parameters (number of cuts) are represented by prior models, and the other parameters are implicitly assumed to be equi-probable. Accordingly, in a preferred embodiment, the model of Pr[H] used in accordance with the present invention is relatively simple.

In accordance with the present invention the unconditional distributions for the data Pr[D] in Eqn. (1) does not have to be computed at all since it does not effect the choice of H*. In contrast, in a preferred embodiment of the present invention, a very detailed model is used for the conditional distribution for the data given the chosen parameter values for the hypothesis. One can re-write Eqn. (1) as $$\log(Pr[\Phi(H)|D]) = \Lambda + \text{Penalty} + \text{Bias}, \quad (2)$$

where $$\Lambda \equiv \Sigma_j \log(Pr[D_j|\Phi(H)])$$

is the likelihood function,

Penalty=log $Pr(\hat{\Phi}(H))$ and

Bias=−log $(Pr[D])$=a constant.

In these equations Φ (H) corresponds to the parameter set describing the hypothesis and $$\hat{\Phi}(H) \subseteq \Phi(H)$$

a subset of parameters that have a nontrivial prior model. In the following, the symbol H is used for Φ (H), when the context creates no ambiguity.

It should be noted that the bias term in Eqn. (2) has no effect as it is a constant (independent of the hypothesis), and that the penalty term has any discernible effect only when the data set is small. Thus, in a preferred embodiment directed to the use of relatively large data sets, the focus is on the term Λ which dominates all other terms in the right hand side of Eqn. (2).

Note that the approach based on the Bayesian scheme used in accordance with the present invention enjoys many advantages. For example, one obtains the best possible estimate of map given the data, subject only to the comprehensiveness of the model Φ (H) used. Further, for a comprehensive model H, estimates of Φ (H) are unbiased and errors converge asymptotically to zero as data size increases. Next, additional sources of error can be modeled simply by adding parameters to Φ (H). It is important for practical applications that estimates of the errors in the result can be computed in a straightforward manner. Advantageously, the algorithm also provides an easy way to compute a quality measure.

As discussed next, however, in general the posterior density, Pr[H|D] used in Eqn. (1) and (2) is multimodal and the prior Pr[D_j|H] does not admit a closed form evaluation (as it is dependent on the orientation and alignment with H). Thus, in accordance with the present invention, an iterative sampling technique is developed for the proper evaluation.

In particular, in a preferred embodiment, the method of obtaining accurate restriction maps using the Bayes' formulation above has two parts: (1) a sample hypothesis is taken, and a local search is performed for the most plausible hypothesis in its neighborhood using gradient search techniques; (2) a global search is used to generate a set of sample hypotheses and filter out all but the ones that are likely to be near plausible hypotheses. The descriptions of the local and global searches performed in accordance with the present invention are described next in that order.

Figure 6:
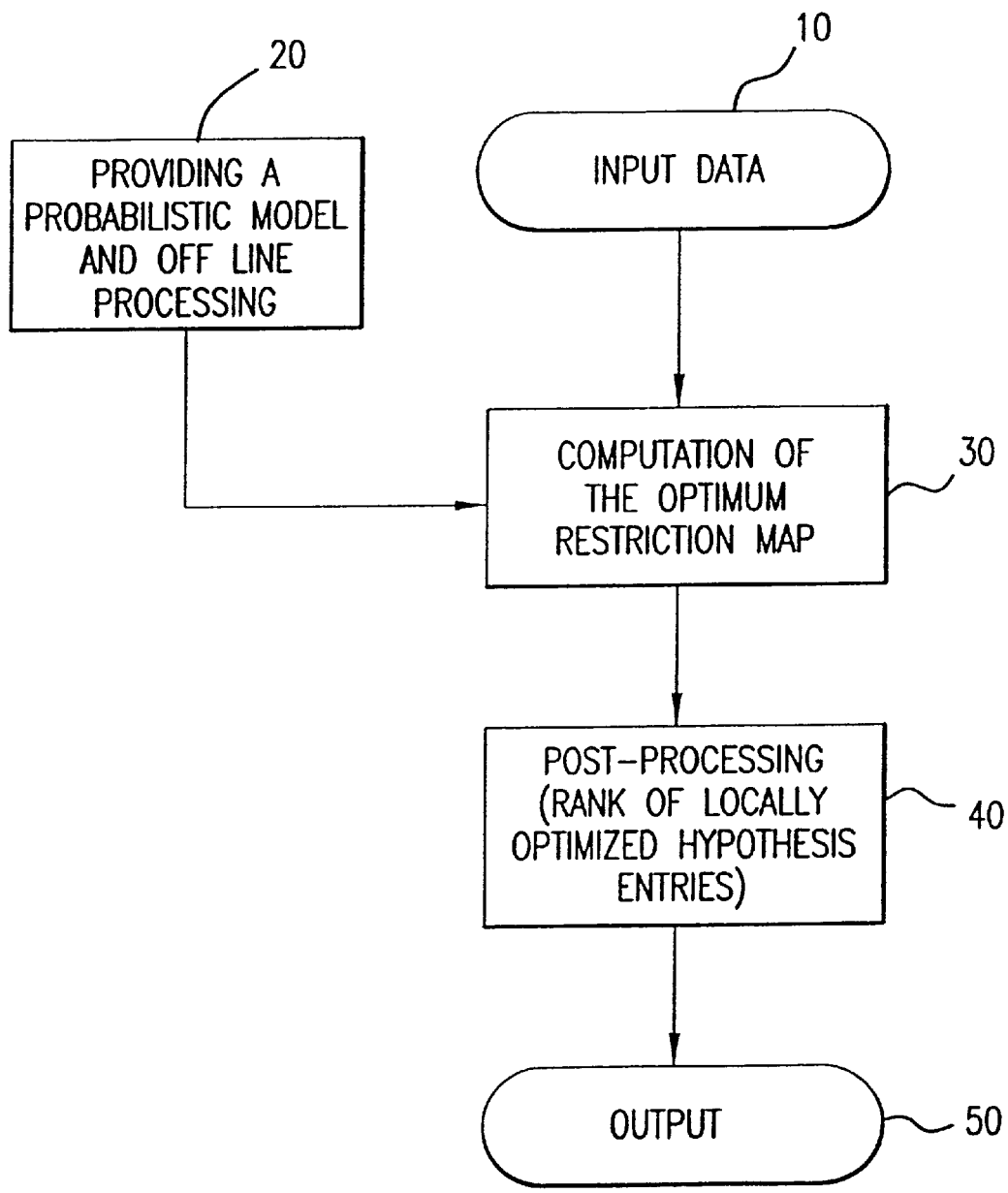
FIG. 6 illustrates in a block-diagram form a preferred embodiment of the method of making a restriction map of the present invention.

FIG. 6 illustrates in a block-diagram form a preferred embodiment of the method of the present invention. As shown in the figure, at block 10 the method is initiated with input data from the imaging system. This input generally comprises a set of observation vectors (molecules) $D_j$. With reference to the notations introduced above, at block 20 the method provides a probabilistic model of the data, comprising a hypothesis H of the map of restriction sites, and a model Pr[D|H] of the distribution of the data conditioned on the hypothesis. Also included in this block are various processing routines, used in accordance with the present invention for efficient off-line computation of different output parameters.

At block 30, the method of the present invention combines the input data and the probabilistic model parameters to compute the optimal restriction map hypothesis for the given set of input data. As discussed in detail next, processing 30 comprises in a preferred embodiment two main tasks: (a) conducting a global search over the parameter space for a set of starting hypothesis; and (b) conducting a local search using gradient methods in the vicinity of the selected "seed" hypothesis to obtain the optimal set of parameters for each given hypothesis.

At block 40, in a preferred embodiment the output of processing block 30, expressed in terms of one or more locally optimized hypothesis entries, is sorted under a given "quality of goodness" measure to obtain a final hypothesis, which in a preferred embodiment is the desired accurate restriction map. This map can be stored, displayed or otherwise processed in block 50. Each of the individual blocks illustrated in FIG. 6 is discussed in detail below. Sections 6.1 and 6.2 focus on the process of modeling (block 20 in FIG. 6), while Sections 6.3, 6.4 and 6.5 focus on the processing block 30.

6.3.1. Maps by Bayesian Inference—Modeling the Prior Observation Distribution

As noted above, for a relatively large observation space the prior observation distribution Pr[D|H] is the dominant component that determines the accuracy of the restriction maps obtained in accordance with the present invention. In a preferred embodiment, Pr[D|H] is modeled considering at least the following categories of errors in the image data: 1) Misidentification of spurious materials in the image as DNA; 2) Identifying multiple DNA molecules as one; 3) Identifying partial DNA molecules as complete; 4) Errors in estimating sizes of DNA fragments; 5) Incomplete digestion of DNA; 6) Cuts visible at locations other than digest sites; and 7) Orientation of DNA molecule is not always known.

Given these categories, in a preferred embodiment the observation probability distribution Pr[D|H] is modeled as follows:

(1) A molecule on a surface can be read from left to right or right to left. The uncertainty in orientation is modeled as Bernoulli processes, with the probability for each orientation being equal.

(2) The restrictions sites on the molecule are determined by a distribution induced by the underlying distribution of the four bases (A, T, C, G) in the DNA. For example, it is assumed that the probability that a particular base (e.g., A) appears at a location i is independent of the other bases, though the probabilities are not necessarily identical.

(3) The false cuts appear on the molecule as a Poisson process. This model is based on the simplifying assumption that over a small region $\Delta h$ on the molecule, the $$Pr[\text{\# False cuts}=1 \text{ over } \Delta h]=\lambda_f \Delta h$$

and the $$Pr[\text{\# False cuts} \geq 2 \text{ over } \Delta h]=o(\Delta h).$$

(4) The fragment size (the size of the molecule between two cuts) is estimated with some loss of accuracy (dependent on the stretching of the molecule, fluorochrome attachments and the image processing algorithm). The measured size is assumed to have Gaussian distribution.

The modeling process used in accordance with a preferred embodiment is described in more detail next. The following notations will be used to describe the parameters of the independent processes responsible for the statistical structure of the data. Unless otherwise specified, the indices i, j and k are to have the following interpretation: The index i ranges from 1 to N and refers to cuts in the hypothesis; the index j ranges from 1 to M and refers to data items (i.e., molecules); the index k ranges from 1 to K and refers to a specific alignment of cuts in the hypothesis versus data.

The main parameters of the Bayesian model used in accordance with a preferred embodiment of the present invention are as follows:

$p_{ci}$=Probability that the ith sequence specific restriction site in the molecule will be visible as a cut;

$\sigma_i$=Standard deviation of the observed position of the with cut when present and depends on the accuracy with which a fragment can be sized;

$\lambda_f$=Expected number of false-cuts per molecule observed. Since all sizes will be normalized by the molecule size, this will also be the false-cuts per unit length;

$p_b$=Probability that the data is invalid ("bad"). In this case, the data item is assumed to have no relation to the hypothesis being tested, and could be an unrelated piece of DNA or a partial molecule with a significant fraction of the DNA missing. The cut-sites (all false) on this data item are assumed to have been generated by a Poisson process with the expected number of cuts =$\lambda_n$.

Note that the regular DNA model reduces to the "bad" DNA model for the degenerate situation when $p_{ci} \to 0$ and $\lambda_f \to \lambda_n$. As a result, "bad" DNA molecules cannot be disambiguated from regular DNA molecules if $p_{ci} \approx 0$. In practice, $p_{ci} > 0$ and $\lambda_n > \lambda_f$, and the degenerate case almost never occurs. The "bad" molecules are recognized by having a disproportionately large number of false cuts.

$\lambda_n$=Expected number of cuts per "bad" molecule.

Recall that by Bayes' rule (Eqn. (1))

$$Pr[H|D]=\{Pr[D|H]Pr(H)\}/Pr[D]$$

Assuming that the prior Pr[H] distribution is given (See the following subsection) in terms of just the number of restriction sites, based on the standard Poisson distribution, the task in accordance with the present invention is to find the "most plausible" hypothesis H by maximizing Pr[D|H].

Figure 7:
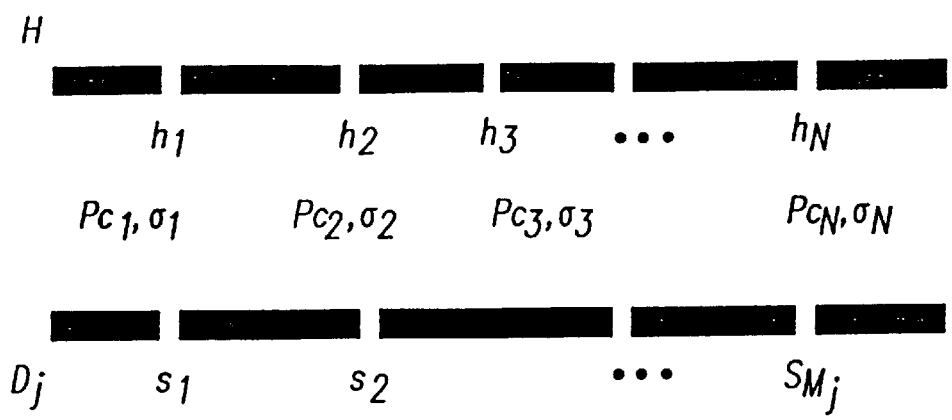
FIG. 7 illustrates a statistical model of cuts of nucleic acid molecules.

In a preferred embodiment of the present invention, hypothesis H is selected as the final map (a sequence of restriction sites, $h_1, h_2, \ldots, h_N$) augmented by certain auxiliary parameters, such as $p_{ci}$, $\sigma_i$, $\lambda_f$, etc. Comparing a data item $D_j$ with respect to a hypothesis H, requires consideration of every possible way that $D_j$ could have been generated by H. FIG. 7 illustrates the concept, including certain notations introduced above. In particular, one needs to consider every possible alignment, where the kth alignment $A_{jk}$ corresponds to a choice of the orientation for $D_j$ as well as identifying a cut on $D_j$, with a true restriction site on H, or labeling the cut as a false cut. In the following description $D_j^{(A_{jk})}$ [also abbreviated as $D_j^{(k)}$], shall denote the interpretation of the j-th data item with respect to the alignment $A_{jk}$. In a preferred embodiment, each alignment describes an independent process by which $D_j$ could have been generated from H, and therefore the total probability density of $D_j$ is the sum of the probability density of all these alignments, plus the remaining possible derivations (invalid data). As a consequence of the pairwise independence and the preceding discussion, the following holds:

$$Pr[D|H] = \prod_j^M Pr[D_j|H],$$

where index j ranges over the data set, and $$Pr_j = Pr[D_j|H] = \tfrac{1}{2}\Sigma_k Pr[D_j^{(k)}|H, \text{good}]Pr[\text{good}] + \tfrac{1}{2}\Sigma_k Pr[D_j^{(k)}|H, \text{bad}]Pr[\text{bad}]$$

where index k ranges over the set of alignments.

In the above equation, $Pr[D_j^{(k)}|H, \text{good}]$ (denoted for simplicity as $Pr_{jk}$) is the probability density of model $D_j$ being derived from model H and corresponding to a particular alignment of cuts (denoted, $A_{jk}$). The set of alignments include alignments for both orientations, hence each alignment has a prior probability of ½. If $D_j$ is bad, the model corresponds to H with $p_{ci} \to 0$ and $\lambda_f \to \lambda_n$. The qualifier "good" for the hypothesis H is omitted, when it is clear from the context.

Figure 8:
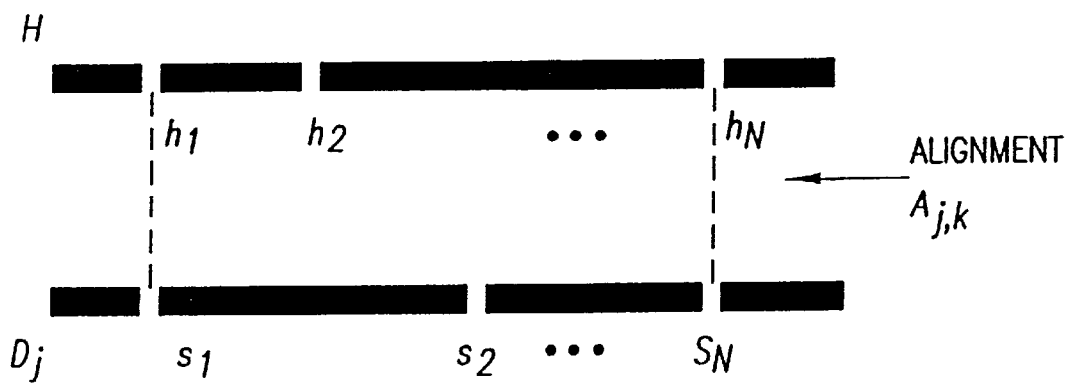
FIG. 8 illustrates an example of the alignment detection.

Thus, in the example shown in FIG. 8, for a given hypothesis H, the conditional probability density that the j-th data item $D_j$ with respect to alignment $A_{jk}$ (i.e., $D_j^{(k)}$) could have occurred is given by the following expression:

$$Pr_{if} = p_{c1} \frac{e^{-(s_1-h_1)^2/2\sigma_1^2}}{\sqrt{2\pi}\,\sigma_1} \times (1-P_{c2}) \times \lambda_f e^{-\lambda_f} \times \ldots \times p_{cN} \frac{e^{-(s_N-h_N)^2/2\sigma_N^2}}{\sqrt{2\pi}\,\sigma_N}$$

The following notations are used next in the most general case considered. Let

N≡Number of cuts in the hypothesis H.

$h_i$≡The ith cut location on H.

$M_j \equiv$ Number of cuts in the data $D_j$.

$K_j \equiv$ Number of possible alignments of the data/evidence $D_j$ against the hypothesis H (or its reversal, the flipped alignment $H^R$).

$s_{ijk} \equiv$ The cut location in $D_j$ matching the cut $h_i$ in H, given the alignment $A_{jk}$. In case such a match occurs, this event is denoted by an indicator variable $m_{ijk}$ taking the value 1.

$m_{ijk} \equiv$ An indicator variable, taking the value 1 if the cut $s_{ijk}$ in $D_j$ matches a cut $h_i$ in the hypothesis H, given the alignment $A_{jk}$. It takes the value 0, otherwise.

$F_{jk} \equiv$ Number of false (non-matching) cuts in the data $D_j$ for alignment $A_{jk}$, that do not match any cut in the hypothesis H. Thus $$F_{jk} = M_j - \sum_{i=1}^{N} m_{ijk}$$

The number of missing cuts is thus $$\sum_{i=1}^{N}(1 - m_{ijk}) = N - \sum_{i=1}^{N} m_{ijk}$$

By an abuse of notation, the indices j and k may be omitted, if from the context it can be uniquely determined which data $D_j$ and alignment $A_{jk}$ are being referred to. Note that a fixed alignment $A_{jk}$ can be uniquely described by marking the cuts on $D_j$ by the labels T (for true cut) and F (for false cut) and by further augmenting each true cut by the identity of the cut $h_i$ of the hypothesis H. From this information, $m_{ijk}$, $s_{ijk}$, $F_{jk}$, etc. can all be uniquely determined. Let the cuts of $D_j$ be $(s_1, s_2, \ldots, s_{Mj})$. Also, let the event $E_i$ denote the situation in which there is a cut in the infinitesimal interval $(s_i - \Delta x/2, s_i + \Delta x/2)$. Thus one has:

$Pr[D_j^{(k)}|H, good] \Delta x_1 \ldots \Delta x_{Mj}$ $= Pr[D_j^{(k)}|H, good](\Delta x)^{Mj}$ $= Pr[E_1, \ldots, E_{Mj}, A_{jk}|H, good]$ $= Pr[E_1, \ldots, E_{Mj}, A_{jk}|m_{ijk}, M_j, H, good] \times Pr[m_{ijk}, M_j|H, good]$ $= Pr[E_1, A_{jk}|m_{ijk}, M_j, H, good] \times Pr[E_2, A_{jk}|E_1, m_{ijk}, M_j, H, good] \times$ $\times \ldots \times Pr[E_\alpha, A_{jk}|E_1, \ldots, E_{\alpha-1}, m_{ijk}, M_j, H good] \times \ldots$ $\times Pr[E_{Mj}, A_{jk}|E_1, \ldots, E_{Mj-1}, m_{ijk}, M_j, H, good] \times Pr[m_{ijk}, M_j|H, good]$ Note the following:

$$Pr[m_{ijk}, M_j|H, good] = \left[\prod_{i=1}^{N}(p_{ci}m_{ijk} + (1 - p_{ci})(1 - m_{ijk}))\right] \times$$
$$e^{-\lambda_f} \lambda_f^{F_{jk}} / F_{jk}!$$
$$= \left[\prod_{i=1}^{N} p_{ci}^{m_{ijk}}(1 - p_{ci})^{(1-m_{ijk})}\right] \times e^{-\lambda_f} \lambda_f^{F_{jk}} / F_{jk}!$$

For the event $E_\alpha$ there are two possible situations to be considered:

(1) $s_\alpha$ is a false cut and the number of false cuts among $s_1, \ldots, s_{\alpha-1}$ is $\beta$.

$Pr[E_\alpha, A_{jk}|E_1, \ldots, E_{\alpha-1}, m_{ijk}, M_j, H, good] = (F_{jk} - \beta)\Delta x$.

(2) $s_\alpha = s_{ijk}$ is a true cut and $h_i$ is the cut in H associated with it.

$$Pr[E_1, \ldots, E_{Mj}, A_{jk}|m_{ijk}, M_j, H, good] = \prod_{i=1}^{N}\left(\frac{e^{-(s_{ijk}-h_i)^2/2\sigma_i^2}}{\sqrt{2\pi}\,\sigma_i}\Delta x\right)^{m_{ijk}} \times F_{jk}!(\Delta x)^{F_{jk}}$$

$$= F_{jk}! \prod_{i=1}^{N}\left(\frac{e^{-(s_{ijk}-h_i)^2/2\sigma_i^2}}{\sqrt{2\pi}\,\sigma_i}\right)^{m_{ijk}}(\Delta x)^{M_j}$$

$${}_j^{(k)}|H, good] = \left[\prod_{i=1}^{N}\left(p_{c_i}\frac{e^{-(s_{ijk}-h_i)^2/2\sigma_i^2}}{\sqrt{2\pi}\,\sigma_i}\right)^{m_{ijk}}(1 - p_{c_i})^{(1-m_{ijk})}\right] \times e^{-}$$

Thus, $$Pr[E_\alpha, A_{jk}|E_1, \ldots, E_{\alpha-1}, m_{ijk}, M_j, H, good] = \frac{e^{-(s_{ijk}-h_i)^2/2\sigma_i^2}}{\sqrt{2\pi}\,\sigma_i}\Delta x$$

Putting it together,

By an identical argument it can be seen that the only alignments relevant for the bad molecules correspond to the situation when all cuts in $D_j$ are labeled false, and for each of two such alignments, $Pr[D_j^{(k)}|H, bad] = e^{-\lambda_n} \lambda_n^{M_j}$ Accordingly, in a preferred embodiment of the present invention the log-likelihood can then be computed as follows:

$\Lambda \equiv \Sigma_j \log Pr[D_j|H]$.

In particular, $$= \sum_j \log\left[p_b e^{-\lambda_n}\lambda_n^{M_j} + \frac{(1-p_b)}{2}\sum_k Pr_{jk}\right] \quad (3)$$

$$= \sum_j \log[p_b e_j + (1 - p_b)]$$

where by definition, $p_b$ is the probability that the data is invalid ("bad"), and $$e_j \equiv e^{-\lambda_n}\lambda_n^{M_j}; \quad d_j \equiv \frac{\left(\sum_k Pr_{jk}\right)}{2}$$

In a preferred embodiment of the present invention, Eqn. (3) for the log-likelihood function is used along with the model of the hypothesis space distribution (considered next) to model the posterior distributions Pr[H|D] for a given observation space D. As known in the art, for a given hypothesis H taking derivatives with respect to the model parameters and solving the resulting equations gives the hypothesis H* that corresponds to the desired output restriction map.

6.3.2. Prior Distribution in the Hypotheses Space

In a specific embodiment of the present invention, the prior distribution in the hypotheses space Pr[H] (and consequently the penalty term in Eqn. (2) above) has a simple model that only depends on the number of restriction sites N. The model implicitly assumes that all hypotheses with same number of cuts are equi-probable, independent of the cut location. Thus, given a k-cutter enzyme (e.g., normally six-cutters like EcoR I in a specific embodiment), the probability that the enzyme cuts at any specific site in a sufficiently long clone is given by $$p_e = (1/4)^k.$$

Thus, if a clone is of length G bps and the expected number of restriction sites in the clone $\lambda_e = G\, p_e$, then the probability that the clone has exactly N restriction cuts is given by:

$$Pr[\text{\# restriction sites}=N|\text{enzyme, } e \text{ and clone of length } G] \equiv \exp\{-\lambda_e\}\lambda_e^N/N!.$$

This expression is based on the assumption that all four bases $\epsilon\{A, T, C, G\}$ occur in the clone with equal probability=¼. However, as it is known (Baker et al., 1984), human genome is CG-poor (i.e., $Pr[C]+Pr[G]=0.32 < Pr[A]+Pr[T]=0.68$).

Therefore, in a preferred embodiment of the present invention a more realistic model is used to provide a better estimation for $p_e$, given by the expression:

$$p_e = (0.16)^{\#CG}(0.34)^{\#AT},$$

where {#CG} denotes the number of C or G in the restriction sequence for the enzyme and similarly, {#AT} denotes the number of A or T in the restriction sequence.

Sections 6.1 and 6.2 define the models used in a preferred embodiment of the present invention for the prior observation distribution and the hypothesis space, respectively. As known in the art of scientific computation, there are various ways of computing different quantities, which generally are characterized by different computational efficiency and numerical accuracy. The following sections describe the computation and use of the model parameters in specific embodiments of the present invention.

6.3.3. Local Search Algorithm

Assume first that a hypothesis is defined over the parameter space and the task is to define the best, i.e., most plausible restriction map given the input observation space.

In order to find the most plausible restriction map, in accordance with a preferred embodiment, the cost function derived in Section 6.1.1 above, is optimized with respect to the following parameters:

Cut Sites=$h_1, h_2, \ldots, h_N$,

Cut Rates=$p_{c1}, p_{c2}, p_{cN}$,

Std. Dev. of Cut Sites=$\sigma_1, \sigma_2, \ldots, \sigma_N$,

Auxiliary Parameters=$p_b$, $\lambda$ and $\lambda_n$.

Let any of these parameters be denoted by $\theta$. As known in the art, with reference to Eqn. (2) above, the optimal solution with respect to each individual parameter $\theta$ is found using the equation (4), $$\frac{\partial \Lambda}{\partial \theta} = 0, \quad (4)$$

which gives the extremal point of $\Lambda$ with respect to the individual parameter $\theta$.

Next, the computation of each of the individual parameters in accordance with the present invention is considered separately.

Case 1: $\theta \rightarrow p_b$

Taking the first partial derivative of the likelihood function with respect to $p_b$ gives:

$$\frac{\partial \Lambda}{\partial p_b} = \sum_j \frac{(e_j - d_j)}{p_b e_j + (1 - p_b) d_j} \quad (5)$$

where $p_b$ is the probability that the data is invalid, and $e_j$, $d_j$ are as defined in Eqn. (3). Taking the second partial derivative gives:

$$\frac{\partial \Lambda}{\partial p_b^2} = -\sum_j \frac{(e_j - d_j)^2}{[p_b e_j + (1 - p_b) d_j]^2} \quad (6)$$

In accordance with a preferred embodiment of the present invention $\Lambda$ can be optimized iteratively to estimate the best value of $p_b$, by means of the following application of the Newton's equation:

$$p_b := p_b - \frac{\partial \Lambda / \partial p_b}{\partial^2 \Lambda / \partial p_b^2}$$

where the first and second partial derivatives are as indicated above. The above expression is used in the iterative optimization in accordance with a preferred embodiment of the present invention. Iterative techniques for function optimization are known in the art and need not be considered in detail.

Case 2: $\theta \rightarrow \lambda_n$

The expected number of cuts per "bad" molecule is simply estimated to be the average number of cuts. Note that, $$\frac{\partial \Lambda}{\partial \lambda_n} = \sum_j \frac{p_b e_j (M_j / \lambda_n - 1)}{p_b e_j + (1 - p_b) d_j}$$

should be zero at the local maxima. Thus a good approximation is obtained by taking $$\sum_j \left(\frac{M_j}{\lambda_n} - 1\right) \approx 0$$

leading to the update rule $$\lambda_n := \frac{\sum_j M_j}{\sum_j 1} = \frac{\sum_j M_j}{\text{Total number of molecules}}$$

Thus, in accordance with a preferred embodiment of the present invention, $\lambda_n$ is simply the average number of cuts per molecule.

Case 3: $\theta \to h_i$, $p_{ci}$, $\sigma_i$ (i=1, ... N), or $\lambda$.

Unlike in the previous two cases, these parameters are in the innermost section of the probability density expression and computing any of these gradients will turn out to be computationally comparable to evaluating the entire probability density. In this case, $$\frac{\partial \Lambda}{\partial \theta} = \sum_j \frac{1}{Pr_j} \left(\frac{1-p_b}{2} \sum_k Pr_{jk} \chi_{jk}(\theta)\right), \text{ where } Pr_j \equiv Pr[D_j|H]$$

and where $$\chi_{jk}(\theta) \equiv \left[\frac{F_{jk}}{\lambda_f} \frac{\partial \lambda_f}{\partial \theta} - \frac{\partial \lambda_f}{\partial \theta}\right] +$$

$$\sum_{i=1}^{N} \left[\frac{m_{ijk}}{p_{ci}} \frac{\partial p_{ci}}{\partial \theta} - \frac{1-m_{ijk}}{1-p_{ci}} \frac{\partial p_{ci}}{\partial \theta}\right] +$$

$$\sum_{i=1}^{N} m_{ijk} \left[\frac{\partial}{\partial \theta}\left(\frac{-(s_{ijk}-h_i)^2}{2\sigma_i^2}\right) - \frac{1}{\sigma_i}\frac{\partial \sigma_i}{\partial \theta}\right]$$

For convenience, now define $$\pi_{jk} \equiv \left(\frac{1-p_b}{2}\right) \frac{Pr_{jk}}{Pr_j}$$

as the relative probability density of the alignment $A_{jk}$ for data item $D_j$.

Thus, the expression for the partial derivative with respect to $\theta$ simplifies to $$\frac{\partial \Lambda}{\partial \theta} = \sum_j \sum_k \pi_{jk} \chi_{jk}(\theta)$$

Before examining the updating formula for each parameter optimization, the following notations are introduced for future use. In a preferred embodiment, the quantities defined below are efficiently accumulated for a fixed value of the set of parameters.

$\psi_{0i} \equiv \Sigma_j \Sigma_k \pi_{jk} m_{ijk} \equiv$ Expected number of cuts matching $h_i$ $\psi_{1i} \equiv \Sigma_j \Sigma_k \pi_{jk} m_{ijk} s_{ijk} \equiv$ Sum of cut locations matching $h_i$ $\psi_{2i} \equiv \Sigma_j \Sigma_k \pi_{jk} m_{ijk} s_{ijk}^2 \equiv$ Sum of square of cut locations matching $h_i$.

$\mu_g \equiv \Sigma_j \Sigma_k \pi_{jk} \equiv$ Expected number of "good" molecules.

$Y_g \equiv \Sigma_j \Sigma_k \pi_{jk} M_j \equiv$ Expected number of cuts in "good" molecules.

We note here that $\psi$'s can all be computed efficiently using a simple updating rule that modifies the values with one data item $D_j$ (molecule) at a time. This rule can then be implemented using a Dynamic Programming recurrence equation (described later).

Case 3A: $\theta \to h_i$

Note that $\theta \equiv h_i$ $$\Rightarrow \chi_{jk}(h_i) = m_{ijk}(s_{ijk} - h_i)/\sigma_i^2$$

$$\Rightarrow \frac{\partial \Lambda}{\partial h_i} = \sum_j \sum_k \pi_{jk} m_{ijk}(s_{ijk} - h_i)/\sigma_i^2$$

Thus, $$\frac{\partial \Lambda}{\partial h_i} = \frac{1}{\sigma_i^2}(\Psi_{1i} - h_i \Psi_{0i})$$

Although, $\psi$'s depend on the location $h_i$, they vary rather slowly as a function of $h_i$. Hence, a feasible update rule for $h_i$ in accordance with the present invention is $$h_i = \psi_{1i}/\psi_{0i} \quad (7)$$

Thus the updated value of $h_i$ is simply the "average expected value" of all the $s_{ijk}$'s that match the current value of $h_i$.

Case 3B: $\theta \to p_{ci}$

Note that $\theta \equiv p_{ci}$ $$\Rightarrow \chi_{jk}(p_{ci}) = \frac{m_{ijk}}{p_{ci}} - \frac{1-m_{ijk}}{1-p_{ci}}$$

$$\Rightarrow \frac{\partial \Lambda}{\partial p_{ci}} = \sum_j \sum_k \pi_{jk}\left(\frac{m_{ijk}}{p_{ci}} - \frac{1-m_{ijk}}{1-p_{ci}}\right)$$

Thus, $$\frac{\partial \Lambda}{\partial p_{ci}} = \frac{\Psi_{0i}}{p_{ci}} - \frac{\mu_g - \Psi_{0i}}{1-p_{ci}}$$

Again, arguing as before, the following feasible update rule for $p_{ci}$ can be used:

$$p_{ci} := \psi_{0i}/\psi_g. \quad (8)$$

Thus, in a preferred embodiment of the present invention, $p_{ci}$ is just the fraction of the good molecules that have a matching cut at the current value of $h_i$.

Case 3C: $\theta \to \sigma_i$

Note that, $\theta \equiv \sigma_i$ $$\Rightarrow \chi_{jk}(\sigma_i) = m_{ijk}\left(\frac{(s_{ijk}-h_i)^2}{\sigma_i^3} - \frac{1}{\sigma_i}\right)$$

$$\Rightarrow \frac{\partial \Lambda}{\partial \sigma_i} = \sum_j \sum_k \pi_{jk} m_{ijk}\left(\frac{((s_{ijk}-h_i))^2}{\sigma_i^3} - \frac{1}{\sigma_i}\right)$$

Thus, $$\frac{\partial \Lambda}{\partial \sigma_i} = \frac{1}{\sigma_i^3}(\Psi_{2i} - 2h_i \Psi_{1i} + h_i^2 \Psi_{0i} - \sigma_i^2 \Psi_{0i}).$$

$$\sigma_i^2 := \frac{(\Psi_{2i} - 2h_i \Psi_{1i} + h_i^2 \Psi_{0i})}{\Psi_{0i}}$$

This gives the following feasible update rule for $\sigma_i^2$:

$$\sigma_i^2 := \frac{\Psi_{2i}}{\Psi_{0i}} - \left(\frac{\Psi_{1i}}{\Psi_{0i}}\right)^2 \quad (9)$$

Using the estimate for $h_i$ (Eqn. 4), this simplifies to:

Accordingly, in a preferred embodiment of the present invention the model parameters is simply the variance of all the $s_{ijk}$'s that match the current value of $h_i$.

Case 3D: $\theta \to \lambda$.
Note that, $\theta \equiv \lambda_f$ $$\Rightarrow \chi_{jk}(\lambda_f) = \frac{F_{jk}}{\lambda_f} - 1 = \frac{M_j - \sum_i m_{ijk}}{\lambda_f} - 1 \tag{10}$$

$$\Rightarrow \frac{\partial \Lambda}{\partial \lambda_f} = \sum_j \sum_k \pi_{jk} \left( \frac{M_j - \sum_i m_{ijk}}{\lambda_f} - 1 \right)$$

$$= \frac{\gamma_g - \sum_i \Psi_{0i}}{\lambda_f} - \mu_g$$

$$\lambda_f := \frac{\gamma_g}{\mu_g} - \sum_i \frac{\Psi_{0i}}{\mu_g}$$

This gives the following feasible update rule for $\lambda_f$. Accordingly, in a preferred embodiment of the present invention the model parameter is computed as the average number of unmatched cuts per "good" molecule. (Note that the molecules are already normalized to unit length.)

Case 3E: $\theta \to p_c = p_{c1} = \ldots = p_{cN}$ (Constrained)
Note that, $$\frac{\partial \Lambda}{\partial p_c} = \sum_j \sum_k \sum_{i=1}^N \pi_{jk} \left( \frac{m_{ijk}}{p_c} - \frac{1 - m_{ijk}}{1 - p_c} \right)$$

Thus, in a preferred embodiment of the present invention the $$p_c := \frac{\sum_i \Psi_{0i} / N}{\mu_g} \tag{11}$$

update rule for this case is

Case 3F: $\theta \to \sigma = \sigma_1 = \ldots = \sigma_N$ (Constrained)

$$\frac{\partial \Lambda}{\partial \sigma} = \sum_j \sum_k \sum_{i=1}^N \pi_{jk} m_{ijk} \left( \frac{(s_{ijk} - h_i)^2}{\sigma^3} - \frac{1}{\sigma} \right)$$

Note that,
The update equation for this case is:

$$\sigma^2 := \frac{\sum_i (\Psi_{2i} - \Psi_{1i}^2 / \Psi_{0i})}{\sum_i \Psi_{0i}} \tag{12}$$

Equations (3)–(12) above define the local search algorithm used in a specific embodiment of the present invention to determine the most plausible hypothesis in the neighborhood of a sample hypothesis H, using gradient search techniques. In the following section, an update algorithm using dynamic programming is disclosed in a preferred embodiment of the present invention to determine the desired quantities in a computationally efficient way.

6.3.4. Update Algorithm: Dynamic Programming

As seen in the preceding section, in each update step of the gradient search, one needs to compute the new values of the parameters based on the old values of the parameters, which affect the "moment functions": $\Psi_{0i}, \Psi_{1i}, \Psi_{2i}, \mu_g$ and $Y_g$. For the ease of expressing the computation, the following additional auxiliary expressions are used below:

$$P_j \equiv \sum_k \left( \frac{Pr_{jk}}{e^{-\lambda_f}} \right) \tag{13}$$

$$W_{ij} \equiv \sum_k \left( \frac{Pr_{jk} m_{ijk}}{e^{-\lambda_f}} \right)$$

$$SUM_{ij} \equiv \sum_k \left( \frac{Pr_{jk} m_{ijk} s_{ijk}}{e^{-\lambda_f}} \right)$$

$$SQ_{ij} \equiv \sum_k \left( \frac{Pr_{jk} m_{ijk} s_{ijk}^2}{e^{-\lambda_f}} \right)$$

One motivation for this formulation is to avoid having to compute $e^{-\lambda}$ repeatedly, since this is a relatively expensive computation. Note that, the original moment function can now be computed as follows:

$$Pr_j = \left( \frac{1 - p_b}{2} \right) e^{-\lambda_f} \times P_j + p_b e_j \tag{14}$$

$$\Psi_{0i} = \left( \frac{1 - p_b}{2} \right) e^{-\lambda_f} \sum_j \frac{W_{ij}}{Pr_j}$$

$$\Psi_{1i} = \left( \frac{1 - p_b}{2} \right) e^{-\lambda_f} \sum_j \frac{SUM_{ij}}{Pr_j}$$

$$\Psi_{2i} = \left( \frac{1 - p_b}{2} \right) e^{-\lambda_f} \sum_j \frac{SQ_{ij}}{Pr_j}$$

$$\mu_g = \left( \frac{1 - p_b}{2} \right) e^{-\lambda_f} \sum_j \frac{P_j}{Pr_j}$$

$$\gamma_g = \left( \frac{1 - p_b}{2} \right) e^{-\lambda_f} \sum_j \frac{M_j P_j}{Pr_j}$$

Finally, $$Pr[D|H] = \prod_j Pr_j.$$

The definitions for $P_j$, $W_{ij}$, $SUM_{ij}$ and $SQ_{ij}$ involve all alignments between each data element $D_j$ and the hypothesis H. This number is easily seen to be exponential in the number of cuts N in the hypothesis H, even if one excludes such physically impossible alignments as the ones involving cross-overs (i.e., alignments in which the order of cuts in H and $D_j$ are different). First, consider. $P_j$:

$$P_j \equiv \sum_k \left( \frac{Pr_{jk}}{e^{-\lambda_f}} \right)$$

$$= \sum_k \left[ \prod_{i=1}^N \left( p_{ci} \frac{e^{-(h_i - s_{ijk})^2 / 2\sigma_i^2}}{\sqrt{2\pi} \sigma_i} \right)^{m_{ijk}} \times \prod_{i=1}^n (1 - p_{ci})^{1 - m_{ijk}} \times \lambda_f^{F_{jk}} \right]$$

Following is a description of a set of recurrence equations used in a preferred embodiment of the present invention for computing the values for all alignments efficiently. The set of alignments computed are for the cuts $1, \ldots, M_j$ of $D_j$ mapped against the hypothesized cuts $1, \ldots, N$. The recurrence equations are defined in terms of $$P_{q,r} \equiv P_j(s_q, \ldots, s_{Mj}; h_r, \ldots, h_N),$$

which is the probability density of all alignments for the simpler problem in which cuts $s_1, \ldots, s_{q-1}$ are missing in the data $D_j$ and the cuts $h_1, \ldots, h_{r-1}$ are missing in the hypothesis H. Then, clearly $$P_j \equiv P_{1,1} \quad (15)$$

$$P_{q,r} \equiv \lambda_f P_{q+1,r} + \sum_{t=r}^{N} P_{q+1,t+1} \left[ \prod_{i=r}^{t-1} (1 - p_{ci}) \right] p_{ct} \frac{e^{-(h_t - s_q)^2/2\sigma_t^2}}{\sqrt{2\pi}\, \sigma_t}$$

where $1 \leq q \leq M_j$ and $1 \leq r \leq N+1$.

Eqn. (15) follows from a nested enumeration of all possible alignments. The recurrence terminates in $P_{Mj+1,r}$, which represents $P_j$ if all cuts in $D_j$ were missing and cuts $h_1, \ldots, h_{r-1}$ in H were missing:

$$P_{M_j,r} = \sum_{i=r}^{N} (1 - p_{ci}) \quad (16)$$

Thus the total number of terms $P_{q,r}$ to be computed is bounded from above by $(M_j+1)(N+1)$ where $M_j$ is the number of cuts in data molecule $D_j$ and N is the number cuts in H. Each term can be computed in descending order of q and r using Equations (15) and (16). The time complexity associated with the computation of $P_{q,r}$ is $O(N-r)$ in terms of the arithmetic operations.

Note also that the Eqn. (15) can be written in the following alternative form:

$$j \equiv P_{1,1} \quad (17)$$

$$r \equiv \lambda_f P_{q+1,r} + P_{q+1,r+1} p_{ci} \frac{e^{-(h_t - s_q)^2/2\sigma_t^2}}{\sqrt{2\pi}\, \sigma_t} +$$

$$(1 - p_{cr})[P_{q,r+1} - \lambda_f P_{q+1,r+}$$

where $1 \leq q \leq M_j$ and $1 \leq r \leq N+1$.

Thus, by computing $P_{q,r}$ in descending order of r, only two new terms [and one new product $(1-p_{cr})$ in Eqn. (17) needs be to be computed for each $P_{q,r}$. With this modification, the overall time complexity of the iterative computation used in accordance with the present invention reduces to $O(M_j N)$.

The complexity can be further improved in a preferred embodiment by taking advantage of the fact that the exponential term is negligibly small unless $h_t$ and $s_q$ are sufficiently close (e.g., $|h_t - s_q| \leq 3\sigma_t$).

For any given value of q, only a small number of $h_t$ will be close to $s_q$. For a desired finite precision only a small constant fraction of $h_t$'s will be sufficiently close to $s_q$ to require that the term with the exponent be included in the summation. It should be noted that in practice, even a precision of $10^{-10}$ will only require 3–5 terms to be included with a around 1%.

Note, however, that even with this optimization in the computation for Eqn. (15), the computation of $P_{q,r}$ achieves no asymptotic improvement in the time complexity, since $P_{q,r}$ with consecutive r can be computed with only two new terms, as noted earlier. However, for any given q, only for a few r values are both of these additional terms non-negligible. The range of r values (say, between $r_{min}$ and $r_{max}$) for which the new terms with $(\exp\{-(h_r - s_q)^2/2\sigma_t^2\})$ is significant can be precomputed in a table indexed by $q=1, \ldots, M_j$. For $r > r_{max}$ all terms in the summation are negligible. For $r < r_{min}$ the new exponential term referred to previously is negligible. In both cases, the expression for $P_{q,r}$ can be simplified:

$$P_{q,r} = \begin{cases} \lambda_f P_{q+1,r} & \text{if } r > r_{max}[q]; \\ \lambda_f P_{q+1,r} + (1 - P_{cr})(P_{q,r+1} - \lambda_f P_{q+1,r+1}), & \text{if } r < r_{min}[q]. \end{cases} \quad (18)$$

Figure 9:
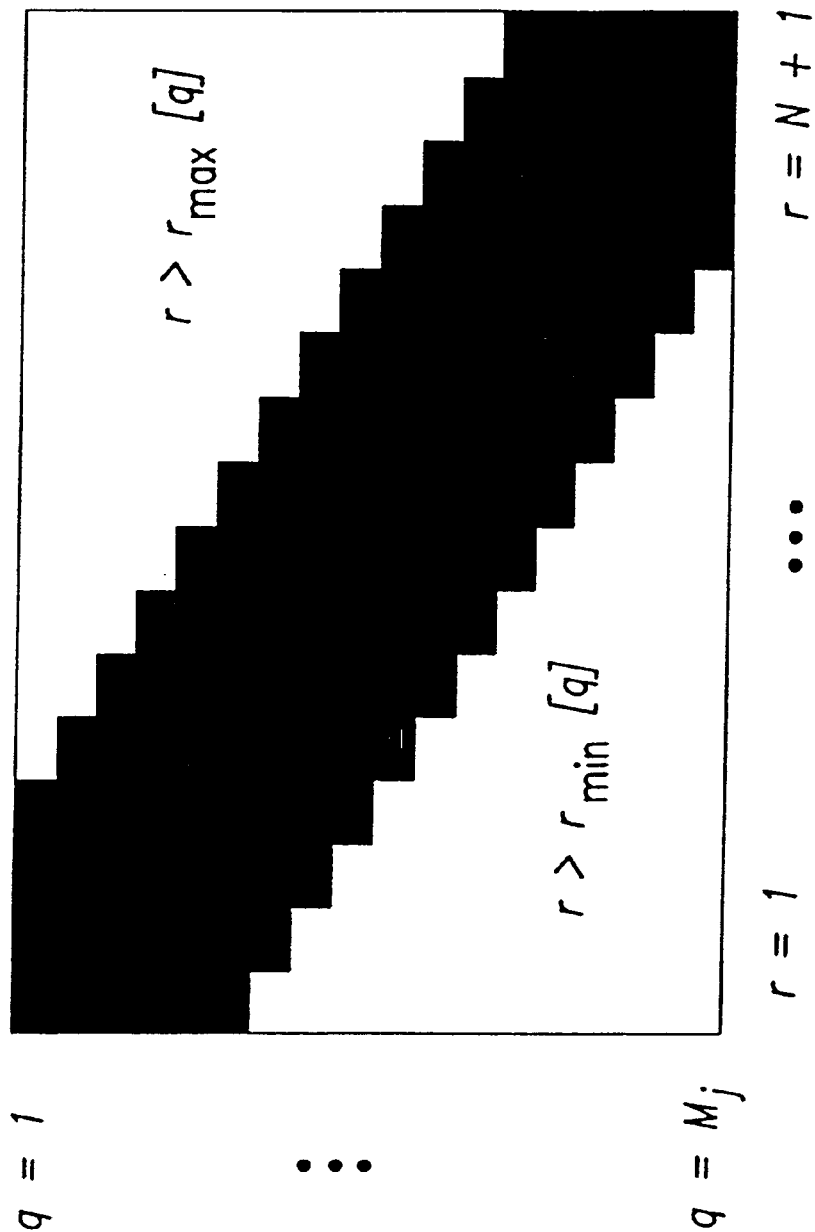
FIG. 9 is a variable block diagonal matrix for the dynamic programming.

Since both $r_{min}[q]$ and $r_{max}[q]$ are monotonically nondecreasing functions of q, the (q,r) space divides as shown in FIG. 9. Of course, the block diagonal pattern need not be as regular as shown and will differ for each data molecule $D_j$.

Note again that the ultimate object is to compute $P_{1,1}$. Terms $P_{q,r+1}$ with $r > r_{max}[q]$, cannot influence any term $P_{q',r'}$ with $r' \leq r$ (see Eqn. (15)). Therefore, any term $P_{q,r+1}$ with $r > r_{max}[q]$ cannot influence $P_{1,1}$ as is readily seen by a straightforward inductive argument. Therefore, all such terms need not be computed at all.

For $r < r_{min}[q]$, these terms are required but need not be computed since they always satisfy the following identity:

$$P_{q,r} = (1 - P_{Cr}) P_{q,r+1}, \quad r < r_{min}[q].$$

This follows from Eqns. (16) and (18) by induction on q. These terms can then be generated on demand when the normal recurrence (Eqn. (15)) is computed and whenever a term $P_{q+1,r}$ is required for which $r < r_{min}[q+1]$, provided terms are processed in descending order of r.

Thus, the effective complexity of the algorithm used in a preferred embodiment of the present invention is $O(M^j (r_{max} - r_{min} + 2))$. Since $r_{max} - r_{min} + 2$ is proportional for a given precision to $\lceil (\sigma N + 1) \rceil$, (where $\sigma$ is an upper bound on all the $\sigma_t$ values) it can be seen that the time complexity for a single molecule $D_j$ is $O(\sigma M_j N)$. Summing over all molecules $D_j$ the total time complexity of the algorithm in accordance with the present invention is $O(\sigma M N)$, where $M = \Sigma_j M_j$. The space complexity is trivially bounded by $O(M_{max} N)$ where $$M_{max} = \max_j M_j.$$

Essentially the same recurrence equations can be used to compute the quantities $W_{ij}$, $SUM_{ij}$ and $SQ_{ij}$, since these 3N quantities sum up the same probability densities $Pr_{jk}$ weighted by $m_{ijk}$, $m_{ijk} s_{ijk}$ or $m_{ijk} s_{ijk}^2$ respectively. The difference is that the termination of the recurrence (Eqn.(15)) is simply $P_{Mj+1,r} = 0$, whereas the basic recurrence equation (Eqn. (15)) contains an additional term corresponding to the $m_{ijk}$ times the corresponding term in the recurrence equation. For example:

$$M_{ij} \equiv SUM_{i,t,1} \text{ and} \quad (19)$$

$$i,q,r \equiv \lambda_f SUM_{i,q+1,r} + \sum_{t=r}^{N} SUM_{i,q+1,t+1} \left[ \prod_{j=r}^{t-1} (1 - p_{cj}) \right] p_{ct} \frac{e^{-(h_t - s_q)^2}}{\sqrt{2\pi}\, \sigma} +$$

$$I_{i \geq r} s_q P_{q+1,i+1} \left[ \prod_{j=r}^{i-1} (1 - p_{cj}) \right] p_{ci} \frac{e^{-(h_i - s_q)^2/2\sigma_t^2}}{\sqrt{2\pi}\, \sigma_i}$$

where $1 \leq q \leq M_j$ and $1 \leq r \leq N+1$, and the expression $I_{i \geq r} \equiv (i \geq r?\ 1{:}0)$ is a shorthand for 1, if $i \geq r$; and 0 otherwise.

Note that the new term is only present if $i \geq r$, and as before need only be computed if the corresponding exponent is significant, i.e., i lies between $r_{min}[q]$ and $r_{max}[q]$. This term is the only nonzero input term in the recurrence since the terminal terms are zero. This recurrence is most easily derived by noting (from Eqns. (3) and (13)) that the sum of products form of $SUM_{ij}$ can be derived from that of $P_j$ by multiplying each product term with $h_i - s_q$ in any exponent by $s_q$, and deleting any term without $h_i$ in the exponent. Since each product term contains at most one exponent with $h_i$, this transformation can also be applied to the recurrence form for $P_j$ (Eqn. (15)), which is just a different factorization of the original sum of products form. The result is Eqn. (19).

The corresponding derivation for $W_{ij}$ and $SQ_{ij}$ is the same except that the $s_q$ is replaced by 1 or $s_q^2$ respectively. If the recurrences for these 3N quantities are computed in parallel with the probability density $P_j$, the cost of the extra term is negligible, so the overall cost of computing both the probability density $P_j$ and its gradients is $O(\sigma M N^2)$. The cost of conversion Eqns. (14) is also negligible in comparison. Moreover this can be implemented as a vectorized version of the basic recurrence with vector size 3N+1 to take advantage of either vector processors or superscalar pipelined processors. We note in passing that if 3N is significantly greater than the average width σ M of the dynamic programming block diagonal matrix shown in FIG. 9 then a standard strength reduction can be applied to the vectorized recurrence equations trading the 3N vector size for a σN+1 vector size and resulting in an alternate complexity of $O(\sigma^2 M N^2)$. It should be noted that implementing this version is harder to code, and the gain is significant only when σ<<1. Note further that the gradient must be computed a number of times (typically 10–20 times) for the parameters to converge to a local maxima.

6.3.5. Global Search Algorithm

Given a sample hypothesis H the local search method of the present invention described in the preceding section can be used to efficiently search for the optimal solution in the parameter space. However, it should be stressed that the prior distribution Pr[D|H] is multimodal and therefore the local search based on the gradients by itself cannot evaluate the best value of the parameters. Instead, in accordance with the present invention one must rely on a sampling of the parameter space to find points that are likely to be near the global maxima. In this respect, examination of the parameter space indicates that the parameters corresponding to the number and locations of restriction sites present the largest amount of multimodal variability. Therefore, for purposes of optimization the sampling may be restricted to a subspace of the original parameter space. In a specific embodiment of the present invention, the following sampling is used $\bar{h}=(N; h_1, h_2, \ldots, h_N)$. In this embodiment, the conditional observation probability density Pr[D|H] can be evaluated pointwise in time $O(\sigma M N)$, and the nearest local maxima located in time $O(\sigma M N^2)$.

Figure 10:
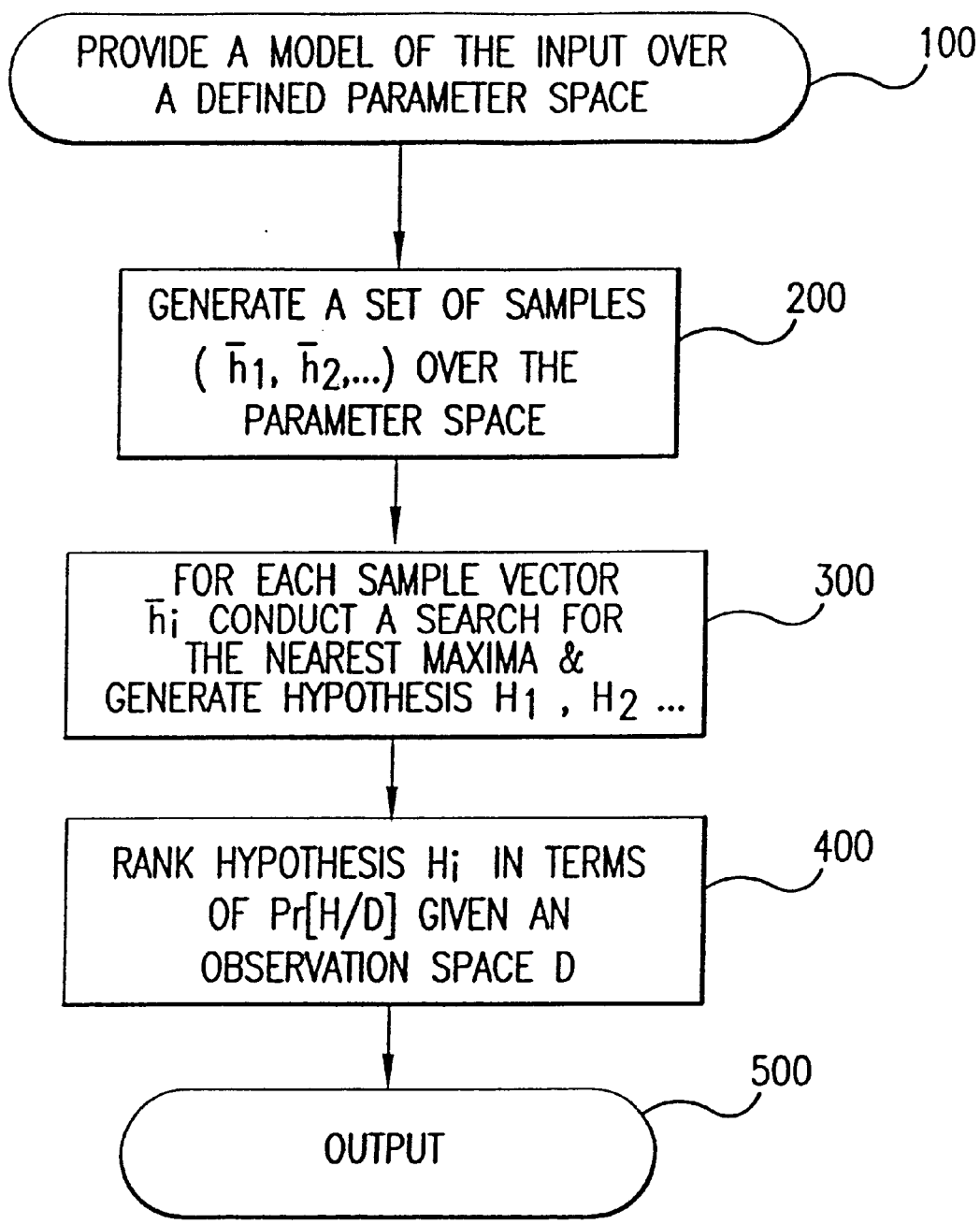
FIG. 10 illustrates in a block-diagram form a preferred embodiment of the method for searching for an optimal solution of the present invention.

More specifically, the search for an optimal solution in a preferred embodiment of the present invention proceeds as follows, the method being illustrated in FIG. 10.

At 100, provide a model of the input signal over a defined parameter space. The particulars of this block have been discussed in Sections 6.1 and 6.2.

At 200, the method proceeds with generating a set of samples $(\bar{h}_1, \bar{h}_2, \bar{h}_3, \ldots)$ of the parameter space, where $\bar{h}_i$ is defined as above. The selection of the sample set is described below.

Next, at 300 these sample points are then used to begin a local search for the nearest maxima and provide hypotheses $(H_1, H_2, H_3, \ldots)$ that correspond to the set of samples in block 200. As shown in Sections 6.3 and 6.4, in accordance with a preferred embodiment of the present invention the local search is performed using gradient search, the computation of which is performed efficiently using dynamic programming.

Finally, at step 400 the generated hypotheses $H_i$ are ranked in terms of their posterior probability density Pr[H|D] (whose relative values also lead to the quality measure for each hypothesis), and one or more hypotheses (leading to maximal posterior probability density) or otherwise estimated to be optimal is provided to output 500 as the final answer.

This section focuses on the implementation of block 200. It should be noted first that even after restricting the sampling space, the high dimension of the space makes the sampling task daunting. Even if the space is discretized (for instance, each $h_i \in \{0, 1/200, \ldots, j/200, \ldots, 1\}$, there are still far too many sample points $$\binom{200}{N}$$

even for a small number of cuts (say, N=8). However, in accordance with a specific embodiment of the present invention, the efficiency of the computation can be improved if an approximate solution is acceptable. To this end, in accordance with the present invention, the following two approaches (and their combination) are used:

(a) approximate Bayesian probability densities can be used in conjunction with a branch and bound algorithm to reject a large fraction of the samples without further local analysis;

(b) an approximate posterior distribution for the location of the cut sites can be used in conjunction with a Monte Carlo approach to generate samples that are more likely to succeed in the local analysis.

In a preferred embodiment, the two methods can be combined: for instance, the first approach can be used to generate the best (one or more) hypothesis with a given small (say, 5) number of cuts. The generated hypothesis can next be used to improve the approximate posterior to be used in the second approach. Note also that, if the data quality is "good", rather simple versions of the heuristics (for global search) lead to greedy algorithms that yield good results quite fast. Following is a description of both approaches used in accordance with the present invention.

Initially, in a preferred embodiment, the parameter N is searched in strictly ascending order. This means one first evaluates the (single) map with no cuts, then applies global and gradient search to locate the best map with 1 cut, then the best map with 2 cuts etc. One continues until the score of the best map of N cuts is significantly worse than the best map of 0 . . . N−1 cuts.

Approximating Bayesian Probability Densities

In a preferred embodiment of the present invention the global search for a particular N uses an approximate Bayesian probability density with a scoring function that is amenable to efficient branch-and-bound search. Observe that good scores for some molecule $D_j$, basically requires that as many cut locations $s_{ij}, \ldots, s_{M_j j}$ as possible must line up close to $h_1, h_2, \ldots, h_N$ in one of the two orientations. This means that any subset of the true map $h_1, h_2, \ldots, h_m$ (m<N) will score better than most other maps of size m, assuming that the digest rate is equal ($p_c = p_{c1} = \ldots = p_{cN}$) Note that for physical reasons the variation among the digest rates is quite small justifying the above assumption and permitting to explicitly constrain these parameters to be the same. For example, if $(h_1, h_2, \ldots, h_N)$ is the correct map, one expects maps with single cuts located at $[h_i]$ ($1 \leq i \leq N$) to score about equally well in terms of the Bayesian probability density. Similarly, maps with two cuts located at pairs of $[h_i, h_j]$ ($1 \leq i < j \leq N$) score about equally well and better than arbitrarily chosen two cut maps. Furthermore, the pair-cut probability densities are more robust than the single cut probability densities with respect to the presence of false cuts, hence, less likely to score maps with cuts in other than the correct locations.

Hence, in accordance with a preferred embodiment, an approximate score function used for a map ($h_1, h_2, \ldots, h_N$) is the smallest probability density for any pair map [$h_i, h_j$], which is a subset of ($h_1, h_2, \ldots, h_N$). In a preferred embodiment, these pair map probability densities are precomputed for every possible pair ([$h_i, h_j$]) if $h_i, h_j$ are forced to have only K values along some finite sized grid, for example at exact multiples of ½% of the total molecule length for K=200. The pair map probability densities can be expressed in the form of a complete undirected graph, with K nodes corresponding to possible locations, and each edge between node i to j having an edge value equal to the precomputed pair map probability density of [$h_i, h_j$]. A candidate map ($h_1, h_2, \ldots, h_N$) corresponds to a clique of size N in the graph, and its approximate score corresponds to the smallest edge weight in the clique.

In general, the clique problem (for instance, with binary edge weights) is NP-complete and may not result in any asymptotic speedup over the exhaustive search. However, for this problem effective branch-and-bound search heuristics is devised in a preferred embodiment.

Consider first the problem of finding just the best clique. In accordance with the present invention, several heuristic bounds can be used to eliminate much of the search space for the best clique. In a specific embodiment, the following two are used:

(1) The score of any edge of a clique is an upper bound on the score of that clique. If the previous best clique found during a search has a better (higher) score than the score of some edge, all cliques that include this edge can be ruled out;

(2) For each node in the graph, precompute the score of the best edge that includes this node. If the previous best clique found during a search has a better (higher) score than this node score, all cliques that include this node are ruled out.

As with all branch-and-bound heuristics the effectiveness of these techniques depends on quickly finding some good solutions, in this case cliques with good scores. Experimentally, it was found that an effective approach to be used in this problem is to sort all K nodes by the Bayesian scores of the corresponding single cut map. In other words, in a preferred embodiment, the method first tries nodes that correspond to restriction site locations that have a high observed cut rate in some orientation of the molecules. Also, the nodes corresponding to cut sites of the best overall map so far (with fewer than N cut sites) are tried first.

For data consisting of a few hundred molecules, the branch-and-bound heuristics allows exhaustive search in under a minute on a Sparc System 20 with $N \leq 7$ (with K=200). For N>7, a simple step-wise search procedure that searches for the best map ($h_1, h_2, \ldots, h_N$) by fixing N–7 nodes based on the previous best map, works well. The N–7 nodes selected are the optimal with respect to a simple metric, for instance, the nodes with the smallest standard error (i.e., ratio of standard deviation to square root of sample size). Next, the global search is modified to save the best B (typically 8000) cliques of each size and then the exact Bayesian probability density is evaluated at each of these B locations, adding certain reasonable values for parameters other than (N; $h_1, \ldots, h_N$). In a preferred embodiment, these parameters can be taken from the previous best map, or by using some prior values if no previous best map is available. For some best scoring subset (typically 32–64) of these maps, gradient search is used in a specific embodiment to locate the nearest maxima (and also accurate estimates for all parameters), and the best scoring maxima is used as the final estimate for the global maxima for the current value of N.

Further Improvements

Several variations to the global search described here, can be used in alternate embodiments. For example, it was found that for large N the approximate score diverges from the true Bayesian score. To reduce the reliance on the approximate score the step-wise search procedure in accordance with the present invention can be modified to fixing, for example, N–3 nodes from the previous best map instead of N–7. For the same value of B, this modification increases the fraction of the search space that is scored with the exact Bayesian score. Fixing N–1 or even N–2 nodes would allow essentially the entire remaining search space to be scored with the exact Bayesian score in alternative embodiments. It should be noted that a potential drawback of this modified embodiment is that the amount of backtracking has been reduced and hence a wrong cut site found for small N is harder to back out of.

Additionally, instead of searching the space in strictly ascending order of N, in an alternative embodiment it is quicker to use a greedy search to locate a good map for a small value of N, for example, 5 and then use the more exhaustive search with backtracking to extend it to larger values of N. For large number of cuts (as in BACs) this heuristic leads to significant saving, since the molecule orientations are known (with high probability) once the best map with N=5 is found. With known molecule orientations, even a greedy search using exact Bayesian scores can locate the correct map with high probability. The final more exhaustive search is needed in a specific implementation mainly to get a good quality measure for the result.

Further, to fix the N–2 or N–3 best nodes it might be better to use a greedy search with exact Bayesian scores: Successively try deleting one cut at a time, locating the cut which reduces the exact Bayesian score the least.

6.3.6. A Quality Measure for the Best Map

In accordance with a preferred embodiment, a quality measure for the best map obtained using the present invention is provided by the ratio of the estimated probability of the dominant mode of the posterior probability density Pr[H|D] to the probability of the sum of values computed for the N best peaks of the multi-modal Pr[H|D]. See also FIG. 1—block 40, and FIG. 10, block 400. Thus, in a preferred embodiment the cost function is a constant multiple of the posterior probability density, and is not normalized by dividing it by the integral of the cost over the entire parameter space.

Specifically, the probability of the dominant mode of the posterior probability density is computed in a preferred embodiment by integrating the probability density over a small neighborhood of the peak (computed in the parameter space). Next, the following simplifying assumption is made: All peaks of the posterior probability density are sharp and the integral of the cost function over a neighborhood where the cost value is larger than a specific value is proportional to the peak density. Thus, in accordance with the present invention, if the N most dominant peaks of the posterior probability density are known, the cost over the entire parameter space can be approximated by the integral over the N neighborhoods of these peaks, where typically N=64.

This quality of goodness measure simplifies the computation considerably, while producing a very good estimate. To take into account sampling errors, such as those which occur when the number of molecules is small, in accordance with a specific embodiment, the density of the best map is reduced by an estimate of the sampling error. This approach tends to make the computed quality measure somewhat pessimistic, however, it provides a lower bound.

It should be noted that the approach of generating a set of restriction maps with different "quality measures" has the additional benefit that this information can be used to safeguard the database from being corrupted and to provide very important feedback to the experimenters who could repeat their experiment and gather more data when the estimated qualities are too low.

In addition, as noted above the output of the algorithm used in accordance with the present invention is guaranteed to have the optimal accuracy. The demand for this high-accuracy is justified by the fact that even a small loss of accuracy contributes to an exponential growth in the complexity of the "contig" problem.

Finally, it is important to note that the method of the present invention described in the preceding sections generalizes easily to other cases where the data model differs significantly. For instance, with BAC data one can expect the end-fragments to occasionally break and to miss the interior fragments occasionally. Other important situations involve the models for circular (non-linearized) DNA, genomic (uncloned) DNA, data sets consisting of clones of two or more DNA's. Other situation involves augmentation with some more (helpful) data that can be made available by appropriate changes to the chemistry—presence of external standards allowing one to work with absolute fragment sizes, or external labeling disambiguating the orientation or alerting one to the absence of a fragment. The flexibility of the approach derives from its generality and cannot be achieved by the simpler heuristics.

6.4. The System of the Invention

Figure 11:
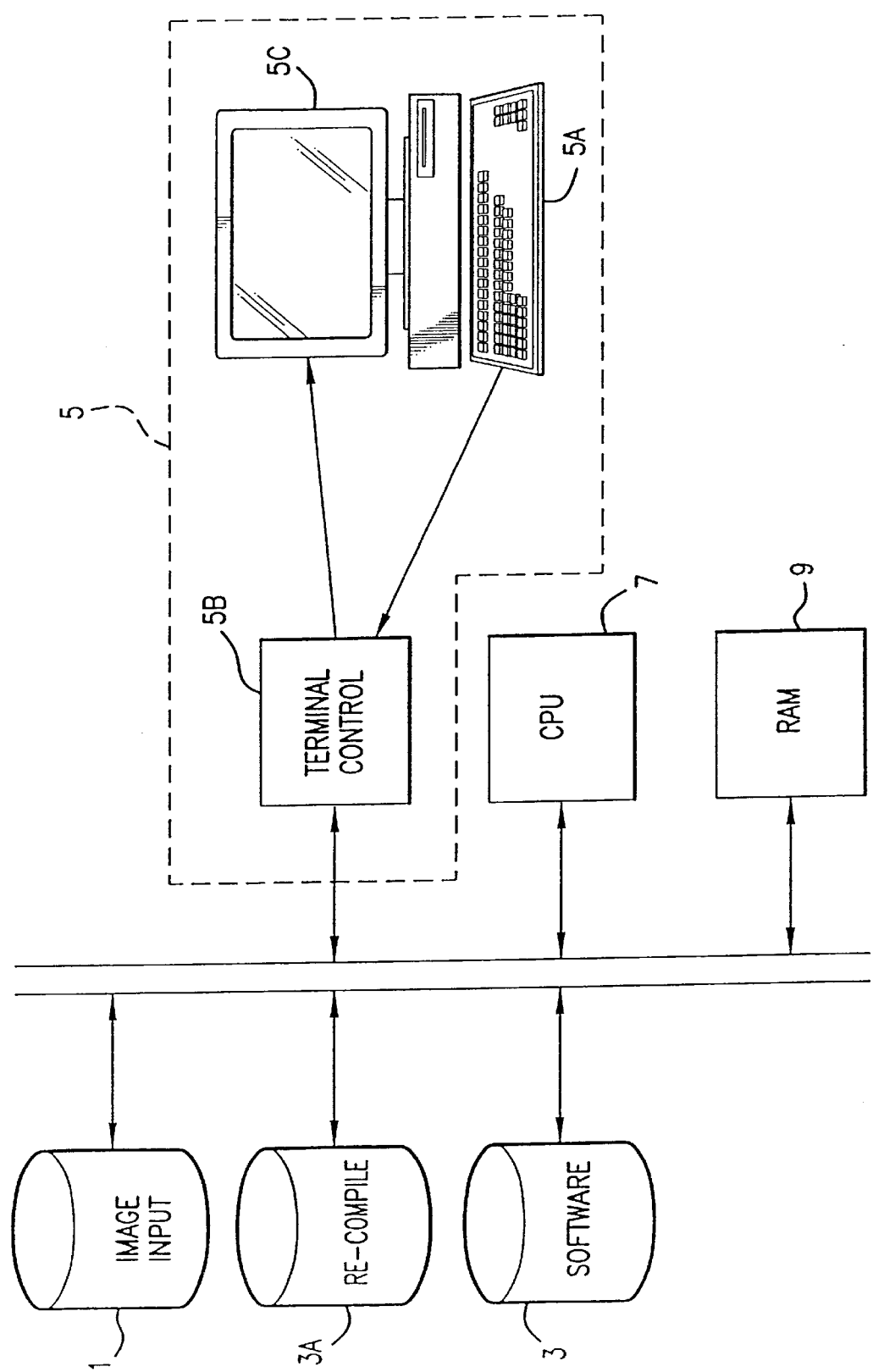
FIG. 11 illustrates the system of the present invention.

The system of the present invention is shown in an illustrative embodiment in FIG. 11. As shown, the system comprises one or more user terminal units 5, each having an input device, such as a standard keyboard that enables it to communicate with the computer via terminal control unit. The unit also has an output device, such as a display that communicates the results of the processing operations to the user. Additional peripheral equipment (not shown), such as printers normally is also included in a standard setup.

The system further comprises a central processor unit (CPU) 7 for performing data processing. RAM storage 9 is also provided for fast-access operations, as known in the art. In a specific embodiment of the present invention the system is implemented on a Sparc 20 station, operating at 80 MHz, with 256 MB of RAM memory. As shown in FIG. 11, the system further comprises input block 1 that communicates imaging information from individual DNA molecules for subsequent processing. It will be appreciated that the imaging operations may be controlled by the same user and/or computer system. The system of the present invention further comprises specialized software 3 and an optional block containing pre-computed quantities used in the processing described in section 6.3 above.

In a specific embodiment, the methods used in accordance with the present invention were implemented in C programming language, running on the Sparc 20, as illustrated in FIG. 11. Extensive experiments conducted over a long time were shown to yield highly accurate maps, consistent with the best result one can expect from the input data.

As shown in the preceding section, the statistically accurate map-making methods of the present invention involve manipulation of large data quantities. In this respect certain observations are in order. First, processing of each individual molecule is largely independent of the processing steps for other molecules. Further, the sample search involved in finding seed sample vectors $\overline{h}_i$ need not proceed sequentially. The implication is that the system of this invention is capable of exploiting the structure of the input to perform the required computations efficiently in a parallel fashion.

As known in the art, one of the basic approaches to minimizing the time to perform computations is to apply some sort of parallelism, so that tasks which are logically independent can be performed in parallel. This can be done, for example, by executing two or more instructions per machine cycle, i.e., by means of instruction-level parallelism. Thus, in a class of computers using superscalar processing, hardware is used to detect independent instructions and execute them in parallel, often using techniques developed in the early supercomputers.

Another powerful approach to exploiting instruction level parallelism is used by the Very Long Instruction Word (VLIW) processor architectures in which the compiler performs most instruction scheduling and parallel dispatching at compile time, reducing the operating burden at run time. By moving the scheduling tasks to the compiler, a VLIW processor avoids both the operating latency problems and the large and complex circuitry associated with on-chip instruction scheduling logic.

As known, each VLIW instruction includes multiple independent operations for execution by the processor in a single cycle. A VLIW compiler processes these instructions according to precise conformance to the structure of the processor, including the number and type of the execution units, as well as execution unit timing and latencies. The compiler groups the operations into a wide instruction for execution in one cycle. At run time, the wide instruction is applied to the various execution units with little decoding. The execution units in a VLIW processor typically include arithmetic units such as floating point arithmetic units. An example of a VLIW processor that includes floating point execution units is described by R. K. Montoye, et al. in "Design of the IBM RISC System/6000 floating point execution unit", IBM J. Res. Develop., V. 43 No.1, pp. 61–62, January 1990. Additional examples are provided in U.S. Pat. No. 5,418,975, the content of which is incorporated herein for all purposes.

In accordance with a preferred embodiment of the present invention, the system can be implemented as a plurality of independent execution units using VLIW architecture processing. Multi-tasking capabilities can also be used to exploit the inherent structure of the input data in alternate embodiments.

6.5. Experimental Results

The following experiments have been conducted with software implementing the Bayesian estimation described in the previous sections. In each case, reported is the number of cut sites, molecules, the quality measure, the digest rate, and cut site standard deviation reported by the software. The map error displays either the RMS error between the map reported by the software and the correct map known by some independent technique (for example, complete sequencing, if available) in those cases where the software found the right number of cut sites. Otherwise, the software indicates that the map found is unacceptable.

6.5.1. Lambda Bacteriophage DNA (I)

Deposited manually using the "peel" technique. Correct map known from sequence data.

TABLE 1

| R. Enzyme | Cuts | Mols | Quality | Digest rate | Cut SD | Map Error | |
|---|---|---|---|---|---|---|---|
| Sca I | 6 | 292 | 100% | 35% | 1.82% | 0.66% | |
| Ava I | 8 | 504 | 99% | 32% | 1.66% | 0.83% | (FIG. 4) |

6.5.2. Lambda Bacteriophage DNA (II)

Deposited mechanically (by a robot) as a grid of spots, each spot producing an independent map. Correct map known from sequence data.

TABLE 2

Map computed using the Bayesian approach. Correct ordered restriction map (from sequence data) for the Lambda Bacteriophage DNA (I) with Ava I is: (0.09732, 0.39992, 0.43295, 0.57497, 0.065187, 0.69065, 0.78789, 0.82240).

```
molecules = 504, cuts = 1441, uncut molecules = 39, best 3 maps:
map1:cuts = 8, P = 99.535%, good mols = 79.41%, digest rate = 0.3251, false
cuts = 0.3315, SD = 0.0166
9 frags    0.09507  0.31530  0.03891  0.13294  0.07145  0.04462  0.08265  0.3984  0.17923
8 cuts     0.09507  0.41037  0.44928  0.58221  0.65366  0.69828  0.78093  0.82077
cut SDs    0.01423  0.01653  0.01663  0.01786  0.01689  0.01823  0.01782  0.01482
counts     152.4    118.9    116.9    113.0    137.4    123.1    112.9    146.1
map2:cuts = 9, P = 0.4646%, good mols = 79.99%, digest rate = 0.2860, false
cuts = 0.3458, SD = 0.0150
10 frags   0.9503   0.31652  0.03876  0.12911  0.5924   0.03397  0.03859  0.07162  0.03849
           0.17867
9 cuts     0.09503  0.41155  0.45031  0.57942  0.63866  0.67263  0.71122  0.78284  0.82133
cut SDs    0.01319  0.01488  0.01488  0.01513  0.01658  0.01360  0.01690  0.01563  0.01370
counts     147.3    115.8    110.3    122.8    93.1     107.7    89.9     110.5    140.6
map3:cuts = 10, P = 0.0000%, good mols = 75.70%, digest rate = 0.2596,
false cuts = 0.03445, SD = 0.0133
11 frags   0.09489  0.31828  0.3800   0.11818  0.02946  0.04939  0.02851  0.03574  0.07067
           0.03786  0.17902
10 cuts    0.09489  0.41317  0.45117  0.56935  0.59881  0.64820  0.67671  0.71245
           0.78312  0.82098
cut SDs    0.01198  0.01335  0.01366  0.01294  0.01406  0.01344  0.01261  0.01549
           0.01407  0.01245
counts     136.5    108.3    99.2     78.6     74.3     88.1     13.1     77.9     101
           132.7
RMS Map Error = 0.00826 (relative to map1)
```

TABLE 3

Map computed using the Bayesian approach. Correct ordered restriction map (from sequence data) for the Lambda Bacteriophage DNA (II) with BamH I is: (0.13960, 0.28870, 0.42330, 0.53930, 0.88650)

```
molecules = 215, cuts = 523, uncut molecules = 34, best 3 maps:
map1:cuts = 5, P = 100.0000%, good mols = 60.4%, digest rate = 61.4%, false
cuts = 0.14, SD = 0.0119
6 flags     0.14016   0.14444  0.13700   0.11331   0.35012   0.11496
5 cuts      0.14016   0.28461  0.42161   0.53492   0.88504
cut SDs     0.01166   0.01110  0.01180   0.01245   0.01232
counts      62.0      75.3     92.2      86.6      59.9
map2:cuts = 6, P = 0.0000%, good mols = 60.0%, digest rate = 48.0%, false
cuts = 0.13, SD = 0.13, SD = 0.0118
7 flags     0.13921   0.14449  0.13165   0.01029   0.10845   0.35102  0.11489
6 cuts      0.13921   0.28370  0.41536   0.42564   0.53409   0.88511
cut SDs     0.01155   0.01102  0.01137   0.01188   0.01261   0.01207
counts      58.8      70.1     45.0      47.1      79.6      56.9
map3:cuts = 6, P = 0.0000%, good mols = 60.0%, digest rate = 48.0%, false
cuts = 0.15, SD = 0.0113
7 flags     0.13932   0.14426  0.13178   0.10475   0.01688   0.34333  0.11428
6 cuts      0.13932   0.28358  0.42076   0.52551   0.54239   0.88572
cut SDs     0.01138   0.01072  0.01177   0.01150   0.01108   0.01180
counts      58.9      70.3     85.2      42.1      42.1      56.0
RMS MAp Error = 0.00287 (relative to map1)
```

| R. Enzyme | Cuts | Mols | Quality | Digest rate | Cuts SD | Map Error | |
|---|---|---|---|---|---|---|---|
| BamH I | 5 | 203 | 37% | 42% | 2.82% | 1.07% | |
| BamH I | 5 | 160 | 100% | 45% | 2.35% | 0.98% | |
| BamH I | 5 | 257 | 100% | 58% | 1.74% | 0.79% | |
| BamH I | 5 | 215 | 99% | 50% | 2.61% | 0.43% | |
| BamH I | 5 | 215 | 100% | 61% | 1.19% | 0.29% | (FIG. 5) |
| BamH I | 7 | 175 | 9% | 24% | 2.25% | Wrong Map | |

TABLE 4

Map computed using the Bayesian approach. Correct fingerprint (from gel electrophoresis) for the Human cosmid Clone with Mlu I is: (0.09362, 0.09974, 0.12643, 0.21862, 0.26396). This fingerprint omits one small (<1 kB) fragment. The correct ordered restriction map consistent with the fingerprint data is: (0.21862, 0.48258, 0.57620, 0.67594, 0.87357).

```
molecules = 745, cuts = 1755, uncut molecules = 66, best 3 maps:
map1:cuts = 5, P = 99.8579%, good mols = 80.25%, digest rate = 0.3696, false
cuts = 0.5325, SD = 0.0277
6 flags      0.21919   0.26956  0.09810   0.09723   0.18784   0.12808
5 cuts       0.21919   0.48875  0.58685   0.68408   0.87192
cut SDs      0.02782   0.03030  0.02472   0.08297   0.02748
counts         210.3     194.2    278.6     218.6     203.1
map2:cuts = 6, P = 0.1421%, good mols = 77.15%, digest rate = 0.3064, false
cuts = 5343, SD = 0.0250
7 flags      0.21963   0.26424  0.08223   0.03746   0.08386   0.18410  0.12848
6 cuts       0.21963   0.48387  0.56610   0.60356   0.68748   0.87152
cut SDs      0.02525   0.02600  0.02454   0.02355   0.02561   0.02487
counts         188.1     160.7    167.6     173.2     185.9     181.1
map3:cuts = 7, P = 0.0000%, good mols = 90.61%, digest rate = 0.2513, false
cuts = 0.5985, SD = 0.0241
8 flags      0.21327   0.27029  0.08288   0.03357   0.07312   0.06696  0.13289
7 cuts       0.21327   0.48356  0.56644   0.60002   0.67314   0.74009  0.87298
cut SDs      0.02475   0.02501  0.02392   0.02221   0.02226   0.02620  0.02468
counts         183.0     166.4    169.0     176.4     175.9     125.7    191.2
RMS MAp Error = 0.00665 (relative to map1)
```

6.5.3. Human Cosmid Clones

Using a cosmid vector and deposited as a grid of spots. Map verified by contig and gel electrophoresis as having 6 cuts, with one small fragment (<1 kB, and optically undetectable in most of the images) missing [marked (*) in the table below]. Note that the first two rows are the same experiment returning two equally likely answers.

TABLE 5

| R. Enzyme | Cuts | Mols | Quality | Digest rate | Cut SD | Map Error | |
|---|---|---|---|---|---|---|---|
| Mlu I | 6 | 749 | 50% | 38% | 2.77% | (*) | |
| Mlu I | 5 | 649 | 50% | 31% | 2.50% | 0.61% | |
| Mlu I | 6 | 960 | 100% | 50% | 2.22% | (*) | |
| Mlu I | 5 | 957 | 72% | 26% | 2.83% | 1.45% | |
| Mlu I | 5 | 745 | 99% | 37% | 2.77% | 0.67% | (FIG. 6) |
| Mlu I | 10 | 852 | 8% | 14% | 2.64% | Wrong Map | |

7. EXAMPLE

Nick Translation of Single Dna Molecules

The following example describes experiments demonstrating that ordered restriction endonuclease maps of DNA molecules can be constructed using fluorescence microscope images of individual, restriction endonuclease digested DNA molecules. This example also demonstrates that solid-surface mounted double stranded DNA molecules can serve as substrates for nick translation by DNA Polymerase I.

7.1. Materials and Methods

Derivatized Glass Surface Preparation

Glass coverslips were cleaned by boiling in concentrated nitric acid (6 hours) and then in 6 M hydrochloric acid (12 hours), followed by a thorough rinse in high purity water. Surfaces were derivatized according to three protocols: (i) incubating in ethanol containing 10.8 $\mu$M APTES (Aldrich Chemical) (30 $\mu$l of a 2% aqueous solution of APTES, hydrolyzed for 7 hours at room temperature in 250 ml ethanol) at 25° C. for 48 hours; (ii) incubating in a 6 mM aqueous solution of APTES (pH 3.45) at 50° C. for 20 hours; and (iii) incubating in a 2.5 nM aqueous solution of [3-(triethoxysilyl-propyl]trimethylammonium chloride (TESP; Aldrich Chemical) (150 $\mu$l of a 65% aqueous solution of TESP, in 150 ml of high purity water) at 65° C. for 12–16 hours.

Fixation of Arrayed DNA Samples

DNA molecules were elongated and aligned in square arrays by spotting droplets of DNA solution onto derivatized glass surfaces, followed by air drying, using an Eppendorf micro-manipulator in combination with an x-y table (interfaced to an Apple Macintosh computer) controlled by microstepper motors. Although this instrument is not rapid, it is very precise and reproducible. A glass capillary tube (500 $\mu$m, i.d.) was used to draw DNA samples and then spot onto derivatized glass surfaces by simple contact. Each spot was typically 900 $\mu$m with a spot to spot variation of ±100 $\mu$m. The center-to-center spacing between spots was 1.5 mm controlled by computer program settings of the micromanipulator, and x-y table combination. Spots were deposited at the rate of one spot every two seconds.

Other grids were generated by using a modified commercially available laboratory automation robot equipped with a 500 $\mu$m i.d. stainless steel capillary pipetting tool, and a specialized workspace deck capable of holding multiple 96 well microtiter plates and up to 12 optical mapping surfaces in a vacuum chuck. In this configuration, the robot was able to deposit one sample approximately every 10 s. Fluid droplets (5–50 pg/μl DNA in Tris-EDTA buffer) of 10–20 nl were spotted onto open glass surfaces (using several customized spotting engines) that had been derivatized with APTES or TESP.

Spot diameters were reproducible and were varied from 500–1,000 μm by changing the width of the spotting tool—a glass capillary or cut-off stainless steel syringe needle. Since lambda bacteriophage or cosmid clones have a typical contour length of about 17 μm, it can be possible to create spots having diameters two, or three times as large, or approximately 50 μm across. Using small spotting tools, such spots were made. However, the most satisfactory spots, in terms of facile mapping, were made with 500–900 μm diameters spots, with densities of 100 clones gridded onto a single 18×18 mm derivatized glass surface.

Images of gridded DNA spots (FIG. 1) show that they are uniform, round and consistently packed, containing a high percentage of fully elongated DNA molecules.

Fluid Fixation

Figure 12A:
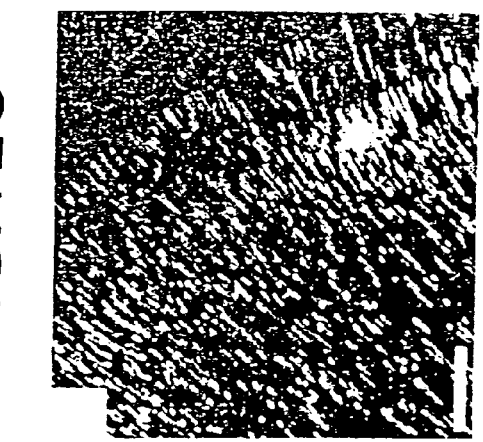
Figure 12B:
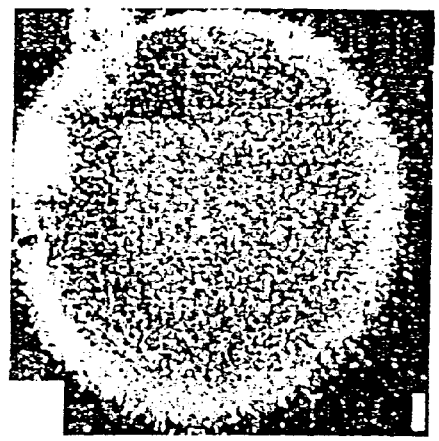
Figure 12C:
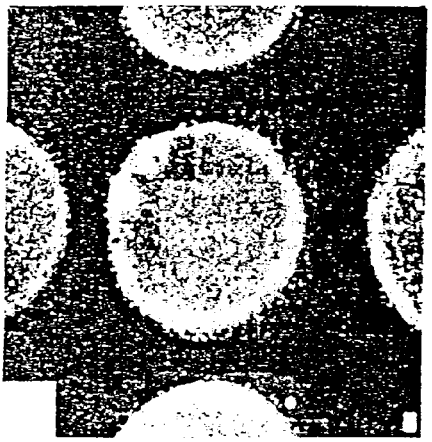
Figure 12D:
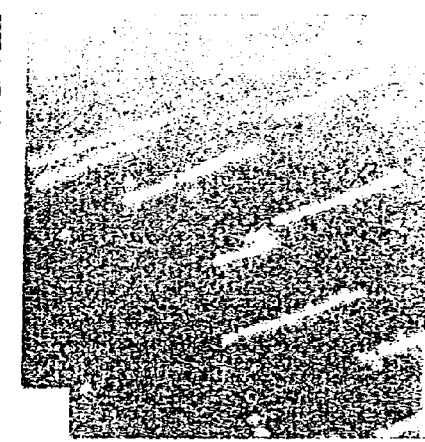
Figure 12E:
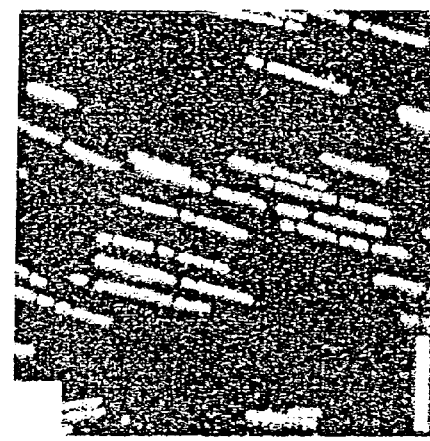
Figure 12F:
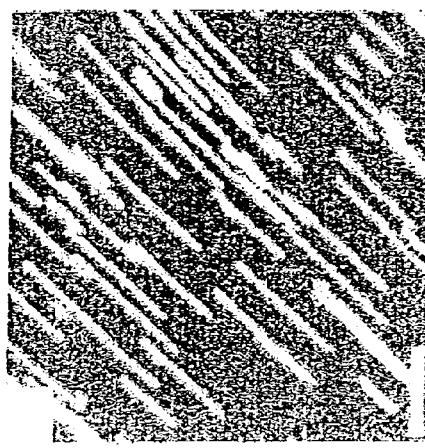
Figure 13A:
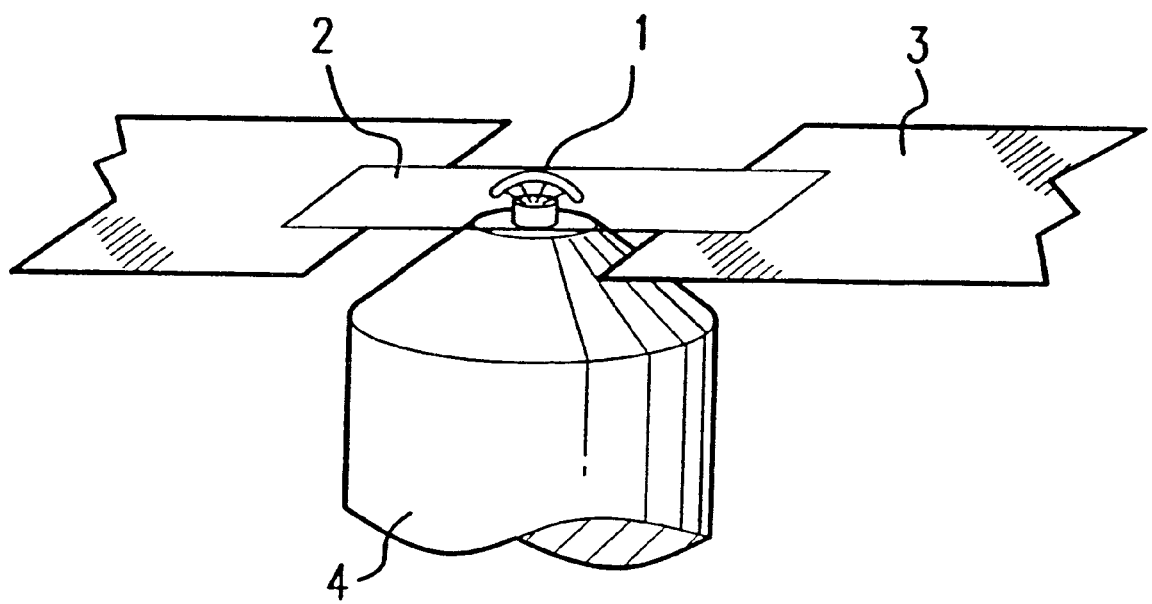
Figure 13B:
Figure 13C:
Figure 13D:
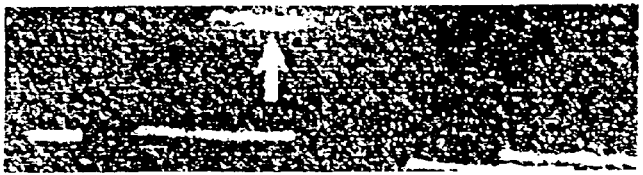
Figure 13E:
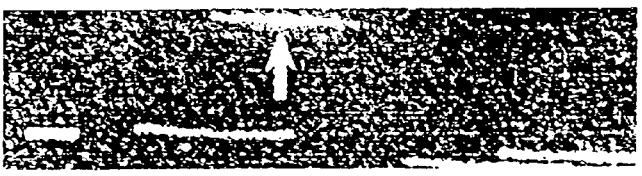
Figure 13F:
Figure 13G:
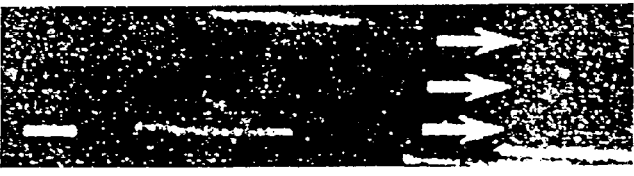
Figure 13H:
Figure 13I:
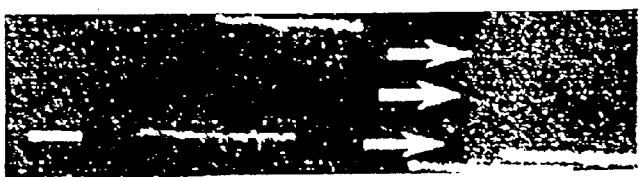
Figure 13J:

When the spotted droplets dried, a significant number of fixed DNA molecules were fully elongated, aligned radially, and concentrated near the spots' peripheries, making a "sunburst" pattern (FIGS. 12B–D). This fluid fixation effect, unlike molecular combing (Michalet et al., 1997, Science 277:1518; and Bensimon et al., 1994, Science 265:2096–2098), does not require deliberate end-tethering to elongate molecules. Addition of either glycerol or other polyalcohol "dopants" to the spotting solutions consistently maximized the elongation and alignment of molecules and minimized overlapping (FIG. 12), greatly facilitating image processing and analysis. No further procedures were needed to elongate the fixed molecules and, importantly, rehydration of spotted DNA samples with restriction endonuclease buffer (low, medium, or high salt) effectively restored biochemical activity since molecules could be digested with BamH I (FIG. 1) and Ava I (FIG. 1).

The mechanisms underlying the effect are numerous and complex. We modeled droplet drying mathematically. Given the similarity between coffee drop drying (Deegan et al., 1997, Nature 389:827–829) and fluid fixation of DNA, our analysis is partially derived from early discussion with Todd F. Dupont at the University of Chicago. Droplet drying occurs in two phases: first, the droplet flattens until some critical contact-angle is reached; second, the contact-line recedes (Deegan et al., 1997, Nature 389:827–829; Chen et al., 1991, J. Phys. Chem. 95:10736–10747; and Rowan et al., 1995, J. Phys. Chem. 99:13268–13271). In phase one, net flow is radially outward, with mean velocity v, which satisfies $$\frac{dv}{\left[v - 2v_o\left(1 - \frac{r^2}{4r_0^2}(1+\cos\theta)\right)\right]} = \frac{1}{(1-\cos\theta)} d\ln\left[\frac{r_0^2}{r_0^2 - k^2 r^2}\right]$$

and may explain the accumulation of small molecules at the periphery of the spot. Here the contact angle q is assumed small, $k^2=(1+\cos q)(2-\cos q)/2$ and v is flow velocity averaged over the thickness of the spot at radius r. The velocity scale $v_0 = l/2\Pi r_0,$ where, as in Rowan et al. (1995, J. Phys. Chem. 99:13268–13271), $r_0$ is the initial radius of the spot and l is the evaporation rate per unit area.

Video Microscopy of Fluid Fixation

Molecular fluid fixation events were imaged by video microscopy of stained DNA molecules during droplet drying. Profound changes in molecular length distributions and deposition patterns correlating with variations in spot geometry were observed. Surprisingly, we observed that molecules elongate and fix to the surface before phase two, when the receding contact-line sweeps past them (FIG. 13). Intending not to be limited to a particular mechanism of action, this data suggests that high-shear fluid flows stretch molecules at least partially before they adhere to the positively charged surface. Rapid flows near the surface probably extend the molecules completely as they begin to adsorb. This mechanism of elongation stands in contrast with fluid meniscus based techniques (molecular combing) where molecules attach at one end and elongate in the fluid-air interface that sweeps past as drying occurs (Bensimon et al., 1994, Science 265:2096–2098).

Evaluation of Molecular Parameters and Sizing Error

Surface characteristics were systematically varied to balance molecular adsorption with biochemical accessibility (Cai et al., 1995, Proc. Natl. Acad. Sci. USA 92:5164–5168; Craig et al., 1990, Nucl. Acids Res. 18:2653–2660; and Nizetic et al., 1991, Proc. Natl. Acad. Sci. USA 88:3233–3237). Excessively strong adsorption prevents molecular elongation, while weak adhesion does not fix a sufficient number of molecules to the surface.

The distribution of molecular lengths for human adenovirus type 2 DNA molecules from eleven spots verified a high percentage of elongated molecules (FIG. 1). No molecules appeared to be elongated longer than the full contour length of 12.3 μm even though intercalation is expected to elongate the DNA somewhat (Spielmann et al., 1995, Biochem. 34:8542–8553 and Larsson et al., 1994, J. Am. Chem. Soc. 116:8459–8465). Longer objects all proved to be software generated artifacts. The fraction of unstretched molecules varied with fixation conditions. Since optical mapping measures relative fluorescence intensity to determine restriction fragment masses, complete molecular elongation is not essential for accurate map construction. However, a narrow and reproducible distribution of elongated molecules does facilitate sizing restriction fragments by length (Meng et al., 1995, Nature Genet. 9:432–438). Typically, the periphery of the spot generally contained a higher percentage of stretched molecules than the interior (38% elongated in the outer annulus versus 30% in the core for this case). This data underrepresents the proportion of elongated molecules in the outer annulus due to difficulty in automatically scoring the densely arrayed molecules which predominate in that region.

Restriction Endonuclease Digestion of Surface-Fixed DNA Molecules

Surface-fixed molecules were digested by adding 40 μl of 1× restriction buffer (manufacturer recommended) containing 10–20 units of the corresponding restriction endonuclease per spotted surface. Surfaces were incubated in a humidified chamber for 15 minutes to 2 hours, depending upon the surface condition. After digestion, the overlaying buffer was removed with an aspirator, washed with high purity water, stained with YOYO-1 fluorochrome (100 nM in 20% β-mercaptoethanol; Molecular Probes) and sealed with Cargille immersion oil to prevent drying.

Microscopy and Imaging of Surface-Fixed DNA Molecules

Automatic imaging workstations were built around Zeiss 135 inverted microscopes equipped for epifluorescence, with 100× Zeiss plan-neofluor oil immersion objectives, numerical aperture 1.3 and fluorescein band pass filter pack (485/505/530 nm). Microscopes were also equipped with a Dage SIT68GL low light-level video camera for acquiring focus, and a Princeton Instruments cooled CCD digital camera (1316×1032 pixels, KAF 1400 chip, 12 bit digitization) for high resolution imaging and photometry. A Ludl Electronics x-y microscope stage with 0.1 µm resolution was used for translation.

DNA molecules were imaged using OMM software which integrates all the workstation functions such as the movement of the microscope stage, focus, and image collection. Control of light path actuators, video autofocus and sample translation (x-y stage) was accomplished by a Ludl Electronics MAC 2000 interface bus with the following modules installed: PSSYST 200, MCMSE 500, MDMSP 503, AFCMS 801, FWSC 800, and RS232INT 400. The Ludl MAC 2000 was interfaced via RS232 serial connection to a Sun Microsystems SPARC 20 dual processor computer workstation. The Princeton Instruments CCD camera was also interfaced, via a Pentium-based microcomputer controller and distributed network, to a Sun workstation. Software for control of the above peripherals was written in the C programming language.

Digital images can be acquired by the workstation at the rate of 4 per min (using 10 s imaging time), and stored on hard disk arrays for later image processing and extraction of restriction map data. The OMM system runs on a network of 15 identical dual processor Sun SPARC 20 workstations with a networked file system.

Access to all aspects of the OMM data and processing is made through one shared directory hierarchy. This file system structure and the accompanying software libraries provide uniform controlled access to all collection and processing activities and data. A distributed processing system has been developed which allows all the available computational resources on the network to be shared.

Automation of Image Acquisition, Processing and Map Construction

An integrated microscope control, machine vision, and statistical analysis system, or Optical Mapping Method ("OMM"), was developed to fully automate image collection, processing, and map construction. The computer control system advances samples for image acquisition and accumulates image files for subsequent analysis.

Ordered restriction maps are derived from digital images of fully and partially digested molecules through three computational stages: First, image regions containing fragments from one molecule are identified for analysis. Second, a "backbone" of each molecule is calculated and the intensity along it used to identify enzyme cut sites and the relative mass of fragments between cut sites. OMM uses an advanced implementation of restriction fragment fluorescence intensity measurement (Schwartz et al., 1993, Science 262:110–114) to determine the relative mass of fragments. Third, using accumulated data from all images of the same sample, a final map is computed using Bayesian estimation (Anantharaman et al., 1997, J. Comp. Bio. 4:91–118).

To test the sizing accuracy of optical mapping, we used OMM to construct ordered restriction maps of lambda bacteriophage DNA, whose nucleotide sequence is known. FIG. 1 shows the relative fluorescence intensities of restriction fragments ranging in size from 1,602–21,226 bp, plotted against restriction fragment sizes determined from the known sequence. The fragment sizes determined by fluorescence agreed with the fragment sizes from the known sequence with an average error relative to sequence-determined sizes of 217 bp. The pooled SD was 958 bp. This reflects the precision of measurements of individual molecules. Each optical map was generated from 10–40 image fields, which were collected from one digested DNA spot. These data indicate that optical size measurements are comparable in accuracy to measurements obtained from agarose-gel electrophoresis.

To determine the consistency of enzymatic cleavage over many gridded samples, we evaluated the distribution of BamH I cutting efficiencies over a 9×9 grid of human adenovirus type 2 DNA by tabulating the total number of scored cleavage sites per molecule. OMM found restriction maps for 64 contiguous spots from the center of the 9×9 grid. Some of the spots on the periphery of the 9×9 grid failed to yield restriction maps, due to uneven derivatization effects near the edges of the optical mapping surface. The distribution of the relative errors of the 64 restriction maps was narrow (average 2.9%, standard deviation ("SD") 2.5%). The Bayesian estimate of the precision of individual fragment sizes was 1.6 kb and the estimate of cutting efficiency per restriction site was 73%. These cutting efficiencies are typically 30% lower than the actual number since OMM automatically discards some molecules from the analysis that would otherwise be manually scored. Cutting efficiencies are Bayesian estimates. Molecules with scored cuts can be rejected completely (modeled as impurities) if the cuts are inconsistent with the consensus map, or individual cuts can be rejected (modeled as false) if some of the cuts are consistent and some are not. The rejection rate for molecules which already passed the morphology tests was 22% (SD 10%) and the number of false cuts per molecule was 0.32 (SD 0.12). Other runs showed similar results.

7.1.1. Nick-Translation of Surface-Fixed DNA Molecules

The TESP treated surface, spotted with lambda bacteriophage DNA molecules, was washed twice with nick translation buffer (1× E. coli DNA polymerase I buffer, 50 mM dNTPs, 5% glycerol and 100 mg/ml BSA). Fifty µl of nick translation buffer containing 10 mM R110-dUTP (fluorochrome labeled nucleotide; Perkin Elmer), 5 ml of 10 ng/ml DNase and 0.5 units of DNA polymerase I (Boehringer Mannheim) was pipetted onto the surface and incubated in a sealed humidified chamber (16° C. overnight). The reaction solution was aspirated off the surface which was then incubated in excess Tris-EDTA buffer for 20 min, rinsed with high purity water, and air dried. The surface was mounted on a microscope slide with 3 µl of 20% β-mercaptoethanol in Tris-EDTA and sealed with immersion oil. R110-dUTP labeled or counterstained samples were imaged using the fluorescein band pass and a 580/600/630 nm filter pack. DNA was counterstained with 3.5 µl of YOYO-3 fluorochrome (100 nM in 40% β-mercaptoethanol, 1% DMSO).

7.2. Results

Figure 15A:
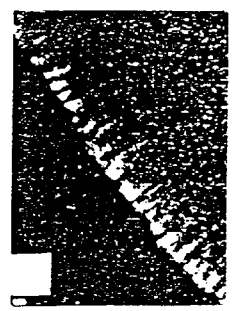
Figure 15B:
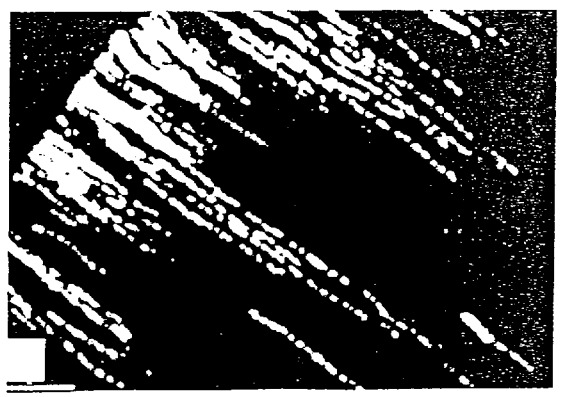
Figure 15C:

Nick Translation Labeling of Fluid Fixed Lambda Bacteriophage DNA Molecules To determine whether surface fixed molecules might serve as substrates for other DNA modification enzymes, such as DNA ligases or polymerases, a series of nick translation reactions were performed on surface fixed lambda bacteriophage DNA using *E. Coli* DNA polymerase I and fluorochrome labeled nucleotides. This experiment is similar in concept to primed in situ synthesis ("PRINS") performed on fixed intact chromosomal spreads (Koch et al., 1989, Chromosoma 98:259–265). Fluorescence signals detected along molecule backbones indicated the addition of labeled nucleotide (FIGS. 15A and 15B). Labeled nucleotide addition was consistent over most of the DNA backbones, except for numerous small gaps. FIG. 15C shows additional molecules counterstained with YOYO-3 to confirm nick translation results and to determine that the vast majority of gaps corresponded to unlabeled regions and not double-stranded breaks.

8. EXAMPLE

DNA Polymerase I Action and Products on Surface Mounted DNA

The following example describes experiments demonstrating that DNA Polymerase I is capable of adding fluorescently labeled nucleotides by nick translation of surface-mounted DNA molecules and as few as one fluorochrome is readily imaged.

8.1. Materials and Methods

8.1.1. Preparation of Modified Glass Surfaces

The materials and methods for elongation and fixation of DNA molecules were simple modifications of those previously described (Cai et al., 1995, Proc. Natl. Acad. Sci. USA 92:5164–5168 and Meng et al., 1995, Nature Genet. 9:432–438). Glass surfaces (22×22 mm cover slips, Premium Brand; Fisher Scientific, Pittsburgh, Pa.) for surface nick translation and optical mapping were first cleaned and protonized by boiling ~200 surfaces (unracked, but individually deposited into the boiling acid) in 1.8 to 2 l of 4 M HCl for 4 to 6 hours. Cleaned cover slips were rinsed thoroughly with high purity water until the acid was neutralized and stored in high purity water.

The coverslips were then modified by either aminopropyltriethoxylsilane (APTES) or N,N,N-trimethyl-trimethoxylsilylpropylamino chloride (TSPAC) as follows. 0.1 M APTES stock solutions were made by dissolving 4.20 g of APTES (Aldrich, Milwaukee, Wis.; no further purification) in 200 ml of high purity water and adjusting the pH to 3.50 by 3 M and 0.3 M HCl and were stored in polypropylene bottles at −70° C. 0.01 M treatment of APTES solutions for 40–50 individually racked surfaces were made by diluting 20 ml of the stock solution in 180 ml of high purity water and incubating at 50° C. for 16 hours. After treatment, the surfaces were thoroughly rinsed with high purity water and air dried. APTES treated surfaces were used within 4 days of derivatization for predictable DNA fixation.

TSPAC solutions were made by dissolving 250 to 750 μl of TSPAC stock solution (65% water solution from Aldrich, without further purification) in 200 ml of high purity water to derivatize 40 surfaces at 65° C. for 18 hours. Surfaces were then washed thoroughly with high purity water and stored in closed containers.

8.1.2. Elongation and Fixation of DNA Molecules on Modified Glass Surfaces The majority of the experiments were done by fixing DNA using a simple adaptation of methods previously described for optical mapping (Cai et al., 1995, Proc. Natl. Acad. Sci. USA 92:5164–5168 and Meng et al., 1995, Nature Genet. 9:432–438). Briefly, 2.5 μl of 0.1 ng/μl lambda bacteriophage DNA (New England Biolabs, Beverly, Mass.) solution was deposited on one side of a precleaned microscope slide (3"×1"×1 mm; Fisher Scientific) and the silane modified surfaces were placed so that one edge touched the DNA solution first. Diffusion toward the other edges of the sandwich produced unidirectional fluid flows which elongated molecules into parallel arrays, fixed onto the derivatized surface (FIG. 16). Unlike molecular combing (Bensimon et al., 1994. Science 265: 2096–2098), this approach does not end-tether molecules for elongation.

Molecules were also elongated and fixed onto surfaces by depositing small droplets (~0.2 to 0.5 μl) of DNA solution (0.01 ng/μl), using a glass capillary, onto derivatized surfaces (as described in Section 7.1).

8.1.3. Labeling of DNA with Fluorochrome Tagged Nucleotides by PCR

A set of primers for a PCR product (500 bp) using a lambda bacteriophage DNA templates was verified by amplification without added labeled deoxyuridine triphosphate (dUTP): 5'-GAT GAG TTC GTG TCC GTA CAA CTG G (forward) SEQ ID NO:1, and 5'-GGT TAT CGA AAT CAG CCA CAG CGC (reverse) SEQ ID NO:2. Additional amplified products, 2.8 and 5.3 kb, were derived from the universal insert amplification primer pairs on pBluescriptII KS: 5'-GTA AAA CGA CGG CCA GT (forward) SEQ ID NO:3, and 5'-AAC AGC TAT GAC CAT G (reverse) SEQ ID NO:4. Three differently fluorochrome-labeled deoxyuridine triphosphates (F-dUTPs) were used for labeling products: R110-dUTP, R6G-dUTP and TAMRA-dUTP (PE Applied Biosystems, Foster City, Calif. according to Fluorescent deoxynucleotide triphosphate F-dNTP Reagents, Protocol 402774, 1996). All F-dUTPs behaved similarly; R110-dUTP was used for most experiments. The concentration of deoxythymidine triphosphates (dTTPs) in all the PCR reactions was fixed at 100 mM, and differing amounts of F-dUTP were added to vary the molar dTTP/F-dUTP ratios of the labeled PCR products: 5/1, 10/1, 20/1 and 50/1. PCR products were purified by agarose gel electrophoresis. Labeled product bands were clearly visible in the gel on a 254 nm UV transilluminator without staining with ethidium bromide. The visible colours of these gel bands were: R110, green; R6G, yellow-green, and TAMRA; orange. Product bands were excised, melted and extracted with a phenol, phenol-chloroform, and chloroform series.

8.1.4. Evaluation of Nick Translation Conditions

Conditions for nick translation were first evaluated by conventional means before optical mapping. 50 μl, reactions contained: 2 μg of lambda DNA, 1× DNA polymerase I buffer (New England Biolabs, Beverly, Mass.), 50 μM dNTPs, 100 μg/ml BSA, 5 μl of 10 ng/ml DNase I in 50% glycerol, 0.5 units of DNA polymerase I (New England Biolabs, Beverly, Mass. or Boehringer Mannheim, Indianapolis, Ind.), and dTTP/F-dUTP in ratios 4/1, 10/1, 20/1, and 50/1. Reactions were incubated at 16° C. for 3 to 4 hours, then purified through a NUNCCOLUMN™ (Stratagene, La, Jolla, Calif.) to eliminate unincorporated F-dUTP. Purified products were diluted to approximately 0.15 ng/μl and fixed onto surfaces.

The amount of DNAse I used for nick translation was critically optimized. Nick translation reactions using lambda bacteriophage DNA were performed at 16° C. for 3–4 hours and stopped by adding EDTA (pH 8) to a final concentration of 50 mM, and transferred to ice before column purification or analysis by gel electrophoresis. The F-dUTP labeled nick translation products were analyzed by alkaline agarose gel electrophoresis after heat-denaturation to evaluate the product size distribution. The DNase I concentration of 1 ng/ml was chosen for subsequent nick translation reactions on surfaces since it produced a probe size distribution of 300 bp-2 kb, as is normally used for fluorescence in situ hybridization procedures (Keller et al., 1993, *DNA Probes* Stockton Press, New York and references therein). Labeled molecules were also imaged by fluorescence microscopy using methods described here to confirm gel electrophoresis results.

8.1.5. Surface Nick Translation with Labelled Nucleotides

DNA molecules were fixed onto the modified glass surfaces by the methods described above and in FIG. 16. Surfaces used for nick translation were washed twice (5 min each) with 100 µl of nick translation buffer (1× buffer for DNA polymerase 1, New England Biolabs, containing 50 µM dNTP, 5% glycerol and 100 µg/ml BSA) followed by aspiration. 50 µl of nick translation reaction mix (1× DNA polymerase buffer, plus 50 µM dNTP, 10 µM R110-dUTP, 100 µg/ml BSA, 5 µl of 10 ng/ml DNase I in 50% glycerol, and 0.5 units of DNA polymerase I) was pipetted onto the surface and incubated in a humidified chamber at 16° C. overnight. Reactions were stopped by aspirating off the overlaid solution, then washing in TE buffer for 20 min, rinsing with high purity water, and drying at ambient conditions.

8.1.6. Imaging Labelled PCR Products and Surface Nick Translation

All samples were viewed on a Zeiss Axiovert 35 fluorescence microscope coupled to a cooled CCD camera (Photometrics, Tucson, Ariz.) for image acquisition and a silicon intensified target (SIT) camera for focusing. Digital images were analyzed by a commercial program, IP Lab (Signal Analytics, Vienna, Va.). Images were digitally flattened to eliminate illumination shading effects. Fluorescence intensity measurement techniques used are previously described (Cai et al., 1995, Proc. Natl. Acad. Sci USA 92:5164–5168). Photobleaching was attenuated by addition of 4 µl of 30% β-mercaptoethanol in water to each surface and sealed with objective oil to prevent evaporation, just prior to imaging. R110-dUTP labeled PCR products were imaged using a YOYO-1 band-pass filter (XF22; Omega Optical, Brattleboro, Vt.). For samples too dim to image with a SIT camera, visible targets were added: fluorescence beads (carboxylated red fluorescence labelled latex beads, 0.03 µm in size; Molecular Probes, Eugene, Oreg.). The fluorescence beads were easily visible with an ethidium-homodimer band-pass filter pack (Omega Optical) but invisible through a YOYO-1 optical filter pack.

8.1.7. Quantitation of Nick Translation Addition

The fluorescence intensity from surface nick translation labeling was quantitated by calculating the total fluorescence intensity from individual DNA molecules. Images were acquired using IPlab image processing program running on a Macintosh computer, then transferred to SUN SPARC 20 Workstation for image flattening and bright field correction (Cai et al., 1995, Proc. Natl. Acad. Sci. USA 92:5164–5168). Images were then transferred back to the Macintosh for fluorescence intensity measurements using IPlab. The DNA concentration used was carefully monitored to ensure optimal spacing between individual DNA molecules, making them easily distinguishable. The individual DNA backbone overlays were manually marked in IPlab, and the fluorescence intensity of each DNA molecule were calculated by summing all molecule pixels values after background subtraction.

8.2. Results

8.2.1. Imaging PCR Products

To determine the limits of fluorochrome detectability given a standard fluorescence microscope and a low-noise cooled CCD camera, it was necessary to firmly establish the number of fluorochromes detectable in order to confidently detect and quantitate nick-translation products from surface mounted molecules. To accomplish this, a set of PCR primers was designed to yield a series of differently sized products from lambda DNA and varied the ratio of dTTP/F-dUTP used in the amplification mix. In this way, we could evaluate fluorochrome detectability for both number and density.

These experiments, utilized fluorochrome labeled nucleotides (F-dUTP and fluorochrome-labelled deoxycytidine triphosphate; F-dCTP) produced by Perkin Elmer following evaluation of numerous and similarly labeled nucleotides from other manufacturers. The Perkin Elmer compounds were found to be satisfactory in terms of fluorescent yields and polymerase activity. The PCR reactions were performed using a series of dTTP/F-dUTP concentrations (4/1, 10/1, 20/1 and 50/1) as part of the total reaction mix (see Section 7.1).

As expected, PCR product yields decreased with increasing F-dUTP concentration (Doublie et al., 1998, Nature 391:251–258); however, for short products, 500 bp in size, a dTTP/F-dUTP ratio of 4/1 proved acceptable. Longer products, approximately 5 kb in size, gave meager yields even when the unlabeled nucleotide concentration was 10 fold higher, perhaps due to augmented chain termination by F-dUTP. All products were analyzed by gel electrophoresis, and most products were directly visible using 254 nm illumination, without further staining by ethidium bromide. Such bands were carefully excised from agarose gels, purified by phenol extraction and mounted onto derivatized glass surfaces (Cai et al., 1995, Proc. Natl. Acad. Sci. USA 92:5164–5168 and Meng et al., 1995, Nature Genet. 9:432–438).

Mounted molecules were imaged using standard optical mapping techniques (Cai et al., 1995, Proc. Natl. Acad. Sci. USA 92:5164–5168 and Meng et al., 1995, Nature Genet. 9:432–438; and Jing et al., 1998, Proc. Natl. Acad. Sci. USA, vol. 95, in press) and presented an interesting array of morphologies (see FIG. 17). For example, a 500 bp PCR product has a polymer contour length of approximately 170 nm, assuming B-DNA, which is near the resolution of light microscopy. Thus, such products appear as fluorescent points, and no detailed morphology can be ascertained (Smith et al., 1961, J. Opt. Soc. Am. 51:412–414). However, these products serve as ideal fluorescent targets to evaluate fluorochrome number detectability, since target size remains constant, and fluorochrome number is conveniently varied by alterations to the PCR nucleotide mix. Longer PCR products appeared as conventionally stained molecules normally imaged by optical mapping (Cai et al., 1995, Proc.

Natl. Acad. Sci. USA 92:5164–5168 and Meng et al., 1995, Nature Genet. 9:432–438).

Fluorescence microscopy imaging of 500 bp PCR products amplified from reaction mixes containing various dTTP/F-dUTP concentrations which were expected to yield products containing from 20 to 0 fluorochromes per molecule showed fluorescence intensity diminution, as fluorochrome content decreased (FIG. 18). The distribution of incorporated fluorochrome labelled nucleotides in a given sample of DNA followed a Binomial distribution, assuming random incorporation. PCR products containing as little as one fluorochrome were imaged.

8.2.2. Imaging Nick Translation on Surface Mounted Molecules

Nick translation experiments on surface mounted lambda bacteriophage DNA were performed using standard biochemistries and F-dUTP (see Section 8.1). The critical amount of DNase I was determined by the bulk nick translation experiments (see Section 8.1).

To determine the optimum concentration of labeled nucleotides for studying the progress of nick translation on the surface, different ratios of dTTP/F-dUTP concentrations (5/1 to 50/1) were evaluated in overnight reactions. Samples were then imaged without staining. All samples had sufficient signal for imaging. dTTP/F-dUTP=5/1 was used for all the progression studies, since the yields were high and the measured fluorescence intensities were adequate to follow the early stages of incorporation, when few fluorochromes were present.

A series of identical nick translation reactions using lambda DNA (FIG. 19) was used to image the progress of labeled nucleotide addition (0.5, 1, 2, 4, 8, 20.5, 24 hours; see Section 8.1). Since no counterstain was added during these experiments, the only detectable signals emanated from the incorporation of labeled nucleotide.

The controls were tested for true incorporation of labeled nucleotide by withholding DNase 1, precluding any significant nicks, and counterstaining at the earliest time point. These controls show no incorporation without nicking activity, indicating template-directed addition, and eliminating the possibility of non-specific adsorption to the surface. The counterstaining results showed largely intact DNA populations. Together these data prove the presence of biochemically competent molecules. The DNA polymerase I from Boehringer Mannheim was shown to have no detectable nicking activity and was used for these studies.

To quantitate the rates of incorporation, fluorescence intensity measurements of molecules were made at each time point (see above) by averaging values from approximately 75 molecules (see Section 8.1). The plot of these results is shown in FIG. 20. Time points taken at 0.5 and 1 hour were not plotted since there were insufficient additions. These results show that incorporation of F-dUTP within the first few hours was proportional to time. After fitting the first few points to a straight line, we estimated that the average incorporation rate of F-dUTP into the fixed template DNA, within the first few hours, was approximately $3.7 \times 10^2$ dUTP/hr (or 7.5 dUTP/hr/kb of template DNA).

8.2.3. Imaging Nick Translation on Fluid-Fixed DNA Samples

As described in Section 8.1 above, lambda bacteriophage molecules were elongated and fixed onto derivatized surfaces by depositing small droplets of DNA solution (~0.2 to 0.5 $\mu$l of 0.01 ng/$\mu$l), using a glass capillary. After drying, these spots deposited elongated, fixed DNA molecules. FIG. 11 shows an image derived from a portion of a spot, after nick translation on the surface. The molecules here have accumulated on the periphery and showed extensive fluorochrome incorporation. Qualitatively, the rates and amounts of fluorochrome incorporation was similar to that obtained with other mounting techniques used in this study.

9. IMAGING, BLEACHING AND QUANTITATING SINGLE FLUORESCENTLY LABELED NUCLEOTIDES

The following example describes experiments demonstrating the detection of single dye molecules and the ability to distinguish whether objects contain one, two or three dyes based on counting discrete bleaching events over a series of one second exposures and on the fluorescence intensity of the objects.

9.1. Materials and Methods

Optical detection was accomplished with a Zeiss Axiovert 135-TV microscope with a Zeiss X100 Neofluar N.A. 1.3 objective, a Ludl MAC 2000 X-Y table stage, and a 488-nm line of an Ar+ laser (Innova 70-4, Coherent) was used for illumination. The beam was focused on a rotating ground glass wheel; the resulting scattered light was collected, and about 50 mW was delivered through a shutter (Vincent Associates) to the microscope. Interference effects were largely eliminated when the wheel was in place. The filter set was XF22 (Omega: 485DF22 excitation, 505DRLPO2 dichroic, 530DF30 emission). A Photometrics PXL cooled CCD with Kodak KAF-1400 CCD chip, A/D gain 12.6 electrons per count, 12.9 electrons noise readout noise, 0.65% linearity, full well capacity 46.5 k electrons was used to collect images. The microscope shutter was attached to the camera control unit so that the sample is illuminated only during manual focusing or while the CCD camera is collecting images.

A PCR reaction was carried out in the presence of R110-dUTP (Perkin-Elmer) using 25 bp primers which amplify the 500 bp sequence between bases 7131 to 7630 of bacteriophage lambda (Acc. No. J02459). The forward product has 97 potentially labeled T's while the reverse product has 108 potentially labeled T's for a total of 205 potentially labeled sites. The ratio of R110-dUTP to unlabeled dTTP was 1:205. The expected distribution of labeled bases is governed by the binomial distribution with parameters n=205, p=1/205. A predicted 37% of the products should be unlabeled. Among the labeled products, 58% should have one label, 29% two, 10% three, and 3% more than three labels.

The PCR products were mounted on a positively charged glass surface (APTES modified coverglass) with 20% β-mercaptoethanol in Tris-EDTA buffer and imaged using laser illumination at 488-nm, which was very roughly 500 W $cm^2$ assuming $10–4$ $cm^2$ illuminated and 50 mW total power. The relative illumination was measured by taking multiple images of an FITC treated APTES surface and of a thin sample of uranyl glass.

Focusing was done by hand. The shutter was closed, and the automatic X-Y table was commanded to shift one field before the image was taken. A series of 10 images were collected with one second exposure at a number of locations on the slide. There was an interval of about 8 seconds between each exposure during which the sample was in the dark.

Images were examined using NIH Image, IPLab (Signal Analytics) or locally written Unix X software. Nonlinear least square fits were done using MATHEMATICA™ (Wolfram Research). Images were also analyzed using cross correlation to the expected Gaussian profile and by Gaussian smoothing followed by peak finding. These techniques yielded the expected results, finding the objects which match the Gaussian profile of a point source of light. As expected, the background areas were only a few counts above the bias value, and isolated spots were easily visible.

Flat field correction using the measured relative illumination gave inconsistent results. A much more satisfactory result was achieved by subtracting a background image prepared from the last image of the bleaching time series, on which nearly all of the fluorescent objects had bleached. The few remaining objects were removed by taking a spatial minimum filter, and the image was smoothed and subtracted from the others. This background could be due to scattered light, filter leakage, or stray fluorescence.

Autofocusing techniques can also be used. One method is to use a very flat surface to hold the sample so that the position of the surface can be determined along the edges and the proper focus can be calculated. The background light levels are reduced by adding a second emission filter, by eliminating dust from the sample by drying cleaned surfaces in a dust-free environment, by using better quality immersion oil, and by tracking down sources of stray fluorescence.

The background noise level are reduced by trying alternate CCD camera gain settings. In these low light conditions, the higher gain setting results in lower noise. Also, background noise is reduced by careful image processing. The CCD dark image is measured many times, and the average value is subtracted from each image to remove the CCD pixel specific pattern without introducing additional noise. The background light is measured for a number of exposures and averaged so that subtracting the background will not add noise. Reduction of the amount of background light is also available.

9.2. Results

The observed signal to noise (S/N) for a single dye was bout 6. The background per pixel b is the average of the dark area around the light source, and the noise per pixel $\sigma_p$ is the standard deviation of the p values of the background area. If n is the number of pixels in the light source, then the signal S is simply the sum of all the raw pixels minus background, or $$S = \sum_{i=1}^{n} (p_i - b).$$

The noise $N=\sigma_b$ is simply the standard deviation of the background intensity of areas of n pixels, $$N=\sigma_b=n\sigma_p/\sqrt{n}=\sigma_p\sqrt{n}.$$

S/N for a pair of dyes was about 12, and S/N for three dyes was about 18. The noise per pixel, $\sigma_b$, was about 2.2 counts per pixel.

Nonlinear least squares fitting of typical objects on the image to a two dimensional Gaussian distribution yielded a sub-pixel estimate for the coordinates of the light source (x,y), an estimate of the background b, and the width w and height h of the distribution. The model was Gauss(x,y;w)*h+b. The best fit generally gave the same value for h as S, the sum of the pixels minus background. The background b generally matched the average of the surrounding background pixels. The residuals of this fit and the width of the Gaussian serve as diagnostics which can be used to automatically reject objects which do not match the usual profile of single dye fluorescence.

Objects are selected automatically using Gaussian smoothing followed by peak finding, or by cross correlation against the expected Gaussian shape. This second operation is implemented efficiently using a Gaussian smooth followed by subtracting one half the sum of surrounding pixels. Peaks found in this manner can then be fit to the Gaussian to determine a precise location and width, and accepted or rejected on the basis of their shape and goodness of fit.

Examining a single bright source on a series of one second exposures showed a decay curve with three discrete leaching steps. Examining a single dim source showed a single bleaching step, and intermediate intensity sources showed two bleaching steps. The number of objects with intensities comparable to those associated with one, two, and three step bleaching curves was consistent with the expected binomial distribution of dyes per PCR product. Most of the three dye light sources bleached to completion in 10 seconds.

10. PRIMER EXTENSION USING TAQ POLYMERASE ON OPTICAL MAPPING SURFACES

The following example describes experiments which demonstrate that Taq polymerase catalyzed primer extension reactions at elevated temperatures with labeled nucleotides on elongated molecules mounted on an Optical Mapping surface and the process is called Optical Primer Extension ("OPE"). This example also demonstrates that the Klenow fragment of DNA Polymerase I is capable of catalyzing primer extension reactions of surface-mounted DNA molecules.

10.1. Materials and Methods

DNA samples were fixed on a trimethyl silane modified glass surfaces, as described in Section 9.1 and then coated with polyacrylamide gel to confer stability. Samples were denatured in 7M urea, 40% formamide, and 50 mM at 80° C. for 10–15 minutes. Washes were performed after incubation. The surface was sealed with 50 µl of OPE reaction solution (1×PCR buffer II (Perkin-Elmer) 3 mM MgCl$_2$, 0.1 mM dNTP, 1×purified BSA (New England Biolabs, Beverly, Mass.) plus 0.6 nM primer probe, 10 uM F-dUTP (PE), and 2.5 units of Taq DNA polymerase (Perkin Elmer) using a Perkin Elmer PE1000 In Situ PCR Slide-sealing apparatus (PE1000). The sealed surface was then incubated in the PE1000 for 3 to 4 hours. Washes followed.

The sample was mounted with 20 µl of counterstaining solution (45% β-mercaptoethanol in deionized water with 1 mM YOYO-3 when R110-dUTP was used and 20–30% β-mercaptoethanol with 1 mM YOYO-1 when R6G-dUTP was used); stained for 2 to 5 minutes, and imaged by taking a pair of images from the same field using two wavelengths (DNA counterstaining, and the fluorochrome labeled nucleotide). The following filter packs ere used: either a combination of XF47 (for YOYO-3) and XF22 (for R110-dU) or XF22 (for YOYO-1) and XF37 (for R6G-dUTP) (Omega Optics).

This experiment was similar in concept to primed in situ synthesis ("PRINS") (Koch et al., 1989, Chromosoma 98:259–265), except that the primer sequences were shorter and the targets were surface-mounted DNA molecules in place of essentially intact chromosomes. The loci of these primer extension sites were mapped using manual methods (Meng, et al., 1995, Nature Genet 9:432–438) and using an adapted version of Optical Map Maker ("OMM") (see Sections 6.1 and 19; and Anantharaman et al., 1997, J. Comp. Biol. 4:91–118) to automatically map such sites from collected images.

Other labeled nucleotide experiments were performed to evaluate the effectiveness of Klenow fragment using single-stranded templates, mounted on Optical Mapping surfaces with random nucleotide hexamers as primers.

10.2. Results

The experiments with Taq polymerase demonstrate that minimal sized probes anneal with good specificity to unique sequences on surface mounted cosmid DNA molecules and support primer extension with labeled nucleotides to yield bright, fluorescent targets, facilitating their mapping. Comparison with known data showed mapping accuracies of better than 5%.

The experiments using the Klenow fragment of DNA Polymerase I and single stranded templates with random hexamer primers demonstrated vigorous extension, evidenced by robust signals, and that polyacrylamide overlays were not necessary, although they also proved effective.

11. NICK TRANSLATION ON OPTICAL MAPPING SURFACES

The following example describes experiments for the imaging of individual surface-mounted DNA molecules after nick translation with labeled fluorochromes.

11.1. Materials and Methods

A series of biochemical cycles and intermittent washes are performed to obtain partial sequence information from a single DNA molecule (FIG. 1).

First, double-stranded molecules are elongated and adsorbed to an Optical Mapping surface. DNase I (New England Biolabs, Beverly, Mass.) is then added to nick target DNA. The mean number of nicks is varied by simple titration of DNase concentration or by varying incubation times. The distribution of nick sites is adjusted to space them approximately 5 times the resolution of light microscopy, or approximately 1 to 2 microns (3 to 6 kb of B-DNA, assuming nearly complete elongation; 70–90% of the calculated polymer contour length). DNase treatment is followed by a wash to terminate activity. If nuclease activity is present after simple washing, proteinase K/detergent treatment or heat is used for inactivation, followed by additional washes. DNase does show sequence specificity (Clark et al., 1991, Biochemistry 13:5098–5102; and Laskowiski, 1971, "Deoxyribonuclease I", in *The Enzymes* Vol. 4, Boyer (ed.), Academic Press, N.Y. pp. 289–311), so that a truly random distribution of nick sites may be difficult to obtain; however, this should not pose a major problem.

Second, T7 exonuclease gene 6 (Sadowski, 1971, J. Biol. Chem. 246:209–216; available from Amersham) is used to open the nicked sites to produce gaps. This step is necessary only when T7 Sequenase v. 2.0 follows, since this polymerase boasts genetically ablated 3'-5' exonuclease activity, but no strand displacement or 5'-3' exonuclease activities. These gaps are also be filled in by Klenow (exo–) polymerase.

The amount of gapping by T7 exonuclease gene 6 must be carefully controlled to prevent an unacceptably high level of double-strand breaks. The optimal amount of exonuclease activity is determined by careful titration of nicking activity, followed by formation of small to medium gaps of approximately 20–50 bp, as indicated in the series of experiments assessing time and concentration dependence (see Section 5.4). Fortunately, only small gaps (20–50 bp) are necessary. Given the multiplicity of sites, it is preferable to err on having a proportion of the nick sites insufficiently gapped, rather than producing significant numbers of double-stranded breaks.

DNA polymerase I (New England Biolabs) and fluorochrome labeled nucleotide, i.e. $A_f$, are added in standard buffers. The 3'-end of nick sites are labeled only if the template strand contains a complementary base or bases. This action ceases when the base in the template strand is not complementary. Multiple bases of the same type can be added, as directed by the template strand (see FIG. 1). Both Klenow (exo-) and T7 Sequenase v. 2.0 can be used to fill in gaps, whereas only Klenow should perform strand displacement at a nick site (Walker et al., 1992, Nucleic Acids Res. 20:1691–1696). After the reaction has finished, fluorescence additions are imaged.

11.2. Results

The results of the nick translation experiments reveal that DNA Polymerase I is biochemically active in an Optical Mapping-type chemical environment and that single fluorescently labeled nucleotides can be imaged.

12. OPTICAL SEQUENCING SYSTEM

This example describes a system for optical sequencing by nick translation.

12.1. Materials and Methods

The Optical Sequencing system is composed of the chemistries described above (in Section 11) and an imaging/analysis subsystem which tracks the additions of fluorochrome labeled nucleotides (at each reaction step), quantitates the number, and employs a series of filters to discriminate true signal from noise. In addition, the analysis of the filtered data for final sequence determination will rely on a Bayesian inference approach similar to what we have already developed for Optical Mapping. In other words, prior information will be used to formulate the most probable hypothesis, as tested for consistency against the data set.

12.1.1. Detection of Single Fluorochromes

An important requirement for successful Optical Sequencing will be the reliable detection of single fluorochromes as added by DNA polymerases to nicked or gapped section in large molecules. As described in Section 10, single fluorochromes incorporated into PCR products were imaged and quantitated using a cooled CCD camera and a standard epifluorescence microscope, using laser illumination. For Optical Sequencing, the same essential optical arrangement is used.

12.1.2. Noise

Sources of noise include intrinsic sample fluorescence, scattering in samples and optical train, dust, imperfect optical filters, fluorescent immersion oil, fluorescent optical components, and detector noise. Dust contamination can be a major problem. Samples are prepared in a High Efficiency Particulate Arrestor ("HEPA") (Forma) filtered hood and, if necessary, the microscope is enclosed within a plastic shell fed with HEPA filtered air. Our present single fluorochrome system (see Section 9.1) uses a standard fluorescence microscope coupled to an argon-ion laser. If system, rather than sample, noise becomes a limiting factor in sensitivity (S/N) due to scatter within the optical train, then an internal reflectance illumination system can be constructed as similar to that described by Funatsu et al. (1995, Nature 374:555–559) Noise is also to be reduced by straightforward elimination of obvious sources by complementary statistical approaches as described below.

12.1.3. Correlation of Signals with Molecular Backbones

Signals correlated with DNA molecules mounted on the surface are analyzed, but other signals are considered spurious. Furthermore, loci of nucleotide additions are assessed for spurious additions that may be due to polymerase activity at closely spaced sites (comparable to the Rayleigh limit), or addition of long strings of the same nucleotide.

Fluorescence intensity measurements, with emphasis on their spatial distribution, are used as part of this filtering process. For example, single, or small numbers of, fluorochromes co-localized are fitted by a two-dimensional Gaussian intensity function, with limited residues (Gelles et al. 1988, Nature 331:450–453; in this work DIC was used (Schmidt et al., 1996, Proc. Natl. Acad. Sci. USA 93:2926–2929)). Measurement of the point-transfer function of the optics facilitates (using small fluorescent latex beads) this process. In fact, using such analysis, Schmidt et al. obtained a fluorochrome positional accuracy of 30 nm (Schmidt et al., 1996, Proc. Natl. Acad. Sci. USA 93:2926–2929). Gelles et al. positioned kinesion coated beads with a precision of 1 to 2 nm (Gelles et al., 1988, Nature 331:450–453).

Similar operations have been accomplished using our present system (see Section 8.1) and found that such measurements provide accurate fluorochrome position (x, y), and accurate quantitation of fluorescence intensity.

The framework of the analysis is centered on the accumulation of fluorescence intensities at addition sites, or "spot" histories, as a function of position, (x, y), and addition cycle, I(s). This scheme is outlined in FIG. 5. Positional data of fluorescence intensities accumulated after each cycle are used to link labeled nucleotide additions for a given nick, or gap site. In the microscope field of view, there are many molecules, each containing 10–20 nick sites, varying in the size of the target molecule and the frequency of nick sites. The filtering step discriminates addition sites on the basis of fluorescence intensity—insufficient or excessive fluorescence intensities are rejected.

The criteria for this selection is based on the accurate quantitation of fluorochrome addition number. Depending on the set criteria, additions are given "scores" to measure how much they deviate, and the additions with low "scores" may be ultimately rejected in a Bayesian inference scheme. For example, if the addition history of a given nick site is well-behaved during the four cycles and then fails due to, for instance, template damage, this site achieves a low score only for that incomplete or spurious addition.

Another failure mode is excessive nucleotide addition, perhaps caused by opening of a cryptic nick site after nuclease treatment. The key point is that failure modes can be rapidly characterized and catalogued. Confidence estimates and sophisticated error checking are then applied to the raw sequence data, based on this type of information. Such analysis for operator-free scoring of endonuclease cleavage sites has been accomplished in Optical Mapping, and adaptation to Optical Sequencing is straightforward.

After the completion of sequencing cycles, filtering and correlations are done with molecule backbones or restriction fragments, $C_b$. This value describes the confidence of assigning a given addition site to a DNA molecule or restriction fragment. Such assignment serves two purposes: 1) to further eliminate noise—only additions associated with target molecules are considered, and 2) to bin sequence "reads", according to position, for verification and possibly finished sequence assembly. This operation requires simple modification of analytical approaches we originally developed for Optical Mapping and Optical Primer Extension (see Section 6). For example, the algorithms already developed accurately map cleavage sites (operator-free) along a clone molecule, even in the presence of noise generated by incorrect assignment of cut sites, or by extraneous endonuclease activity.

The automated analysis routines we have established for Optical Primer Extension are used as follows: images of molecular backbones (as revealed by counterstaining with YOYO-1 (Molecular Probes)) are overlaid and thus correlated with results from labeled primer extensions. Raw data consist of the position of primer extension sites along a large number of molecules. Newly developed algorithms accomplish this task automatically to map labeled primer extension sites (Anantharaman et al., 1997, J. Comp. Biol. 4:91–118). Although there is some image registration offset present, this has not posed any major problems in the analysis.

12.1.4. Counting Fluorochrome Additions

Counting the number of nucleotide additions is a critical part of Optical Sequencing. One or more complementary strategies are used including fluorescence intensity measurement and/or photobleaching if it is determined that intensity measurements alone do not suffice.

12.1.5. Fluorescence Intensity Measurements

Confident quantitation of small numbers of nucleotide additions are performed using the approaches developed for the measurement of fluorescence intensities. Reliable flat field corrections are used to compensate uneven illumination. This is necessary to ensure that each pixel is radiometrically correct.

To accomplish this, a more precise way of correcting for nonuniform illumination is developed so that the fluorescence measured at the edges of the image can be compared to fluorescence measured at the center. Micron thick samples of uranyl glass are used as a reliable and reproducible way of obtaining an initial estimate of the illumination. To refine this coarse estimate, a series of images of isolated single dyes are taken. Since the dyes bleach in a single step, all dyes which appear in a second image were fluorescent for the entire exposure of the first image, even if they bleached part way through the exposure of the second. In this way, the illumination can be determined at different places in the field of view.

These values can be interpolated to determine the illumination over the entire field of view. Further improvements are achieved by iterative optimization calculations using a time series of images of isolated groups of three dyes. By following the bleaching events, three point calibration curves are determined over the field of view. This method has the advantage of determining the background (Y-intercept) as well as the excitation intensity (slope).

With shading correction accomplished, counting co-localized fluorochromes is relatively straightforward.

Schmidt et al., using approaches similar to ours, claim the potential for stoichiometric resolution of up to 8 fluorochromes (Schmidt et al., 1996, Proc. Natl. Acad. Sci. USA 93:2926–2929). This is based on their measurements of a relatively noisy system—cell membranes. Their argument is as follows: by knowing the fluorescence intensity of a single fluorochrome, $\bar{i}_1$ and if the error, $\sqrt{n}\sigma_1$; (where n is the number of fluorochromes and $\sigma_1$ is the measurement error), is smaller, then n can be determined. In our system, as more fluorochromes are added, fluorochrome-fluorochrome interaction, through quenching, may skew measured intensities, and thus, $\bar{i}_1$ may vary with addition.

12.1.6. Photobleaching Measurements

As discussed above, measuring time courses of photobleaching is useful for counting fluorochromes within a given small area or spot. As described in Section 7 and Anantharaman et al., 1997, J. Comp. Biol.4:91–118, we have developed automatic software routines that use algorithms that identify fluorochromes within an image and derive photobleaching curves for each spot. These curves are analyzed in terms of breadth, relative to background, and also values are fit for multiple fluorochrome events modeled as a stochastic process. Typically, under experimental conditions we have used (fluorochrome labeled PCR products; see Section 10), photobleaching lifetimes of 1–85 seconds were measured.

Illumination and chemical environmental conditions result in considerably varied lifetimes (Huston et al., 1991, Chemical Physics 149:401–407 and Rosenthal, 1978, Optics Comm. 24:164–166). The best anti-photobleaching reagent we have found is 30% β-mercaptoethanol, a free-radical scavenger, in standard Tris-based buffers (Yanagida et al., 1986, in *Applications of Fluorescence in the Biomedical Sciences*, Taylor et al. (eds) Alan R. Liss Inc., New York, pp. 321). In the presence of β-mercaptoethanol, fluorochrome photobleaching lifetimes are extended as much as 500 fold.

12.1.7. Evaluating Photobleaching and Fluorescence Intensity

Given the nature of random sequence acquisition in Optical Sequencing, fluorochrome counting approaches (both fluorescence intensity and photobleaching), are tested using a previously sequenced substrate (i.e., lambda bacteriophage or cosmid DNA).

To confidently test our fluorochrome counting approaches, fluorochrome labeled PCR products are generated using a mixture of labeled and unlabeled dUTP or dCTP. Emphasis is given to assessing the effects of multiple fluorochromes on the measured fluorescence intensity. By knowing the relative ratio of fluorochrome labeled/unlabeled nucleotide, the distribution (binomial) of fluorochromes/molecule for a population of 1,000 to 10,000 molecules (using 1–10 images) is calculated, and thus compared with our measurements.

Another test system includes primer extensions to known templates (using only fluorochrome labeled nucleotide) (see Section 14). One feature of such products is that the number and spacing of labeled nucleotides is easily varied to study their effects on fluorescent yields in terms of interactions. Further, synthetic oligonucleotides can be used, with fluorochromes strategically incorporated as phosphoramidite conjugates, offers ease of design, given the limits of conjugated phosphoramidite oligonucleotide synthesis. A drawback to using labeled oligonucleotides is that the conjugated fluorochromes may not be chemically analogous to the labeled dNTPs used for polymerase-based additions.

12.2. A Simple Instrument for Optical Sequencing

The system consists of a microscope mounted, sealed chamber connected to a syringe pump with an in-line reagent injection port. The nucleotides, polymerase and other reagents are loaded into the sample loop through the injection port. Reagents will be stored and injected from separate syringes. The syringe pump can deliver reagents injected into the loop, to the chamber, or deliver buffers for washing between reaction steps. See FIG. 20 which diagrams the components for a simple unautomated Optical Sequencing System.

The sample to be sequenced is first mounted onto an Optical Mapping surface by the methods described in Section 9. Next, the surface is placed in the "sealed chamber", constructed of Teflon and having gasketed metal flanges to firmly secure the surface during fluid injection. Temperature control is accomplished by jacketing the apparatus with feeds from an external waterbath. Previously designed similar chambers have been used for fluid flows to elongate DNA molecules for Optical Mapping (see U.S. Pat. No. 5,720,928 incorporated herein by reference). To prevent motion of the surface during reagent loadings, which may destroy image registration, minimal pressures is employed during deliveries and washes.

Automation of the system can be accomplished by incorporating solenoid driven valving devices and the like.

12.3. Analysis of Optical Sequencing Cycles

This section calculates the number of cycles needed to read a sequence given a sequence of length N is calculated as follows. Each cycle adds one of the bases A, C, T and G with label and then bleaches the label. The sequence of cycles is assumed to be a repetition of the following kind: A,C,T,G,A,C,T,G, . . . In each cycle the given sequence is extended, if there is a match. For example, if a labeled A is used in the current cycle, then A is added if there is one or more A's at the current site. If there is no A, then the cycle has no effect. For simplicity, assume that the process is error-free and that it is possible to tell exactly how many A's match at this cycle.

A simple way to analyze this is to associate a state with any particular location (the state is labeled A, C, T or G, if the immediately preceding base is A, C, T or G, respectively) and count how many cycles have been used so far. Thus if the cycle is in state A and the next base is A, then the state transition is to the same state (A), with an increment of 0 to the cycle length. Similarly, if the next base is C, then the state transition is to C, with the increment to the cycle length being 1, etc. This structure is represented in the following state transition table, with the entries representing the cycle length increment values:

|   | A | C | T | G |
|---|---|---|---|---|
| A | 0 | 1 | 2 | 3 |
| C | 3 | 0 | 1 | 2 |
| T | 2 | 3 | 0 | 1 |
| G | 1 | 2 | 3 | 0 |

Thus the increment in the cycle length for the in the base in the sequence can be described in terms of a random variable $X_i$, where $$\mu(X_i)=(0+1+2+3)/4=3/2,$$

is its expected value, and $$\sigma_2(X_i)=(0+1^2+2^2+3^2)/4-(3/2)^2=5/4$$

is its variance.

Thus the total number of cycles needed for a sequence of length N is given as $$S_N = X_1 + X_2 + \ldots + X_N,$$

and has a normal distribution (by Central Limit Theorem)

$$S_N \sim N(3/2N, \sqrt{5N}/2).$$

Thus for N=20, the expected number of cycles is 30 with a standard deviation 5. Thus with only $$30 + 3 \times 5 = 45 \text{ cycles},$$

it is possible to obtain sequences of length 20 or more with probability 0.999. By the same argument, with only 35 cycles, it is possible to determine sequences of length 20 or higher with 0.841. With these numbers, it seems plausible that the proposed method will work well to give large number of sequences of 20 reads with relatively few cycles.

12.4. Strategies for Sequencing

The final or intermediate strategies for Optical Sequencing depend on the length and the type of sequences or "reads" obtained. Types refer to sequences consisting of consecutively known bases, or strings punctuated by undetermined bases. Essentially, low-resolution sequencing may appear much like high resolution mapping. For example, if strings of 4 bases could be accurately mapped over BAC or cosmid clones at a density comparable to cleavage sites defined by 4–8 base cutting restriction enzymes, then such information would yield a high resolution fingerprint, more so if these 4-base strings are randomly accumulated over an ensemble of identical clone molecules.

Another strategy is to search for sequences by non-random addition of nucleotides, for example by using ordered base additions that correspond to known regulatory protein binding sites or sequence repeats of interest.

12.5. Throughput

In Optical Sequencing a cosmid, the Optical Mapping techniques can place approximately 100 molecules into a typical field of view, as imaged by our cooled CCD cameras. Placing about 20 nick/gap sites on each molecule, on the average, creates 2,000 potential sites for sequence acquisition. If 10 consecutive bases are read, then 20 kb of raw sequence is obtained. If a cycle takes 15 seconds to complete, then the potential throughput here is (25 cycles)× (15 seconds)=approximately 6 minutes, or about 3 kb/minute, or 180 kb/hr. These values are potentially beyond the range of sequence obtained using a ABI 377 DNA sequencer.

12.6. Schemes for Directed Addition

If fluorochrome-labeled dNTPs prove to be refractory to any significant consecutive addition to the templates, then the addition cycles are alternated with unlabeled dNTPs to optimally space them to ameliorate steric hindrance and thus promote addition. Labeled addition spacing is evaluated using the sequencing assays described in Section 13, for example, by adding 1 to 5 unlabeled dNTPs as spacers (in place of fluorochrome labeled dNTPs in the cycles).

If two consecutively labeled nucleotide additions prove difficult, labeled dNTPs are mixed with unlabeled to facilitate additions. What is generated instead is an informative fingerprint or, more precisely, a series of accurately mapped landmarks.

Finally, using a combination of labeled dideoxyribonucleotides, phosphorothionate-nucleotides (resistant to 3'-5' exonuclease activity), and polymerases with competent 3'-5' exonuclease activity, we may be able to reliably add and remove labels one at a time—obviating fluorochrome crowding problems and the measurement of fluorochrome number.

13. EXAMPLE:

Assays for Optical Sequencing by Primer Extension

This example describes assays for determining the efficiency of optical sequencing of single molecules performed using primer extension.

13.1. Materials and Methods

Assays of primer extension reaction products utilize both optical techniques and traditional, electrophoretic techniques. The assays for incorporation allow the determination of rates of incorporation as affected by temperature, surface conditions, buffer composition, and template composition. Fluorochrome labeled nucleotides compatible with the ABI 377 DNA Sequencer (Perkin-Elmer Applied Biosystems, [F]dNTP Reagents, Protocol 402774, 1996), are used to analyze products of primer extension reactions. Using known templates and nucleotides in the primer extension reactions, the size of the primer extension product issued to evaluate the extent of the addition. This analysis might be complicated by anomalous electrophoretic mobilities induced by the incorporated labeled nucleotides. Sequencing sizing ladders made with a series of systematically varied fluorochrome labeled nucleotides are used to calibrate the apparent lengths of known extension products.

The surface-based assays consist of two different operations. Both will be assayed on an Optical Mapping/Sequencing surface. However, one will use primer extension products generated in a tube, and the other will use templates pre-annealed with primers in a tube and then mounted on a surface for extension in situ. The analysis of these products uses techniques previously developed for Optical Primer Extension and single fluorochrome detection. Section 14 further discusses details and experiments designed to determine resolution of molecules with small numbers of fluorochromes. The two types of experiments (optical and electrophoretic) will allow for extensive data cross-checking.

13.1.1. Templates and Primers

The addition efficiency of Sequenase, or Klenow, with the fluorochrome labeled nucleotides, is determined using primer extension reactions with known templates and will vary the ratio of fluorochrome labeled nucleotide from 0 to 100% of the mix (4 dNTPs, containing one fluorochrome labeled nucleotide). The incorporation efficiency of single, pure labeled nucleotide (no other nucleotides added) is also measured. Optimization of addition is obtained by moving from diluted, labeled nucleotide to undiluted. These templates consist of 20 to 60 NT oligonucleotides, designed to mostly contain the same random sequence but with inserted blocks of 10 to 30 nucleotides that differ. These will allow testing of primer extension capabilities under simulated Optical Sequencing conditions. Complementary 18 to 20 nucleotide primers are used, and their 3' ends can also varied to evaluate effects on primer extension. The present invention also can produce longer primer extensions consisting of hundreds of bases.

13.2. Results

The assays described above provide rates of incorporation of labeled nucleotides under different conditions for optimization of the reactions.

14. OPTICAL APPROACHES TO SINGLE NUCLEOTIDE POLYMORPHISM (SNP) DETECTION

This example describes experiments for identifying single nucleotide polymorphisms by optically imaging individual nucleic acid molecules.

14.1. Materials and Methods

The biochemical steps involved in the proposed scheme for Optical SNP Detection are as follows:

Step 1: Annealing of probes to surface-mounted molecules. Using the techniques developed for Optical Primer Extension (see Section 10), probes are annealed to surface-mounted molecules using high temperature PCR-like conditions. Molecules are produced from conventional and/or long-range PCR. Conditions are carefully controlled, taking into account probe composition and overall stringency to control probe hybridization. Machine vision and Bayesian statistical techniques are used to automatically identify the most probable probe locations consistent with the data.

Step 2: Dideoxy addition. Taq polymerase and a chosen base of dideoxy nucleotides are added and single base extension occurs. This sets the stage for the next step—primer extension with some fluorochrome labeled nucleotides.

SNP detection can take several forms depending upon prior knowledge of the mutation, and the desire for a positive or confirmatory negative tests. For example, if the mutation involves an A-to-G transition (on the template strand), then a dideoxy nucleotide could be selected for (1) non-addition to a mutant template but addition to the wild type template or (2) exclusion of the three other bases. Heterozygosity will be determined from the proportion of subsequently labeled loci obtained in Step 3.

Step 3: Taq polymerase is added along with a pool of dNTPs containing a portion of fluorochrome labeled nucleotide to determine if primer extension occurs. Primer extension occurs only if the dideoxy nucleotide does not add—addition occurs only when selected dideoxy nucleotide and template are mismatched. The fluorochrome labeled dNTPs will be the same Perkin Elmer nucleotides described for Optical Sequencing (see Section 5.5).

There are two major factors governing the desired amount of primer extension: (1) enough labeled nucleotide addition must occur for reliable detection, and (2) multiple primers must be spaced far enough to allow for dependable spatial resolution. Under light microscopy, the practical resolution is determined to be approximately 1–2 microns, or about 3 to 6 kb, or using the CCD imaging system—15 to 30 pixels. Error analysis for the Bayesian modeling of the system is based on the assumptions of missed hybridization sites, hybridization to incorrect sites, failure of dideoxys nucleotides to correctly add, and faulty primer extension reactions—both positive and negative. Proper evaluation and modeling of experimental events will determine the number of molecules required for final SNP calling.

14.1.1. System Description

Samples to be analyzed from SNP detections consist of short or long-range PCR products, and are analyzed as follows. Samples in microtiter plates, 81–100 in number, are gridded by the laboratory spotting engine (see Section 7) onto four Optical Mapping surfaces, in register. Fiduciary marks are applied to maintain orientation. Spotted surfaces are overlaid with acrylamide; each is treated with a different dideoxy and Taq polymerase and then washed to remove excess unincorporated material. A mixture of dNTPs, fluorochrome labeled nucleotides, and Taq polymerase is added, and primer extension occurs at sites lacking dideoxy nucleotides.

The surfaces are then mounted on an automatic imaging microscope coupled to the OMM network computer and control system (see Section 7). Machine vision algorithms described in Section 6 analyze images to select molecules and record sites of primer extension. Statistical techniques, described in Section 6, assess machine vision results to produce a "map" of primer extension sites, consistent with the data set.

14.1.2. Sample Preparation and Benchmarking

PCR reaction product samples are prepared using columns known to those skilled in the art. Fluorochrome labeled nucleotides are used as part of the PCR reaction mix. PCR products are differentially labeled and distinguishable from the template; unincorporated labeled nucleotides are easily washed from the surface, while target amplificant molecules will be retained. When long-range products are generated, the amount of fluorochrome labeled nucleotide is titrated to minimize premature termination of reactions and thus optimize yields, specificity and fidelity.

The BRCA1 region (Shattuck-Eidens et al., 1995, JAMA 273:535; Johannsson et al., 1996, Am. J. Hum. Genet. 58:441–450; and Gayther et al., 1996, Am. J. Hum. Genet. 58:451–456) can be used as a test system, since our laboratory has generated a series of long-range PCR primers across this region to make a 80 kb PCR contiguous sequence. Genomic templates are obtained from patient materials.

The sequences of primers for use in the BRCA1 PCR reactions are shown below (from the coding strand, written 5' to 3'; and mutations are capitalized):

1. cattaatgctatgcagaaaatcttAG (mutant 185 delAG, exon 2 codon 23, stop at codon 39) (SEQ ID NO:5);
2. ttctcaaccagaagaaagggccttcacagT (mutant T to G @ nucleotide 300, exon 5, cys-gly change at exon 61) (SEQ ID NO:6);
3. tacatcaggccttcatcctgaggattttatcaA (mutant del A @ nucleotide 1675, exon 11, codon 519, met-stop change) (SEQ ID NO:7);
4. ccagtgaacttaaagaatttgtcaatcctaG (mutant del G @ 2293, codon 725 exon 11, stop at codon 735) (SEQ ID NO:8);
5. tgttccaaagataatagaaatgacA (mutant del A @ 2595, exon 11 codon 826, stop at codon 845) (SEQ ID NO:9)

Samples are prepared in microtiter plates for automatic spotting using a spotting engine. Approximately 25 to 100 samples will be deposited onto each Optical Mapping surface and then overlaid with acrylamide.

14.1.3. Dideoxy Addition and Primer Extension

Using Optical Mapping conditions described in U.S. Pat. No. 5,720,928; Cai et al., 1995, Proc. Natl. Acad. Sci. USA 92:5164–5168; and Cai et al., 1998; and Cai et al., 1998, Proc. Natl. Acad. Sci. USA 95:3390–3395, which are all incorporated herein by reference), Taq polymerase is used to add four different dideoxy nucleotides (ddA, T, G, C) separately to the four identically prepared gridded surfaces; samples are incubated in a Perkin Elmer in situ PCR instrument. The use of four separate reactions increases the amount of effort but provides an important way to cross-check results. Variation of time, temperature, enzyme concentration, and dideoxy nucleotide concentration are tested to optimize the yield of addition, to minimize side reactions, and to attenuate any nuclease activity.

Primer extension reactions are performed on gridded surfaces with close attention paid to balancing the amount of extension with issues of optical detectability. The amount of fluorochrome labeled nucleotide required for detection should be minimized. A consideration is that prolonging time allocated for extension increases chances of non-specific additions and further degrades template strands—particularly at high temperatures required for thermophilic polymerases. Also, excessive additions will compromise resolution of closely spaced probes if extensions run into each other. One solution to this problem is to use Watson and Crick strands when probes are close, since additions will then run in opposite directions.

Initially, the test system is based on primer extensions to lambda DNA template, and later to long-range PCR products made using BRCA1 primers with genomic templates (see Section 14.1.3.2.). Taq polymerase is used for these extensions, since high temperatures increase stringency and readily maintain single strandedness.

14.1.3.1. Polymerase

Taq polymerase (Amersham) does not efficiently incorporate dideoxy nucleotides; deoxynucleotides are incorporated approximately 3,000-fold more effectively (Tabor et al., 1995, J. Biol. Chem. 264:6447–6458). Recently, Tabor and Richardson replaced a critical phenylalanine with tyrosine in Taq polymerase (Taq DNA polymerase F667Y), and found that dideoxynucleotide incorporation efficiencies were dramatically improved and were reduced to a mere two-fold difference (Tabor et al., 1995, Proc. Natl. Acad. Sci. USA 92:6339–6343). This polymerase is commercially available from Amersham.

14.1.3.2. Design of Primers

Primer design and hybridization criteria developed for Optical Primer Extension is used (see Section 10) as the initial experimental standard. This technique uses essentially the same primer design criteria as for long-range PCR. Conditions for extension will also follow Optical Primer Extension guidelines as described above in Section 13.

14.1.4. Analysis of Optical SNP Detection

N primers are added to a clone of length G, to determine the single base at one end of the primer. Let us assume that $p_c$ is the probability that the primer adds at the correct position and the correct location is labeled. Let $\sigma$ denote the resolution with which our optical process can identify the location.

Similarly, let us assume that $p_f$ denotes the probability that the primer adds to the "wrong location." Examining a small window of size w around a "correct site," we see that the true labels (e.g., A) will be distributed around the correct site as a normal distribution with standard deviation $\sigma$. Similarly, the false labels (C, T, or G) will be distributed as a Poisson distribution, with rate $$\lambda_f = p_f N/4G.$$

Thus examining the labels in that window, we see that the number of true labels is proportional to $p_c \Phi(w/2\sigma)$, and the number of false labels is proportional to $$\lambda_f W = p_f N w/4G.$$

Aiming for a signal to noise ratio of 50:1 (rather conservative), we see that $$p_c \Phi(w/2\sigma) < 50\ p_f N w/4G,$$

and $$N < \frac{G}{75} \frac{P_c}{\sigma p_f}.$$

Choosing $w=6\sigma$, and assuming $p_c$ 0.6, $p_f=0.1$, $\sigma \sim 1$ kb, we can use N=12 primers for BAC (G=150 Kb) and N=4 primers for cosmids (G=50 Kb). Combinations of probes are evaluated to assess interference and detectability.

The present invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

15. GENOME INDEXING

A further improvement to the methods described above has been termed genome indexing. Genome indexing allows whole genomic nucleic acid, in effect, an entire genome, to be used as a template. The method enables the fabrication of maps that correlate restriction sites to transcription events, on an individual nucleic acid molecule basis. Coupled with the sequenced genomes already known, the method enables a completely unknown DNA to be unambiguously identified as being from a particular chromosome and region of the given organism.

Conventional approaches to message profiling rely on microarrays and the DNA chips designed by Affymetrix. These arrays are used virtually exclusively to analyze material extracted from cells. The inherent limitation to these approaches, however, is that one can only assay what is designed into a given chip. If the chip is not designed to assay for a particular entity, a new chip must be purchased.

Moreover, the mechanisms under investigation are performed in vivo or post-extraction, but prior to exposure to the chip. In short, the biochemical operations that can be performed on the chip itself are limited to hybridization. Thus, nucleic acid samples incorporated into such chips are biochemically inaccessible and present a distinctly finite subset of targets for analysis. This is especially so with Affymetrix-brand oligonucleotide arrays.

The development of single molecule approaches to biochemical analysis has enabled a broad range of techniques to visualize molecular details of transcription. For example, Davenport et al., 2000, Science 287:2497–2500, used video-enhanced differential interference contrast light-microscopy to image the action of individual E. coli RNA polymerase (RNAP) molecules immobilized to a surface. Bustamante et al., 1999, Biphysical J. 77:2284–2294, used high-resolution atomic force microscopy (AFM) to image the E. coil RNA polymerase initiation complex. Fluid tapping-mode AFM has been used to observe transcription on a mica surface, Brown & Botstein, 1999, *Nature Genetics* 21:33–37.

Collectively, these studies reveal that individual RNA polymerase molecules exhibit different intrinsic transcription rates and different propensities to pause and stop. Although single molecule biochemical studies to date have revealed numerous insights into the mechanisms of transcription, these experiments remain difficult to perform, in large part, because meaningful data is only obtained after numerous trials have been performed and ultimately averaged. In the approaches mentioned in the preceding paragraph, time-averaging (that is, repetitive experimentation on a single molecular substrate) is being used in place of ensemble averaging.

In contrast, in the present invention, the inherent power of single molecules to become meaningful substrates for experimentation is realized by the massively parallel study of populations of individual molecules or complexes. In this fashion, the researcher can control how the ensembles are averaged. Moreover, sophisticated computational approaches can be used to analyze molecular populations rapidly and repeatably. The method disclosed and claimed herein brings the use of molecular populations to bear on the mechanistic study of nucleic acid reactions such as transcription, phosphorylation, glycosylation, extension, etc. Literally, any reaction in which nucleic acids play a role can be analyzed using the method. Further still, an entire genome can be studied and indexed in a single ensemble.

Moreover, the method is scalable, even to the point that entire genomes can be used as templates.

In the discussion and Examples that follow, the invention is described in the context of studying transcription reactions of DNA. This is for brevity and clarity only, and does not limit the invention in any fashion. The invention will function to analyze literally any enzymatic or chemical reaction in which nucleic acids play a role. Such reactions include, without limitation, hybridization, nucleic acid sequencing, extension, reverse-transcription, glycosylation, phosphorylation, complexation, etc.

The central theme of the subject method is an in vitro approach for the high-throughput assessment of transcriptional activity and mechanistic elucidations using ensembles of single molecule templates. The approach follows transcriptional activity by capturing labeled elongation complexes in vitro and analyzing signals from the labeled complexes. In the preferred embodiment, a fluorochrome is used as a label, and the captured, labeled complexes are imaged by fluorescence microscopy. Of course, other labeling techniques are known and included within the scope of this invention, such as using radiolabels, other types of chromophores, etc. Fluorescent labeling, however, is preferred.

Template positions and activity are determined as discussed supra in Section 5.

Thus, the inventive method can be used to determine promoter sites and strength on a genome-wide scale. The inventive method can also be used to discern and/or elucidate mechanisms of transcription on an ensemble of single DNA molecules, including initiation, elongation, pausing, and termination events. Additionally, the method can be used as a platform for the detailed screening of compounds targeting transcription. Thus, the method provides a high-throughput means to screen compounds for their effect on transcription.

The preferred method disclosed and claimed herein utilizes elements of optical mapping, as described above, to determine the loci, quantity, and character of transcriptional events. For example, the method can be used to determine the loci, quantity, and character of transcriptional elongation complexes generated in vitro using fluorochrome-labeled ribonucleotides. The Examples that follow demonstrate that the present invention is capable of imaging elongation complexes using fluorescence microscopy, and to correlate the position of those complexes relative to restriction sites within the same template. This has been shown using both clone and genomic templates.

In the general approach, a transcription reaction is initiated in vitro in a reaction vessel or using nucleic acid molecules already bound to an optical mapping surface. The transcription reaction is initiated and run in the presence of fluorochrome-labeled NTP's. The reaction results in the formation of elongation complexes on the DNA template, i.e., complexes where transcription has been initiated. In this illustrative example, the reaction is then stopped at the elongation state.

If the transcription reaction was performed in a separate vessel, the reaction products are then mounted onto a substrate for optical imaging and mapping, as described herein. (This step is omitted if the transcription reaction is initiated using nucleic acid already bound to the optical mapping surface—the product complexes are then already mounted to the optical mapping substrate.) The reaction products, now mounted to the substrate surface, can be visualized at this point, if desired. The bound products are then treated with a restriction enzyme and the cut regions are imaged. Using differential labeling and conventional fluorescent filter sets, labeled DNA can be distinguished from labeled RNA. Contig maps are then constructed using the optical mapping techniques described hereinabove.

The beauty and utility of this approach are self-evident. Because the DNA and RNA products can be imaged independently, a map of transcriptional events can be fabricated either independently of, or in conjunction with, a map of restriction sites, in the same experiment and using the same template. A template which can be the entire genomic content of a given organism or individual.

The experiments described in the Examples that follow use Bacteriophage T7 RNA as an illustrative RNA polymerase. Bacteriophage T7 RNA polymerase has been used extensively in in vitro transcription reactions in an effort to elucidate the biochemical aspects of how RNA messages are made and modulated. For a review, see Anantharaman & Mishra, 1998, *NYU Technical Report* 759. Bacteriophage RNA polymerases, i.e. T7, T3 and Sp6, have also been well characterized, and are commonly used to study transcription mechanisms, as well as to prepare labeled RNA in vitro. Likewise, studies of prokaryotic transcription systems commonly use *E. coli* RNA polymerase for in vitro transcription work related to basal transcription or gene regulation study. Transcription in *E. coli* employs a multi-subunit *E. coli* RNA polymerase, whose core enzyme is comprised of four subunits (a, a, b and b').

In contrast to the *E. coli* RNA polymerase, bacteriophage T7 RNA polymerase (T7 RNAP) is known as one of the simplest enzymes catalyzing RNA synthesis. The T7 RNAP enzyme consists of one subunit and is able to carry out transcription without the need for auxiliary factors. Kochetkov et al., 1998, *FEBS Letters* 440:264–267.

One utility of the subject method is to create genome indexes of transcription sites. In short, Optical Mapping can be used to create restriction maps for whole genomes using a collection of maps constructed from ensembles of large, individual DNA molecules. The program, Gentig, is used to assemble these data into a single consensus map, which covers an entire genome. Briefly, Gentig implements a computationally sophisticated Bayesian inference approach (as described above in Section 6.3.1) to score modeled experimental error against a user-provided data set to find overlapping map patterns between random genomic DNA molecules. Given a finished map of an entire genome, e.g., E. coli, the approach can also be used to align a single mapped molecule to the mapped genome. Additionally, if the genome in question has already been sequenced, then single molecules can be aligned to in silico maps constructed from this sequence; if the sequenced genome has also been annotated, then gene identities and functionalities can be assigned to maps locations on such molecules. In short, a single DNA molecule that is optically mapped according to the present method can then be assigned map locations by exploring and analyzing large quantities of pre-existing genome sequence data by automatic and semi-automatic computational means.

Gentig software was used for image processing and correction. See Anantharaman, Mishra, and Schwartz, 1998, "Genomics via optical mapping III: Contiging genomic DNA and variations." *NYU Technical Report* 760.

Transcription reaction conditions are described in the Examples.

15.1.1. Screen for Optimum Labeled Nucleotides

To distinguish DNA from nascent RNA transcript by fluorescence microscopy, optimum fluorescently-labeled NTPs for nascent RNA labeling should be identified a priori. Five fluochrome-labeled UTPs were screened in terms of their fluorescence intensity, photo-stability and background introduction by using a linear plasmid DNA (~4 kb) as template. The plasmid DNA has a strong T7 RNA polymerase promoter, was linearized with EcoRI giving a 4 kb DNA template with 1 kb downstream of the promoter. The results are shown in Table 6.

TABLE 6

Comparison of different fluorochrome labeled 1 kb RNA

| Fluorochrome Labeled NTP | Fluores-cein-12-UTP | Rhodamine Green-5-UTP | Tetramethyl rhodamine-6-UTP | Texas Red-5-UTP | BODIPY TR-14-UTP |
|---|---|---|---|---|---|
| Fluorescence intensity (arbitrary units) | Weak (100~200) | Strong (400~500) | Strong (400~500) | Intermediate (350~450) | Weak (250~350) |
| Photo-stability (half-life) | <5S | ~1 min | ~1 min | 15s | 10s |
| Background | low | Medium | Medium | High | Low |
| Ex/Em (nm/nm) | 495/525 (green) | 505/530 (green) | 550/570 (orange) | 595/615 (Red) | 595/625 (Red) |

15.1. EXAMPLES

Materials and Methods

For all of the Examples that follow, the following materials were used.

Glass coverslips (22×22 mm²) were acid-cleaned and then derivatized in 250 ml distilled water with the appropriate amount of silane (usually 30~60 μl N-trimethoxysilylpropyl-N,N,N-trimethylammonium chloride, referred to as "trimethyl silane", and, in some instances 3 μl vinyltrimethoxy silane, referred to as "vinyl silane.".

To stabilize the elongation complex during the on-surface restriction enzyme digestion, and to keep the small fragments from the fluid flow, and to have a controlled digestion time window, a cross-linked acrylamide overlay system (CAOS) was used. In this approach, a very thin polyacrylamide gel is set on top of the nucleic acid immobilized on the substrate. The vinyl silane functions to cross-link the glass substrate to the acrylamide overlay, thereby providing a controlled environment in which the reactions can take place. As discussed above, the trimethylsilane confers a positive charge to the substrate surface and works in concert with induced fluid flows to elongate and bind nucleic acid molecules and complexes to the surface.

Nucleic acid molecules and complexes were imaged by a Zeiss Axivert 135 microscope equipped for epifluorescence and automatic image collection by charge-coupled device (CCD) camera. A 100x objective and XF 108 filter were used for the detection of TAMRA-6-UTP and a YOYO-1 filter for the detection of DNA for the image collection.

These experiments show that rhodamine-labeled (Rhodamine green, tetramethylrhodamine) NTP works well for RNA labeling. Additional experiments, results not shown, also revealed that T7 RNA polymerase actively incorporated fluorochrome-labeled ribonucleoside triphosphates into nascent transcripts. Consequently, TMR-6-UTP (tetramethylrhodamine-6-UTP) was overall found to be the optimal fluorochrome labeled NTP because of its spectral characteristics (these being distinct from stained DNA), its photo-stability, and low apparent background in images.

15.1.2. In Vitro Transcription by T7 RNA Polymerase

To observe elongation complexes on a relatively long DNA template, the 44 kb cosmid DNA (380H5 from human chromosome 16) with a T7 RNA promoter at the insert site was chosen for this Example. The circular cosmid DNA was linearized by the restriction enzyme SalI; and then used as transcription template. A map of the cosmic is shown in FIG. 2. The transcription reaction volume was 20 ml and contained 20 ng/ml linear cosmid template, 0.5 mM each at ATP, CTP and GTP, 0.05 mM UTP (total UTP/F-UTP=10:1), 1 ml RNase inhibitor, 1 ml T7 RNA polymerase (the ratio of RNA polymerase to promoter was about 50/1), 1× transcription buffer (40 mM Tris-HCl, 6 mM $MgCl_2$, 2 mM spermidine, 10 mM DTT, pH 7.9 @ 25° C.), and incubation was at 37° C. for 2 min, 5 min, 10 min, 30 min, 60 min.

The reaction was stopped by adding EDTA to a final concentration of 20 mM or by quick freezing at −20° C. Spin columns were used to remove unincorporated NTPs. After mounting the transcription reaction products (1:100 dilution) on the optical mapping surface, strongly fluorescent spots are easily seen under both the RNA filter and the DNA filter; see FIG. 2, which is a view of the reaction products with the RNA filter, and FIG. 2, which is the same view using the DNA filter. Notably, DNA backbones were only detected under DNA filter.

Collectively, FIGS. 24A through 24C are photograph illustrating the identification and localiztion of labeled RNA transcripts on DNA templates. In FIG. 21A, the linear cosmid DNA was transcribed in vitro by T7 RNA polymerize for 30 min in the tube, then the reaction products were mounted on the optical mapping surface and images taken using the RNA filter (suitable for TMR-labeled UTP). FIG. 2 is an images of the same location taken with the DNA filter (suitable for YOYO-1 stained DNA). The bright spots were shown to lie on the DNA backbone. In FIG. 24C, the DNA was digested with Xba I on the optical mapping surface to orient the complexes. FIG. 24D, as noted above, is a diagram of the 44 kb cosmid (380H5) with corresponding promoters (T3 RNA polymerase; T7 RNA polymerase); arrows show the transcription direction. Bars show Xba I cleavage sites.

The bright spots in FIGS. 24A, 24B, and 24C are putative elongation complexes. The complexes showed very strong intensity under DNA filter (suitable for the YOYO stained DNA). In this Example, the emission from the RNA incorporated with TAMRA-6-UTP is detected using this particular DNA filter because the filter is broad band-pass. Using a narrow band-pass filter will eliminate the RNA signal from the DNA signal. Additionally, it might be that YOYO-1 intercalated into RNA with secondary structure, or even bound to single strand RNA, which would give a weak emission, although this explanation is purely hypothetical.

15.1.3. Confirmation of RNA in Complexes

To confirm the existence of labeled RNA in the complexes, RNase digestion was performed both in a test tube and on the glass surface. The results are shown in FIGS. 25A through 25F.

FIG. 22A shows fluorochrome-labeled elongation complexes digested with RNase. In FIG. 22A, elongation complexes were digested by RNase in the a test tube and then mounted on the optical mapping surface and images using a RNA filter set. In FIG. 22B, elongation complexes were directly digested on the optical mapping surface by RNase and imaged using a RNA filter set. In FIG. 22C, is a control showing transcription complexes on the surface without RNase digestion. FIGS. 25D, 25E, and 25F, are images taken using a DNA filter set of YOYO-1 stained transcription complexes and template following RNase digestion. These images show diminished RNA fluorescence intensity and the presence of putative compacted DNA template (spots).

The signal under RNA filter disappeared or became obviously weaker after digestion. It seems that the labeled RNA was digested into the single fluorochrome-labeled NMPs or small oligonucleotides, which then diffused away from the original complex. However, using the DNA filter, small spots were still imaged associated with the DNA template after digestion. If these spots represent elongation complexes, RNA polymerase might partially protect the RNA from digestion with RNase. So the compact elongation complexes made of small piece of RNA might still exist after digestion. Because of excess RNA polymerase in the reaction, this particular spot might comprise of a lot of small elongation complexes, which would still twist DNA and give an obvious strong signal.

Proteinase K digestion was also used to digest these complexes in the tube to test whether the stability of the complex is dependent on RNA polymerase. From the result (not shown), these particular complexes were partially destabilized by eliminating the RNA polymerase.

15.1.4. In Vitro Transcription Using *E. Coli* Genomic DNA

Genomic DNA was prepared from *E. coli* K-12 MG1655 using standard protocols and published transcription reaction buffer conditions. Pfachl et al. 1979, *J Mol. Biol.* 127:339–344; Leirmo et al., 1987, *Biochemistry* 26:2095–2101.

For example, the transcription reactions were performed in 30 ml of reaction solution that contained 10 ng/ml *E. coli* genomic DNA, 0.05 mM each of ATP, CTP, GTP and UTP (total UTP/F-UTP was 10:1), 1 ml RNase inhibitor, 1.0 ml *E. coli* RNA holoenzyme (the RNA polymerase to operon molar ratio was 4/1), 1× transcription buffer (40 mM Tris-HCl, 70 mM $KCl_1$, 0.01% Triton X-100, 10 mM $MgCl_2$, pH 7.5@25° C.), 1 mM DTT, and 100 mg/ml BSA. The reactions were incubated at 37° C. for 30 min and stopped by addition of EDTA to 20 mM. A reaction aliquot was diluted and imaged on an optical surface. The results are shown in FIGS. 26A, 26B, and 26D. Specifically, in FIG. 2 the reaction products were mounted on an optical mapping surface and images taken using an XF108 filter (suitable for TMR-labeled RNA). The bright spots are putative transcription complexes. In FIG. 2, the filter was switched to a YOYO-1 filter set and images were taken showing compacted structures. In FIG. 23C, the fluorescent intensity of the transcription complexes shown in FIG. 23A was analyzed along the length of a DNA molecule. The X-coordinate shows the DNA backbone length, the Y-coordinate shows the arbitrary intensity. The label shows the transcription complex position relative to the left-end of the molecule. FIG. 26D is an image of the DNA templates with the complexes after digestion with Xho I.

The imaging results indicate that elongation complexes were captured on the DNA templates. Analysis showed that roughly 10–20% of possible operons had associated elongation complexes.

What is claimed is:

1. A method of analyzing enzymatic and chemical reactions of nucleic acids, the method comprising:
   (a) elongating and fixing onto a surface of a substrate a plurality of nucleic acid molecules in such a fashion that each individual nucleic acid molecule is fixed along its length onto the surface of the substrate with a small degree of relaxation so that the nucleic acid molecules are individually analyzable and accessible for enzymatic and chemical reactions; then
   (b) subjecting the elongated and fixed nucleic acid of step (a) to an enzymatic or chemical reaction in the presence of a labeled reagent that generates signals correlating to the enzymatic or chemical reaction; and then
   (c) acquiring and compiling the signals generated by the labeled reagent, whereby the enzymatic or chemical reaction of step (b) is analyzed.

2. The method of claim 1, wherein in step (a), DNA is elongated and fixed to the substrate.

3. The method of claim 1, wherein in step (a), RNA is elongated and fixed to the substrate.

4. The method of claim 1, wherein in step (a), the nucleic acid is fixed to a glass substrate.

5. The method of claim 1, wherein in step (a), the nucleic acid is fixed to a glass substrate derivatized by a coating of a cationic substance disposed thereon.

6. The method of claim 1, wherein in step (a), the nucleic acid is fixed to a glass substrate derivatized by a coating selected from the group consisting of poly(lysine), 3-aminopropyltriethoxysilane, N-(trimethoxysilyl)propyl-N,N,N-trimethylammonium chloride, and vinyltrimethoxysilane.

7. The method of claim 1, wherein in step (b), the fixed nucleic acids are subjected to an enzymatic or chemical reaction in the presence of fluorescently-labeled reagent.

8. The method of claim 7, wherein in step (c), the signals generated by the fluorescently-labeled reagent are acquired using a camera and a microscope.

9. The method of claim 8, further comprising, after step (c):
   (d) processing the compiled signals using Bayesian estimation.

10. A method of analyzing enzymatic and chemical reactions of nucleic acids, the method comprising:
    (a) elongating and fixing onto a surface of a substrate a plurality of nucleic acid molecules in such a fashion that each individual nucleic acid molecule is fixed along its length onto the surface of the substrate with a small degree of relaxation so that the nucleic acid molecules are individually analyzable and accessible for enzymatic and chemical reactions; then
    (b) subjecting the elongated and fixed nucleic acids of step (a) to an enzymatic transcription reaction in the presence of a labeled reagent that generates signals correlating to the enzymatic transcription reaction; and then
    (c) acquiring and compiling the signals generated by the labeled reagent, whereby the enzymatic transcription reaction of step (b) is analyzed.

11. The method of claim 10, wherein in step (b), the fixed nucleic acids are subjected to an enzymatic transcription reaction in the presence of labeled reagent that comprises fluorescently-labeled NTP.

12. The method of claim 11, wherein in step (c), the signals generated by the fluorescently-labeled NTP are acquired using a camera and a microscope.

13. The method of claim 10, further comprising, after step (c):
    (d) processing the compiled signals using Bayesian estimation.

14. The method of claim 10, wherein in step (a), genomic DNA molecules are elongated and fixed onto the surface of the substrate.

15. The method of claim 10, further comprising after step (c):
    (d) manipulating the acquired and compiled signals generated by the labeled reagent into an image, and then observing an individual elongated nucleic acid molecule for appearance of complexes corresponding to transcription events in the individual nucleic acid molecule.

16. The method of claim 10, further comprising, after the transcription reaction of step (b) and prior to step (c), cleaving the nucleic acid molecules with a restriction enzyme to generate restriction fragments.

17. The method of claim 16, further comprising after step (c):
    (d) manipulating the acquired and compiled signals generated by the labeled reagent into an image, and then:
        (i) observing an individual elongated nucleic acid molecule for appearance of complexes corresponding to transcription events in the individual nucleic acid molecule; and (ii) observing the individual elongated nucleic acid molecule of step (d) (i) for appearance of gaps corresponding to cleavage sites between restriction fragments.

18. The method of claim 17, further comprising reiteratively repeating steps (d), (d) (i), and (d) (ii) on additional individual elongated nucleic acid molecules, to thereby generate additional images, and then:

(e) compiling an ordered map correlating transcription event sites and restriction enzyme cleavage sites based upon the images.

19. The method of claim 18, wherein in step (a), genomic DNA molecules are elongated and fixed onto the surface of the substrate, and in step (e), compiling an ordered, genome-wide map correlating transcription event sites and restriction enzyme cleavage sites.

20. The method of claim 19, further comprising:

(f) comparing the map of step (e) to known genomic sequences, whereby it can be determined from where in a genome a single nucleic acid molecule originated.

21. A method of analyzing enzymatic and chemical reactions of nucleic acids, the method comprising:

(a) elongating and fixing onto a surface of a substrate a plurality of nucleic acid molecules in such a fashion that each individual nucleic acid molecule is fixed along its length onto the surface of the substrate with a small degree of relaxation so that the nucleic acid molecules are individually analyzable and accessible for enzymatic and chemical reactions; then (b) subjecting the elongated and fixed nucleic acid of step (a) to a transcription reaction followed by a restriction reaction in the presence of a labeled reagent that generates signals correlating to the transcription reaction and the restriction reaction, respectively; then (c) acquiring and compiling the signals generated by the labeled reagent; then (d) manipulating the acquired and compiled signals generated by the labeled reagent into an image, then:

(i) observing an individual elongated nucleic acid molecule for appearance of complexes corresponding to transcription events in the individual nucleic acid molecule; and (ii) observing the individual elongated nucleic acid molecule of step (d) (i) for appearance of gaps corresponding to cleavage sites between restriction fragments; then (e) reiteratively repeating steps (d), (d) (i), and (d) (ii) on additional individual elongated nucleic acid molecules, to thereby generate additional images, and then (f) compiling an ordered map correlating transcription event sites and restriction enzyme cleavage sites based upon the images.

22. The method of claim 21, further comprising, after step (f), comparing the map of step (f) to known genomic sequences, whereby it can be determined from where within a genome a single nucleic acid molecule originated.

23. A method of analyzing enzymatic and chemical reactions of nucleic acids, the method comprising:

(a) subjecting nucleic acid molecules to an enzymatic or chemical reaction in the presence of a labeled reagent that generates signals correlating to the enzymatic or chemical reaction, thereby generating nucleic acid reaction products; and then (b) elongating and fixing onto a surface of a substrate a plurality of the nucleic acid reaction products of step (a) in such a fashion that each individual nucleic acid molecule is fixed along its length onto the surface of the substrate with a small degree of relaxation so that the nucleic acid molecules are individually analyzable and accessible for further enzymatic and chemical reactions; then (c) acquiring and compiling the signals generated by the labeled reagent, whereby the enzymatic or chemical reaction of step (a) is analyzed.

24. The method of claim 23, wherein in step (b), DNA reaction products are elongated and fixed to the substrate.

25. The method of claim 23, wherein in step (b) RNA reaction products are elongated and fixed to the substrate.

26. The method of claim 23, wherein in step (b), the nucleic acid reaction products are fixed to a glass substrate.

27. The method of claim 23, wherein in step (b), the nucleic acid reaction products are fixed to a glass substrate derivatized by a coating of a cationic substance disposed thereon.

28. The method of claim 23, wherein in step (b), the nucleic acid reaction products are fixed to a glass substrate derivatized by a coating selected from the group consisting of poly(lysine), 3-aminopropyl-triethoxysilane, N-(trimethoxysilyl) propyl-N,N,N-trimethylammonium chloride, and vinyltrimethoxysilane.

29. The method of claim 23, wherein in step (a), the fixed nucleic acids are subjected to an enzymatic or chemical reaction in the presence of a fluorescently-labeled reagent.

30. The method of claim 29, wherein in step (c), the signals generated by the fluorescently-labeled reagent are acquired using a camera and a microscope, and the signals are compiled using a programmable computer.

31. The method of claim 30, further comprising, after step (c):

(d) processing the compiled signals using Bayesian estimation.

32. The method of claim 23, wherein in step (a), the nucleic acid molecules are subjected to an enzymatic transcription reaction.

33. The method of claim 32, wherein in step (a), the nucleic acid molecules are subjected to an enzymatic transcription reaction in the presence of labeled reagent that comprises fluorescently-labeled NTP.

34. The method of claim 33, wherein in step (c), the signals generated by the fluorescently-labeled NTP are acquired using a camera and a microscope.

35. The method of claim 32, further comprising, after step (c):

(d) processing the compiled signals using Bayesian estimation.

36. The method of claim 32, further comprising after step (c):

(d) manipulating the acquired and compiled signals generated by the labeled reagent into an image, and then observing an individual elongated nucleic acid molecule for appearance of complexes corresponding to transcription events in the individual nucleic acid molecule.

37. The method of claim 32, further comprising, after the transcription reaction of step (a) and prior to step (b), cleaving the nucleic acid molecules with a restriction enzyme to generate restriction fragments.

38. The method of claim 37, further comprising after step (c):

(d) manipulating the acquired and compiled signals generated by the labeled reagent into an image, and then:

(i) observing an individual elongated nucleic acid molecule for appearance of complexes corresponding to transcription events in the individual nucleic acid molecule; and (ii) observing the individual elongated nucleic acid molecule of step (d) (i) for appearance of gaps corresponding to cleavage sites between restriction fragments.

39. The method of claim 38, further comprising reiteratively repeating steps (d), (d) (i), and (d) (ii) on additional individual elongated nucleic acid molecules, to thereby generate additional images, and then:

(e) compiling an ordered map correlating transcription event sites and restriction enzyme cleavage sites based upon the images.

40. The method of claim 39, wherein in step (a), genomic DNA molecules are used, and in step (e), compiling an ordered, genome-wide map correlating transcription event sites and restriction enzyme cleavage sites.

41. The method of claim 40, further comprising:

(f) comparing the map of step (e) to known genomic sequences, whereby it can be determined from where in a genome a single nucleic acid molecule originated.

42. A method of analyzing enzymatic and chemical reactions of nucleic acids, the method comprising:

(a) subjecting a nucleic acid to a transcription reaction followed by a restriction reaction in the presence of a labeled reagent that generates signals correlating to the transcription and the restriction reaction, respectively, thereby generating nucleic acid reaction products; then (a) elongating and fixing onto a surface of a substrate a plurality of nucleic acid reaction products of step (a) in such a fashion that each individual nucleic acid molecule is fixed along its length onto the surface of the substrate with a small degree of relaxation so that the nucleic acid molecules are individually analyzable and accessible for enzymatic and chemical reactions; then (c) acquiring and compiling the signals generated by the labeled reagent; then (d) manipulating the acquired and compiled signals generated by the labeled reagent into an image, then:

(i) observing an individual elongated nucleic acid molecule for appearance of complexes corresponding to transcription events in the individual nucleic acid molecule; and (ii) observing the individual elongated nucleic acid molecule of step (d) (i) for appearance of gaps corresponding to cleavage sites between restriction fragments; then (e) reiteratively repeating steps (d), (d) (i), and (d) (ii) on additional individual elongated nucleic acid molecules, to thereby generate additional images, and then (f) compiling an ordered map correlating transcription event sites and restriction enzyme cleavage sites based upon the images.

* * * * *

SEQUENCE LISTING

<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: primer -continued

```
<400> SEQUENCE: 1
gatgagttcg tgtccgtaca actgg                                         25

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 2
ggttatcgaa atcagccaca gcgc                                          24

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 3
gtaaaacgac ggccagt                                                  17

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 4
aacagctatg accatg                                                   16

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 5
cattaatgct atgcagaaaa tcttag                                        26

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 6
ttctcaacca gaagaaaggg ccttcacagt                                    30

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 7
tacatcaggc cttcatcctg aggattttat caa                                33

<210> SEQ ID NO 8
<211> LENGTH: 31
```

```
-continued

<212> TYPE: DNA
<213> ORGANISM: Artificial Sequence
<220> FEATURE:
<223> OTHER INFORMATION: Description of Artificial Sequence: primer

<400> SEQUENCE: 8
ccagtgaact taaagaattt gtcaatccta g                                  31

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 9
tgttccaaag ataatagaaa tgaca                                         25
```